United States Patent
Gouvea et al.

(10) Patent No.: US 11,692,210 B2
(45) Date of Patent: Jul. 4, 2023

(54) ANAEROBIC FERMENTATIVE PRODUCTION OF FURANDICARBOXYLIC ACID

(71) Applicant: Braskem S.A., Camacari (BR)

(72) Inventors: Iuri Estrada Gouvea, Campinas (BR); Marcos Rogerio Simoes, Campinas (BR); Mariana Trovo Marchesin, Campinas (BR); Aline Silva Romão Dumaresq, Campinas (BR)

(73) Assignee: BRASKEM S.A., Camaçari (BR)

( * ) Notice: Subject to any disclaimer, the term of this patent is extended or adjusted under 35 U.S.C. 154(b) by 0 days.

(21) Appl. No.: 17/464,139

(22) Filed: Sep. 1, 2021

(65) Prior Publication Data

US 2022/0064683 A1  Mar. 3, 2022

Related U.S. Application Data

(60) Provisional application No. 63/073,193, filed on Sep. 1, 2020.

(51) Int. Cl.

| | |
|---|---|
| C12N 15/81 | (2006.01) |
| C12P 17/04 | (2006.01) |
| C12N 9/88 | (2006.01) |
| C12N 9/10 | (2006.01) |
| C12N 9/12 | (2006.01) |
| C12N 9/00 | (2006.01) |
| C12N 9/02 | (2006.01) |
| C12N 9/04 | (2006.01) |

(52) U.S. Cl.
CPC ............ *C12P 17/04* (2013.01); *C12N 9/0006* (2013.01); *C12N 9/0008* (2013.01); *C12N 9/1029* (2013.01); *C12N 9/1205* (2013.01); *C12N 9/1217* (2013.01); *C12N 9/88* (2013.01); *C12N 9/93* (2013.01); *C12Y 101/01001* (2013.01); *C12Y 102/0101* (2013.01); *C12Y 203/01008* (2013.01); *C12Y 207/01019* (2013.01); *C12Y 207/02012* (2013.01); *C12Y 401/01039* (2013.01); *C12Y 401/02009* (2013.01); *C12Y 401/02022* (2013.01); *C12Y 602/01001* (2013.01); *C12N 15/81* (2013.01)

(58) Field of Classification Search
CPC .................................. C12N 9/00; C12N 9/02
See application file for complete search history.

(56) References Cited

U.S. PATENT DOCUMENTS

| | | |
|---|---|---|
| 10,066,234 B2 | 9/2018 | Pompon et al. |
| 10,093,937 B2 | 10/2018 | Van Maris et al. |
| 10,294,482 B2 | 5/2019 | Milo et al. |
| 2016/0273004 A1 | 9/2016 | Shaw, IV et al. |
| 2017/0088861 A1 | 3/2017 | Andrei et al. |
| 2020/0277639 A1 | 9/2020 | Alexandrino et al. |
| 2022/0064682 A1* | 3/2022 | Gouvea ................ C12N 9/1205 |

OTHER PUBLICATIONS

Guadalupe-Medina, V. et al., Carbon dioxide fixation by Calvin-Cycle enzymes improves ethanol yield in yeast. Biotechnol Biofuels 6, 125 (2013).
Papapetridis, I. et al., Optimizing anaerobic growth rate and fermentation kinetics in *Saccharomyces cerevisiae* strains expressing Calvin-cycle enzymes for improved ethanol yield. Biotechnol Biofuels 11, 17 (2018).
Siegel, J. B. et al., Computational protein design enables a novel one-carbon assimilation pathway. PNAS 112 (12) 3704-3709 (2015).
Henard, C. A. et al., Phosphoketolase pathway engineering for carbon-efficient biocatalysis. Current Opinion in Biotechnology 36, 183-188 (2015).
Bergman, A. et al., Functional expression and evaluation of heterologous phosphoketolases in *Saccharomyces cerevisiae*. AMB Expr 6, 115 (2016).
Sonderegger, M. et al., Metabolic Engineering of a Phosphoketolase Pathway for Pentose Catabolism in *Saccharomyces cerevisiae*. Applied and Environmental Microbiology 70 (5) 2892-2897 (2004).

* cited by examiner

*Primary Examiner* — Tekchand Saidha
(74) *Attorney, Agent, or Firm* — Morgan, Lewis & Bockius LLP

(57) ABSTRACT

The present disclosure provides recombinant microorganisms and methods for the anaerobic production of 2,4-furandicarboxylic acid from one or more carbon sources. The microorganisms and methods provide redox-balanced and ATP positive pathways for co-producing 2,4-furandicarboxylic acid with ethanol and for co-producing 2,4-furandicarboxylic acid with ethanol and 1-propanol. The method provides recombinant microorganisms that express endogenous and/or exogenous nucleic acid molecules encoding polypeptides that catalyze the conversion of a carbon source into 2,4-furandicarboxylic acid and that coupled the 2,4-furandicarboxylic acid pathway with an additional metabolic pathway.

23 Claims, 4 Drawing Sheets

Specification includes a Sequence Listing.

ANAEROBIC FERMENTATIVE PRODUCTION OF FURANDICARBOXYLIC ACID

CROSS-REFERENCE TO RELATED APPLICATIONS

This application claims priority to U.S. Provisional Application No. 63/073,193 filed Sep. 1, 2020, entitled "ANAEROBIC FERMENTATIVE PRODUCTION OF FURANDICARBOXYLIC ACID," the disclosure of which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 127125_5017 US Sequence Listing.txt. The text file is about 94.4 KB, was created on Aug. 30, 2021, and is being submitted electronically via EFS-Web.

BACKGROUND 2,5-Furandicarboxylic acid (2,5-FDCA) has gained much attention due to its potential of substituting terephthalic acid in the synthesis of polyesters, specially polyethylene terephthalate (PET) (Sousa, Andreia F., et al. "Biobased polyesters and other polymers from 2, 5-furandicarboxylic acid: a tribute to furan excellency." Polymer chemistry 6.33 (2015): 5961-5983). Substituting terephthalic acid to its furan analogue 2,5-FDCA in PET can lead to 2,5-furandicarboxylate (2,5-PEF) and this polymer has several advantages when compared to PET. In one aspect, 2,5-PEF has better thermal, barrier and mechanical properties when compared to its counterpart (PEP Report 294). Furthermore, as it is known that ethylene glycol could be produced from renewable resources, then 2,5-PEF could be 100% renewable as opposed to the semi-renewable PET.

Despite all the aforementioned advantages of 2,5-FDCA in comparison to terephthalic acid, 2,5-FDCA production cost is still a current limitation in expanding monomer usage. Existing technologies are not cost-competitive when compared to terephthalic acid. One of the possible reasons for this is related to the several sequential industrial steps required. One issue that could help reduce 2,5-FDCA production costs is finding a direct fermentation route from sugar to the desired molecule, but such a route has never been reported.

2,4-FDCA, an isomer of 2,5-FDCA, possesses unique properties compared to the well-studied 2,5-FDCA. Catalytically polymerizing 2,4-FDCA with a diol yields a polymer composed of 2,4-FDCA with valuable properties. In one study, Thiyagarajan and collaborators (2014) compare polyesters made of 2,4-FDCA, 3,4-FDCA, 2,5-FDCA and terephthalic acid and concluded that 2,4-FDCA and 3,4-FDCA polyesters can be made in sufficient molecular weights by industrially applicable methods (Thiyagarajan, Shanmugam, et al. "Biobased furandicarboxylic acids (FDCAs): effects of isomeric substitution on polyester synthesis and properties." Green Chemistry 16.4 (2014): 1957-1966). In another study, Thiyagarajan and colleagues concluded that structural analysis of 2,4-FDCA and 2,5-FDCA reveal that 2,4-FDCA possesses more linear characteristics resembling terephthalic acid than does 2,5-FDCA. These features make 2,4-FDCA an interesting monomer for synthetic polyesters (Thiyagarajan et al. "Concurrent formation of furan-2,5- and furan-2,4-dicarboxylic acid: unexpected aspects of the Henkel reaction" RSC Advances 3 (2013): 15678-15686). Further, these materials have properties unlike 2,5-FDCA polyesters (Bourdet et al. "Molecular Mobility in Amorphous Biobased Poly (ethylene 2, 5-furandicarboxylate) and Poly (ethylene 2, 4-furandicarboxylate)." Macromolecules 51.5 (2018): 1937-1945).

In certain cases, 2,4-FDCA polymers have been reported to have superior properties to those possessed by 2,5-FDCA polymers. Cui and collaborators (2016) report that the bond-angle between the double carboxyl groups linking with the central ring is a key factor that influences the stability of nematic liquid crystal molecules such as those utilized in LCD TVs, notebook computers, and other display elements (Cui, Min-Shu, et al. "Production of 4-hydroxymethylfurfural from derivatives of biomass-derived glycerol for chemicals and polymers." ACS Sustainable Chemistry & Engineering 4.3 (2016): 1707-1714). The first discovered liquid crystal, terephthalic acid diester molecules has a bond-angle between two carboxyl groups of 180°. In comparison, 2,5-furan dicarboxylic acid has a bond-angle between two carboxyl groups of 137°. Significantly, 2,4-furan dicarboxylic acid has a bond-angle between two carboxyl groups of 160° making it more suitable for synthesis of nematic liquid crystal molecules.

Despite these potential applications of 2,4-FDCA polymers, the production cost of 2,4-FDCA is a current bottleneck in expanding this monomer to the applications as described by Cui and collaborators (2016). Previous syntheses of 2,4-substituted furans, including 2,4-FDCA, required multiple synthetic steps and therefore 2,4-FDCA-derived polymers are cost-prohibitive by currently available methodologies and industrial techniques. More efficient and cost-effective production of 2,4-FDCA is therefore needed.

SUMMARY

The present disclosure provides direct and anaerobic fermentation pathways for 2,4-FDCA production in a recombinant microorganism such as an ethanol-producing yeast. The pathways advantageously have a redox-cofactor balance and yield positive ATP by coupling FDCA production with electron consuming and ATP-positive pathways, thereby providing more efficient and cost-effective pathways for 2,4-FDCA production.

The present disclosure provides a recombinant microorganism such as an ethanol-producing yeast comprising: (a) at least one nucleic acid molecule encoding a polypeptide that catalyzes the production of 4-hydroxymethylfurfural phosphate from glyceraldehyde 3-phosphate (G3P); (b) at least one nucleic acid molecule encoding a polypeptide that catalyzes the production of 4-hydroxymethylfurfural (4-HMF) from 4-hydroxymethylfurfural phosphate; (c) at least one nucleic acid molecule encoding one or more polypeptides that catalyze the production of 2,4-furandicarboxylic acid (2,4-FDCA) from 4-HMF, either directly or through production of one or more intermediates; (d) at least one nucleic acid molecule encoding a polypeptide that catalyzes the production of ribulose-1,5-bisphosphate from ribulose-5-phosphate; and (e) at least one nucleic acid molecule encoding a polypeptide that catalyzes the production of two molecules of glycerate-3-phosphate from the combination of $CO_2$ with ribulose-1,5-bisphosphate. In some embodiments, the intermediates are furan-2,4-dicarbaldehyde, 4-(hydroxymethyl)furoic acid, 4-formylfuran-2-carboxylate, 4-formylfuran-2-carboxylate, and/or 2-formyl-furan-4-carboxylate.

The present discloses also provides a recombinant microorganism that is an ethanol-producing yeast comprising: (a) at least one exogenous nucleic acid molecule encoding a polypeptide that catalyzes the production of 4-hydroxymethylfurfural phosphate from glyceraldehyde 3-phosphate (G3P); (b) at least one endogenous and/or exogenous nucleic acid molecule encoding a polypeptide that catalyzes the production of 4-hydroxymethylfurfural (4-HMF) from 4-hydroxymethylfurfural phosphate; (c) at least one endogenous and/or exogenous nucleic acid molecule encoding one or more polypeptides that catalyze the production of 2,4-furandicarboxylic acid (2,4-FDCA) from 4-HMF through the production of the intermediates furan-2,4-dicarbaldehyde, 4-(hydroxymethyl)furoic acid, 4-formylfuran-2-carboxylate, 4-formylfuran-2-carboxylate, and/or 2-formyl-furan-4-carboxylate, wherein the production of 2,4-FDCA leads to the reduction of (i) NAD to NADH or (ii) NADP to NADPH; (d) at least one nucleic acid molecule encoding a polypeptide that catalyzes the production of ribulose-1,5-bisphosphate from ribulose-5-phosphate; and (e) at least one nucleic acid molecule encoding a polypeptide that catalyzes the production of two molecules of glycerate-3-phosphate from the combination of $CO_2$ with ribulose-1,5-bisphosphate; and wherein the recombinant microorganism utilizes the glycerate-3-phosphate from (e) and the NADH and/or NADPH generated as a byproduct of 2,4-FDCA production at (c) to produce ethanol; and wherein the 2,4-FDCA and ethanol are coproduced under anaerobic or microaerobic conditions.

In some embodiments, the polypeptide that catalyzes the production of ribulose-1,5-bisphosphate from ribulose-5-phosphate is a phosphoribulokinase (PRK).

In some embodiments, the polypeptide that catalyzes the production of glycerate-3-phosphate from the combination of $CO_2$ with ribulose-1,5-bisphosphate is a ribulose-1,5-bisphosphate carboxylase (RuBisCO). In some embodiments, the RuBisCO is selected from Form I, Form II, Form III, or a combination thereof. In some embodiments, the recombinant microorganism further comprises at least one nucleic acid molecule encoding a chaperone protein.

In some embodiments, the microorganism further comprises at least one genetic modification that leads to a down-regulation or a deletion of an enzyme in a glycerol-production pathway. In some embodiments, the enzyme in the glycerol-production pathway is a GPD1 and/or a GPD2, and/or a glycerol-3-phosphate phosphatase.

In some embodiments, the microorganism further comprises at least one nucleic acid molecule encoding a chaperone protein.

In some embodiments, the microorganism utilizes NADH and/or NADPH produced as a byproduct of 2,4-FDCA production to produce ethanol.

The present disclosure provides a recombinant microorganism comprising: (a) at least one nucleic acid molecule encoding a polypeptide that catalyzes the production of 4-hydroxymethylfurfural phosphate from glyceraldehyde 3-phosphate (G3P); (b) at least one nucleic acid molecule encoding a polypeptide that catalyzes the production of 4-hydroxymethylfurfural (4-HMF) from 4-hydroxymethyl-furfural phosphate; (c) at least one nucleic acid molecule encoding one or more polypeptides that catalyze the production of 2,4-furandicarboxylic acid (2,4-FDCA) from 4-HMF, either directly or through production of intermediates; (d) at least one nucleic acid molecule encoding a polypeptide that catalyzes the production of acetyl phosphate and D-glyceraldehyde-3-phosphate from D-xylulose-5-phosphate and phosphate, and/or at least one nucleic acid molecule encoding a polypeptide that catalyzes the production of acetyl phosphate and erythrose-4-phosphate from fructose-6-phosphate and phosphate; (e) at least one nucleic acid molecule encoding one or more polypeptides that catalyze: (1) the production of acetyl-CoA from acetyl phosphate and free coenzyme A; and/or (2) the production of acetate from acetyl phosphate and the production of acetyl-CoA from acetate; and (f) at least one nucleic acid molecule encoding one or more polypeptides that catalyze: (1) the production of acetaldehyde from acetyl-CoA; and/or (2) the production of ethanol from acetyl-CoA. In some embodiments, the intermediates are furan-2,4-dicarbaldehyde, 4-(hydroxymethyl)furoic acid, 4-formylfuran-2-carboxylate, 4-formylfuran-2-carboxylate, and/or 2-formylfuran-4-carboxylate.

The present disclosure also provides a recombinant microorganism that is an ethanol-producing yeast comprising: (a) at least one exogenous nucleic acid molecule encoding a polypeptide that catalyzes the production of 4-hydroxymethylfurfural phosphate from glyceraldehyde 3-phosphate (G3P); (b) at least one endogenous and/or exogenous nucleic acid molecule encoding a polypeptide that catalyzes the production of 4-hydroxymethylfurfural (4-HMF) from 4-hydroxymethylfurfural phosphate; (c) at least one endogenous and/or exogenous nucleic acid molecule encoding one or more polypeptides that catalyze the production of 2,4-furandicarboxylic acid (2,4-FDCA) from 4-HMF through the production of the intermediates furan-2,4-dicarbaldehyde, 4-(hydroxymethyl)furoic acid, 4-formylfuran-2-carboxylate, 4-formylfuran-2-carboxylate, and/or 2-formylfuran-4-carboxylate, wherein the production of 2,4-FDCA leads to the reduction of (i) NAD to NADH or (ii) NADP to NADPH; (d) at least one nucleic acid molecule encoding a polypeptide that catalyzes the production of acetyl phosphate and D-glyceraldehyde-3-phosphate from D-xylulose-5-phosphate and phosphate, and/or at least one nucleic acid molecule encoding a polypeptide that catalyzes the production of acetyl phosphate and erythrose-4-phosphate from fructose-6-phosphate and phosphate; (e) at least one nucleic acid molecule encoding one or more polypeptides that catalyze: (1) the production of acetyl-CoA from acetyl phosphate and free coenzyme A; and/or (2) the production of acetate from acetyl phosphate and the production of acetyl-CoA from acetate; and (f) at least one nucleic acid molecule encoding one or more polypeptides that catalyze: (1) the production of acetaldehyde from acetyl-CoA; and/or (2) the production of ethanol from acetyl-CoA; and; wherein the recombinant microorganism utilizes the NADH and/or NADPH generated as a byproduct of 2,4-FDCA production at (c) to produce ethanol, and; wherein the 2,4-FDCA and ethanol are coproduced under anaerobic or microaerobic conditions.

In some embodiments, the recombinant microorganism further comprises at least one genetic modification that leads to a down-regulation or a deletion of an enzyme in a glycerol-production pathway. In some embodiments, the enzyme in the glycerol-production pathway is a glycerol-3-phosphate dehydrogenase. In some embodiments, the glycerol-3-phosphate dehydrogenase is classified as EC number 1.1.1.8. In some embodiments, the enzyme in the glycerol-production pathway is a glycerol-3-phosphate phosphatase. In some embodiments, the glycerol-3-phosphate phosphatase is classified as EC number 3.1.3.21. In some embodiments, the enzyme in the glycerol-production pathway is a GPD1 and/or a GPD2, and/or a glycerol-3-phosphate phosphatase.

In some embodiments, the polypeptide that catalyzes the production of acetyl phosphate and D-glyceraldehyde-3-phosphate from D-xylulose-5-phosphate and phosphate is a phosphoketolase. In some embodiments, the phosphoketolase is classified as EC number 4.1.2.9.

In some embodiments, the polypeptide that catalyzes the production of acetyl phosphate and erythrose-4-phosphate from fructose-6-phosphate and phosphate is a phosphoketolase. In some embodiments, the phosphoketolase is classified as EC number 4.1.2.22. In some embodiments, the phosphoketolase is a single-specificity phosphoketolase. In some embodiments, the phosphoketolase is a dual-specificity phosphoketolase.

In some embodiments, the polypeptide that catalyzes the production of acetyl-CoA from acetyl phosphate and free coenzyme A is a phosphotransacetylase. In some embodiments, the phosphotransacetylase is classified as EC number 2.3.1.8.

In some embodiments, the polypeptide that catalyzes the production of acetate from acetyl phosphate is an acetate kinase. In some embodiments, the acetate kinase is classified as EC number 2.7.2.12. In some embodiments, the polypeptide that catalyzes the production of acetyl-CoA from acetate is an acetyl-CoA synthetase or an acetate-CoA ligase. In some embodiments, the acetyl-CoA synthetase or an acetate-CoA ligase is classified as EC number 6.2.1.1.

In some embodiments, the polypeptide that catalyzes the production of acetaldehyde from acetyl-CoA is an acetaldehyde dehydrogenase. In some embodiments, the polypeptide that catalyzes the production of ethanol from acetaldehyde is an alcohol dehydrogenase.

In some embodiments, the polypeptide that catalyzes the production of ethanol from acetyl-CoA is a bifunctional acetaldehyde-alcohol dehydrogenase. In some embodiments, the bifunctional acetaldehyde-alcohol dehydrogenase is selected from enzymes classified as both EC number 1.2.1.10 and EC number 1.1.1.1. In some embodiments, the bifunctional acetaldehyde-alcohol dehydrogenase is an NADH- and/or NADPH-dependent bifunctional acetaldehyde-alcohol dehydrogenase. In some embodiments, the NADH- and/or NADPH-dependent bifunctional acetaldehyde-alcohol dehydrogenase is selected from enzymes classified as EC number 1.2.1.10 or EC number 1.1.1.2.

In some embodiments, the recombinant microorganism further comprises at least one genetic modification that leads to an up-regulation of an enzyme in a non-oxidative pentose phosphate pathway. In some embodiments, the enzyme in the non-oxidative pentose phosphate pathway is a transaldolase. In some embodiments, the transaldolase is classified as EC number 2.2.1.2. In some embodiments, the enzyme in the non-oxidative pentose phosphate pathway is a transketolase. In some embodiments, the transketolase is classified as EC number 2.2.1.1. In some embodiments, the enzyme in the non-oxidative pentose phosphate pathway is a ribose-5-phosphate isomerase. In some embodiments, the ribose-5-phosphate isomerase is classified as EC number 5.3.1.6. In some embodiments, the enzyme in the non-oxidative pentose phosphate pathway is a ribulose-5-phosphate 3-epimerase. In some embodiments, the ribulose-5-phosphate 3-epimerase is classified as EC number 5.1.3.1.

In some embodiments, the microorganism utilizes NADH and/or NADPH produced as a byproduct of 2,4-FDCA production to produce ethanol.

The present disclosure provides a recombinant microorganism comprising: (a) at least one nucleic acid molecule encoding a polypeptide that catalyzes the production of 4-hydroxymethylfurfural phosphate from glyceraldehyde 3-phosphate (G3P); (b) at least one nucleic acid molecule encoding a polypeptide that catalyzes the production of 4-hydroxymethylfurfural (4-HMF) from 4-hydroxymethylfurfural phosphate; (c) at least one nucleic acid molecule encoding one or more polypeptides that catalyze the production of 2,4-furandicarboxylic acid (2,4-FDCA) from 4-HMF, either directly or through production of intermediates; (d) at least one nucleic acid molecule encoding a polypeptide that catalyzes the production of oxaloacetate from phosphoenol pyruvate (PEP); (e) at least one nucleic acid molecule encoding one or more polypeptides that catalyze: (1) the production of malonate semialdehyde from oxaloacetate; and/or (2) the production of aspartate from oxaloacetate, the production of β-alanine from aspartate, and the production of malonate semialdehyde from β-alanine; (f) at least one nucleic acid molecule encoding a polypeptide that catalyzes the production of 3-hydroxypropionic acid (3-HP) from malonate semialdehyde; (g) at least one nucleic acid molecule encoding one or more polypeptides that catalyze the production of propionyl-CoA from 3-HP; and (h) at least one nucleic acid molecule encoding a polypeptide that catalyzes the production of 1-propanol from propionyl-CoA; and/or at least one nucleic acid molecule encoding one or more polypeptides that catalyze the production of propionaldehyde from propionyl-CoA and the production of 1-propanol from propionaldehyde. In some embodiments, the intermediates are furan-2,4-dicarbaldehyde, 4-(hydroxymethyl)furoic acid, 4-formylfuran-2-carboxylate, 4-formylfuran-2-carboxylate, and/or 2-formylfuran-4-carboxylate.

In some embodiments, the polypeptide that catalyzes the production of aspartate from oxaloacetate is an aspartate amino transferase. In some embodiments, the polypeptide that catalyzes the production of β-alanine from aspartate is an aspartate decarboxylase. In some embodiments, the polypeptide that catalyzes the production of malonate semialdehyde from β-alanine is a β-alanine pyruvate amino transferase and/or a β-alanine transaminase.

In some embodiments, the polypeptide that catalyzes the production of 3-HP from malonate semialdehyde is a 3-hydroxypropionic acid dehydrogenase.

In some embodiments, the polypeptide that catalyzes the production of propionyl-CoA from 3-HP is a propionyl-CoA synthase.

In some embodiments, the polypeptides that catalyze the production of propionyl-CoA from 3-HP are a 3-hydroxypropionyl-CoA synthetase/transferase, a 3-hydroxypropionyl-CoA dehydratase, and an acrylyl-CoA reductase.

In some embodiments, the polypeptide that catalyzes the production of 1-propanol from propionyl-CoA is an alcohol/aldehyde dehydrogenase.

In some embodiments, the polypeptide that catalyzes the production of propionaldehyde from propionyl-CoA is an aldehyde dehydrogenase (acetylating). In some embodiments, the polypeptide that catalyzes the production of 1-propanol from propionaldehyde is an alcohol dehydrogenase.

In some embodiments, the microorganism utilizes NADH and/or NADPH produced as a byproduct of 2,4-FDCA production to produce ethanol.

The present disclosure provides a recombinant microorganism that is an ethanol-producing yeast comprising: (a) at least one exogenous nucleic acid molecule encoding a polypeptide that catalyzes the production of 4-hydroxymethylfurfural phosphate from glyceraldehyde 3-phosphate (G3P); (b) at least one endogenous and/or exogenous nucleic acid molecule encoding a polypeptide that catalyzes the production of 4-hydroxymethylfurfural (4-HMF) from 4-hydroxymethylfurfural phosphate; (c) at least one endogenous and/or exogenous nucleic acid molecule encoding one or more polypeptides that catalyze the production of 2,4-furandicarboxylic acid (2,4-FDCA) from 4-HMF through the production of the intermediates furan-2,4-dicarbaldehyde, 4-(hydroxymethyl)furoic acid, 4-formylfuran-2-carboxylate, 4-formylfuran-2-carboxylate, and/or 2-formylfuran-4-carboxylate, wherein the production of 2,4-FDCA leads to the reduction of (i) NAD to NADH or (ii) NADP to NADPH; (d) a glycerol-production pathway, and; wherein the recombinant microorganism utilizes the NADH and/or NADPH generated as a byproduct of 2,4-FDCA production to produce glycerol, and; wherein the 2,4-FDCA and ethanol are coproduced under anaerobic or microaerobic conditions.

In some embodiments, the microorganism is selected from a bacterium, a fungus, or a yeast. In some embodiments, the microorganism is selected from *Saccharomyces* spp, *Saccharomyces cerevisiae*, *Issatchenkia* spp., *Hansenula* spp., *Debaryomyces* spp., *Rhodotula* spp., *Pachysolen* spp., *Cryptococcus* spp., *Trichosporon* spp., *Myxozyma* spp., *Candida* spp., *Kluyveromyces* spp., *Pichia* spp., *Schizosaccharomyces* spp., *Torulaspora* spp., *Zygosaccharomyces* spp., *Yarrowia* spp., *Yarrowia lipolytica*, *Scheffersomyces* spp. or *Scheffersomyces stipites*.

The present disclosure provides a method of co-producing 2,4-FDCA and ethanol comprising: contacting the recombinant microorganism as disclosed herein with a fermentable carbon source under conditions sufficient to produce 2,4-FDCA and ethanol. In some embodiments, the recombinant microorganism produces a molar ratio of ethanol:2,4-FDCA of greater than 1:1, such as greater than 2:1, greater than 3:1, or greater than 4:1. In some embodiments, the recombinant microorganism further produces 1-propanol. In some embodiments, the conditions comprise anaerobic conditions. In some embodiments, the conditions comprise microaerobic conditions.

The present disclosure provides a method of co-producing 2,4-FDCA and ethanol in a recombinant microorganism comprising: (a) converting glyceraldehyde 3-phosphate (G3P) to 4-hydroxymethylfurfural phosphate; (b) converting 4-hydroxymethylfurfural phosphate to 4-hydroxymethylfurfural (4-HMF); (c) converting 4-HMF to 2,4-furandicarboxylic acid (2,4-FDCA), either directly or through production of one or more intermediates; (d) converting ribulose-5-phosphate to ribulose-1,5-bisphosphate; and (e) converting $CO_2$ and ribulose-1,5-bisphosphate to two molecules of glycerate-3-phosphate. In some embodiments, the method further comprises converting NADH and/or NADPH produced as a byproduct of 2,4-FDCA production and glycerate-3-phosphate to ethanol. In some embodiments, glyceraldehyde 3-phosphate (G3P) is converted to 4-hydroxymethylfurfural phosphate with a methyl phosphate synthase; 4-hydroxymethylfurfural phosphate is converted to 4-hydroxymethylfurfural (4-HMF) with a phosphatase or a kinase; ribulose-5-phosphate is converted to ribulose-1,5-bisphosphate with a phosphoribulokinase; and $CO_2$ and ribulose-1,5-bisphosphate are converted to two molecules of glycerate-3-phosphate with a RuBisCO.

The present disclosure provides a method of co-producing 2,4-FDCA, 1-propanol, and ethanol in a recombinant microorganism comprising: (a) converting glyceraldehyde 3-phosphate (G3P) to 4-hydroxymethylfurfural phosphate; (b) converting 4-hydroxymethylfurfural phosphate to 4-hydroxymethylfurfural (4-HMF); (c) converting 4-HMF to 2,4-furandicarboxylic acid (2,4-FDCA), either directly or through production of intermediates; (d) converting phosphoenol pyruvate (PEP) to oxaloacetate; (e) converting oxaloacetate to malonate semialdehyde; and/or converting oxaloacetate to aspartate, aspartate to β-alanine, and β-alanine to malonate semialdehyde; (f) converting malonate semialdehyde to 3-hydroxypropionic acid (3-HP); (g) converting 3-HP to propionyl-CoA; and (h) converting propionyl-CoA to 1-propanol; and/or converting propionyl-CoA to propionaldehyde and propionaldehyde to 1-propanol. In some embodiments, the method further comprises converting NADH and/or NADPH produced as a byproduct of 2,4-FDCA production to ethanol. In some embodiments, glyceraldehyde 3-phosphate (G3P) is converted to 4-hydroxymethylfurfural phosphate with a methyl phosphate synthase; 4-hydroxymethylfurfural phosphate is converted to 4-hydroxymethylfurfural (4-HMF) with a phosphatase or a kinase; phosphoenol pyruvate (PEP) is converted to oxaloacetate with a phosphoenol pyruvate carboxylase and/or a phosphoenol pyruvate carboxykinase; oxaloacetate is converted to asparate with an aspartate amino transferase; aspartate is converted to β-alanine with an aspartate decarboxylase; β-alanine is converted to malonate semialdehyde with a β-alanine pyruvate amino transferase and/or a β-alanine transaminase; malonate semialdehyde is converted to 3-hydroxypropionic acid (3-HP) with a 3-hydroxypropionic acid dehydrogenase; 3-HP is converted to propionyl-CoA with a propionyl-CoA synthase, and/or 3-HP is converted to propionyl-CoA with a 3-hydroxypropionyl-CoA synthetase/transferase, a 3-hydroxypropionyl-CoA dehydratase, and an acrylyl-CoA reductase; and propionyl-CoA is converted to 1-propanol with an alcohol/aldehyde dehydrogenase, and/or propionyl-CoA is converted to propionaldehyde with an aldehyde dehydrogenase (acetylating) and propionaldehyde is converted to 1-propanol with an alcohol dehydrogenase.

The present disclosure provides a method of producing a recombinant microorganism capable of producing 2,4-FDCA, the method comprising introducing into and/or overexpressing in the recombinant microorganism the following: (a) at least one nucleic acid molecule encoding a polypeptide that catalyzes the production of 4-hydroxymethylfurfural phosphate from glyceraldehyde 3-phosphate (G3P); (b) at least one nucleic acid molecule encoding a polypeptide that catalyzes the production of 4-hydroxymethylfurfural (4-HMF) from 4-hydroxymethylfurfural phosphate; (c) at least one nucleic acid molecule encoding one or more polypeptides that catalyze the production of 2,4-furandicarboxylic acid (2,4-FDCA) from 4-HMF, either directly or through production of intermediates, wherein the intermediates are preferably furan-2,4-dicarbaldehyde, 4-(hydroxymethyl)furoic acid, 4-formylfuran-2-carboxylate, 4-formylfuran-2-carboxylate, and/or 2-formylfuran-4-carboxylate; (d) at least one nucleic acid molecule encoding a polypeptide that catalyzes the production of ribulose-1,5-bisphosphate from ribulose-5-phosphate; and (e) at least one nucleic acid molecule encoding a polypeptide that catalyzes the production of two molecules of glycerate-3-phosphate from the combination of $CO_2$ with ribulose-1,5-bisphosphate.

The present disclosure provides a method of producing a recombinant microorganism capable of producing 2,4-FDCA, the method comprising introducing into and/or overexpressing in the recombinant microorganism the following: (a) at least one nucleic acid molecule encoding a polypeptide that catalyzes the production of 4-hydroxymethylfurfural phosphate from glyceraldehyde 3-phosphate (G3P); (b) at least one nucleic acid molecule encoding a polypeptide that catalyzes the production of 4-hydroxymethylfurfural (4-HMF) from 4-hydroxymethylfurfural phosphate; (c) at least one nucleic acid molecule encoding one or more polypeptides that catalyze the production of 2,4-furandicarboxylic acid (2,4-FDCA) from 4-HMF, either directly or through production of intermediates, wherein the intermediates are preferably furan-2,4-dicarbaldehyde, 4-(hydroxymethyl)furoic acid, 4-formylfuran-2-carboxylate, 4-formylfuran-2-carboxylate, and/or 2-formylfuran-4-carboxylate; (d) at least one nucleic acid molecule encoding a polypeptide that catalyzes the production of acetyl phosphate and D-glyceraldehyde-3-phosphate from D-xylulose-5-phosphate and phosphate, and/or at least one nucleic acid molecule encoding a polypeptide that catalyzes the production of acetyl phosphate and erythrose-4-phosphate from fructose-6-phosphate and phosphate; (e) at least one nucleic acid molecule encoding one or more polypeptides that catalyze: (1) the production of acetyl-CoA from acetyl phosphate and free coenzyme A; and/or (2) the production of acetate from acetyl phosphate and the production of acetyl-CoA from acetate; and (f) at least one nucleic acid molecule encoding one or more polypeptides that catalyze: (1) the production of acetaldehyde from acetyl-CoA, and/or the production of ethanol from acetaldehyde; and/or (2) the production of ethanol from acetyl-CoA.

The present disclosure provides a method of producing a recombinant microorganism capable of producing 2,4-FDCA, the method comprising introducing into and/or overexpressing in the recombinant microorganism the following: (a) at least one nucleic acid molecule encoding a polypeptide that catalyzes the production of 4-hydroxymethylfurfural phosphate from glyceraldehyde 3-phosphate (G3P); (b) at least one nucleic acid molecule encoding a polypeptide that catalyzes the production of 4-hydroxymethylfurfural (4-HMF) from 4-hydroxymethylfurfural phosphate; (c) at least one nucleic acid molecule encoding one or more polypeptides that catalyze the production of 2,4-furandicarboxylic acid (2,4-FDCA) from 4-HMF, either directly or through production of intermediates, wherein the intermediates are preferably furan-2,4-dicarbaldehyde, 4-(hydroxymethyl)furoic acid, 4-formylfuran-2-carboxylate, 4-formylfuran-2-carboxylate, and/or 2-formylfuran-4-carboxylate; (d) at least one nucleic acid molecule encoding a polypeptide that catalyzes the production of oxaloacetate from phosphoenol pyruvate (PEP); (e) at least one nucleic acid molecule encoding one or more polypeptides that catalyze: (1) the production of malonate semialdehyde from oxaloacetate; and/or (2) the production of aspartate from oxaloacetate, the production of β-alanine from aspartate, and the production of malonate semialdehyde from β-alanine; (f) at least one nucleic acid molecule encoding a polypeptide that catalyzes the production of 3-hydroxypropionic acid (3-HP) from malonate semialdehyde; (g) at least one nucleic acid molecule encoding one or more polypeptides that catalyze the production of propionyl-CoA from 3-HP; and (h) at least one nucleic acid molecule encoding a polypeptide that catalyzes the production of 1-propanol from propionyl-CoA; and/or at least one nucleic acid molecule encoding one or more polypeptides that catalyze the production of propionaldehyde from propionyl-CoA and the production of 1-propanol from propionaldehyde.

The present disclosure provides a method of producing a polymer from 2,4-FDCA produced by the microorganism as disclosed herein, wherein the 2,4-FDCA and a diol are catalytically polymerized in a non-biological process. In some embodiments, the diol is selected from ethylene glycol, 1,3-propanediol, 1,2-propanediol, 1,4-butanediol, 1,3-butanediol, 2,3-butanediol, 1,5-pentanediol, or 1,6-hexanediol.

DETAILED DESCRIPTION

Figure 1:
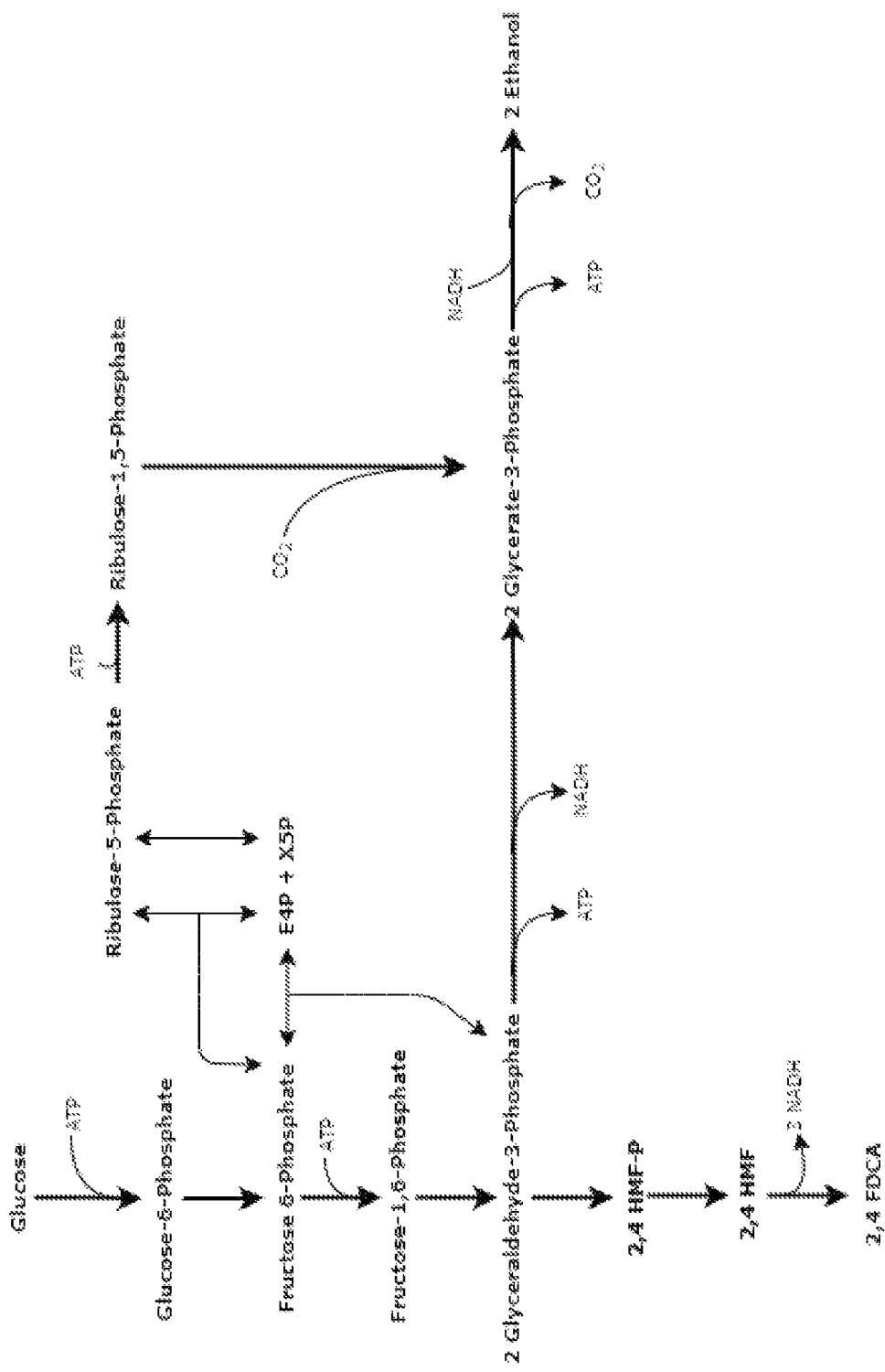
FIG. 1 is a schematic overview of a biosynthetic pathway utilized by recombinant microorganisms of the disclosure for 2,4-FDCA and ethanol production.

The present disclosure provides a direct and anaerobic fermentation route to 2,4-FDCA in a recombinant microorganism. The direct and anaerobic fermentation of 2,4-FDCA from a carbon feedstock enables the production of novel chemicals, solvents and polymers with commercial applicability on an industrial scale. By utilizing the anaerobic pathways disclosed herein, more efficient and cost-effective 2,4-FDCA production can be achieved compared to an aerobic pathway.

Fermentative production of 2,4-FDCA from a carbon feedstock can be achieved by a pathway involving conversion of glyceraldehyde-3-phosphate (G3P) into (5-formylfuran-3-yl)methyl phosphate, conversion of (5-formylfuran-3-yl)methyl phosphate into 4-hydroxymethylfurfural (4-HMF), and oxidation of 4-HMF into 2,4-FDCA by oxidases or by dehydrogenases, directly or through the intermediates selected from furan-2,4-dicarbaldehyde, 4-(hydroxymethyl)furoic acid, 4-formylfuran-2-carboxylate, 4-formylfuran-2-carboxylate, and/or 2-formylfuran-4-carboxylate. The foregoing pathway is net ATP negative (negative two molecules of ATP per one molecule of 2,4-FDCA) and requires electron acceptors for 4-HMF oxidation to 2,4-FDCA. When oxidases are used, oxygen is utilized as the electron acceptor and three molecules of O2 are reduced to three molecules of $H_2O_2$. When dehydrogenases are used, $NADP^+$ (or $NAD^+$) is utilized as the electron acceptor and three molecules of NADPH (or NADH) are produced per molecule of 2,4-FDCA. The pathway for 2,4-FDCA production discussed above is both ATP negative and NADH positive according to equation 1:

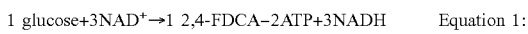

$$1\ glucose+3NAD^+ \rightarrow 1\ 2,4\text{-FDCA}-2ATP+3NADH \quad \text{Equation 1:}$$

Redox-cofactor balance and positive ATP yields are key requirements for viable anaerobic fermentation processes. Thus, microorganisms that are unable to provide redox-cofactor balance among different metabolic pathways and/or that lack positive ATP yields typically demonstrate poor or no ability to grow under anaerobic fermentation conditions.

As an example, glycerol is a well described required end-product of yeast ethanolic fermentation due to its redox imbalance in anaerobic fermentations. During anaerobic growth on carbohydrates, glycerol production functions as an electron sink to offset cell biomass formation so that overall redox neutrality is conserved (i.e., NAD+ is reduced to NADH at biomass formation and NADH is oxidized to NAD+ by glycerol production). While this is essential from a theoretical consideration of conservation of mass, in practice this has the effect that strains unable to produce glycerol (i.e., unable to use glycerol production as electron sink) are unable (or only very poorly able) to grow under the anaerobic conditions industrially used for ethanol production. Under anaerobic conditions, glycerol typically accounts for 4-10% of the total sugar consumption.

The present disclosure provides a recombinant ethanol-producing yeast capable of producing 2,4-furandicarboxylic acid (2,4-FDCA) and ethanol from a carbon source, wherein the production of glycerol, a low value chemical, is partially or completely replaced by 2,4-FDCA. Therefore, the present disclosure provides redox-cofactor balanced and positive ATP-yielding coupled pathways for anaerobic production of 2,4-FDCA and high value chemicals such as ethanol. Thus, the present disclosure provides pathways and microorganisms where the 2,4-FDCA pathway is coupled with electron consuming pathways (for redox balance) and with the canonical ethanol production pathway in yeast for ATP surplus (equation 2), enabling an anaerobic high yield production of 2,4-FDCA and high value chemicals:

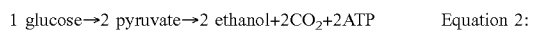

1 glucose→2 pyruvate→2 ethanol+2CO$_2$+2ATP  Equation 2:

Definitions

The following definitions and abbreviations are to be used for the interpretation of the disclosure.

As used herein and in the appended claims, the singular forms "a," "an," and "the" include plural referents unless the context clearly dictates otherwise. Thus, for example, reference to "an enzyme" includes a plurality of such enzymes and reference to "the microorganism" includes reference to one or more microorganisms, and so forth.

As used herein, the terms "comprises," "comprising," "includes," "including," "has," "having, "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, or, in some embodiments, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

As used herein, the terms "microbial," "microbial organism," and "microorganism" include any organism that exists as a microscopic cell that is included within the domains of archaea, bacteria or eukarya, the latter including yeast and filamentous fungi, protozoa, algae, or higher Protista. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical.

As described herein, in some embodiments, the recombinant microorganism is a eukaryotic microorganism. In some embodiments, the eukaryotic microorganism is a yeast. In some embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Torulaspora, Rhodotorula, Scheffersomyces* and *Myxozyma*.

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. It is understood that the terms "recombinant microorganism" and "recombinant host cell" refer not only to the particular recombinant microorganism but to the progeny or potential progeny of such a microorganism.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. See Sambrook et al., 1989, supra.

The term "decreasing" or "reducing" the level of expression of a gene or an enzyme activity refers to the partial or complete suppression of the expression of a gene or enzyme activity. This suppression of expression or activity can be either an inhibition of the expression of the gene, a deletion of all or part of the promoter region necessary for the gene expression, a deletion in the coding region of the gene, or the replacement of the wild-type promoter by a weaker natural or synthetic promoter. For example, a gene may be completely deleted and may be replaced by a selection marker gene that facilitates the identification, isolation and purification of the strains according to the present disclosure. Alternatively, endogenous genes may be knocked out or deleted to favor the new metabolic pathway. In yet another embodiment, the expression of the gene may be decreased or reduced by using a weak promoter or by introducing certain mutations.

As used herein, the term "non-naturally occurring," when used in reference to a microorganism or enzyme activity of the disclosure, is intended to mean that the microorganism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microorganism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s) such that the molecule differing in nucleotide or amino acid sequence from the endogenous nucleotide or amino acid as found endogenously is produced in an unnatural (e.g., greater than naturally found) amount in the cell.

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution. The terms "homologous sequences" or "homologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Mich.), AlignX, and Vector NTI (Invitrogen, Carlsbad, Calif.). A similar biological function may include, but is not limited to: catalyzing the same or similar enzymatic reaction; having the same or similar selectivity for a substrate or co-factor; having the same or similar stability; having the same or similar tolerance to various fermentation conditions (temperature, pH, etc.); and/or having the same or similar tolerance to various metabolic substrates, products, by-products, intermediates, etc. The degree of similarity in biological function may vary, but in one embodiment, is at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%, according to one or more assays known to one skilled in the art to determine a given biological function.

The term "variant" refers to any polypeptide or enzyme described herein. A variant also encompasses one or more components of a multimer, multimers comprising an individual component, multimers comprising multiples of an individual component (e.g., multimers of a reference molecule), a chemical breakdown product, and a biological breakdown product. In particular, non-limiting embodiments, an enzyme may be a "variant" relative to a reference enzyme by virtue of alteration(s) in any part of the polypeptide sequence encoding the reference enzyme. A variant of a reference enzyme can have enzyme activity of at least 10%, at least 30%, at least 50%, at least 80%, at least 90%, at least 100%, at least 105%, at least 110%, at least 120%, at least 130% or more in a standard assay used to measure enzyme activity of a preparation of the reference enzyme. In some embodiments, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the full-length, or unprocessed enzymes of the present disclosure. In some embodiments, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the mature, or processed enzymes of the present disclosure.

The term "yield potential" or as used herein refers to a yield of a product from a biosynthetic pathway. In one embodiment, the yield potential may be expressed as a percent by weight of end product per weight of starting compound.

The term "thermodynamic maximum yield" as used herein refers to the maximum yield of a product obtained from fermentation of a given feedstock, such as glucose, based on the energetic value of the product compared to the feedstock. In a normal fermentation, without use of additional energy sources such as light, hydrogen gas or methane or electricity, for instance, the product cannot contain more energy than the feedstock. The thermodynamic maximum yield signifies a product yield at which all energy and mass from the feedstock is converted to the product. This yield can be calculated and is independent of a specific pathway. If a specific pathway towards a product has a lower yield than the thermodynamic maximum yield, then it loses mass and can most likely be improved upon or substituted with a more efficient pathway towards the product.

The term "redox balance" refers to the overall amount of redox cofactors in a given set of reactions. When there is a shortage of redox cofactors, the redox balance is negative and the yield of such pathway would not be realistic since there is a need to burn feedstock to fulfill the cofactor demand. When there is a surplus of redox cofactors, the redox balance is said to be positive and the yield of such pathway is lower than the maximum yield (Dugar et al. "Relative potential of biosynthetic pathways for biofuels and bio-based products" Nature biotechnology 29.12 (2011): 1074). In addition, when the pathway produces the same amount of redox cofactors as it consumes, the redox balance is zero and one can refer to this pathway as "redox balanced." Designing metabolic pathways and engineering an organism such that the redox cofactors are balanced or close to being balanced usually results in a more efficient, higher yield production of the desired compounds when compared to an unbalanced pathway. Redox reactions occur together as two half-reactions happening simultaneously, one being an oxidation reaction and the other a reduction reaction. In redox processes, the reductant transfers electrons to the oxidant. Thus, in the reaction, the reductant or reducing agent loses electrons and is oxidized, and the oxidant or oxidizing agent gains electrons and is reduced. In one embodiment, the redox reactions take place in a biological system. The term redox state is often used to describe the balance of NAD+/NADH and NADP+/NADPH of natural or non-natural metabolic pathways in a biological system such as a microbial cell. The redox state is reflected in the balance of several sets of metabolites (e.g., lactate and pyruvate, beta-hydroxybutyrate, and acetoacetate), whose interconversion is dependent on these ratios. In one embodiment, an external source of hydrogen or electrons, combined or not with the use of hydrogenase enzymes able to convert hydrogen to NAD(P)H, may be beneficial to increase product yield in metabolic pathways with negative redox balance, i.e., when there is a shortage in redox cofactors, such as NAD(P)H.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

The term "biologically pure culture" or "substantially pure culture" refers to a culture of a bacterial species described herein containing no other bacterial species in quantities sufficient to interfere with the replication of the culture or be detected by normal bacteriological techniques.

As used herein, a "control sequence" refers to an operator, promoter, silencer, or terminator.

As used herein, "introduced" refers to the introduction by means of modern biotechnology, and not a naturally occurring introduction.

As used herein, a "constitutive promoter" is a promoter, which is active under most conditions and/or during most development stages. There are several advantages to using constitutive promoters in expression vectors used in biotechnology, such as: high level of production of proteins used to select transgenic cells or organisms; high level of expression of reporter proteins or scorable markers, allowing easy detection and quantification; high level of production of a transcription factor that is part of a regulatory transcription system; production of compounds that requires ubiquitous activity in the organism; and production of compounds that are required during all stages of development.

As used herein, a "non-constitutive promoter" is a promoter which is active under certain conditions, in certain types of cells, and/or during certain development stages. For example, inducible promoters, and promoters under development control are non-constitutive promoters.

As used herein, "inducible" or "repressible" promoter is a promoter which is under chemical or environmental factors control. Examples of environmental conditions that may affect transcription by inducible promoters include anaerobic conditions, certain chemicals, the presence of light, acidic or basic conditions, etc.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

The term "catalytically polymerized" as used herein refers to polymerization process wherein monomers of the disclosure are polymerized in a non-biological or non-in vivo context.

The term "signal sequence" as used herein refers to an amino acid sequence that targets peptides and polypeptides to cellular locations or to the extracellular environment. Signal sequences are typically at the N-terminal portion of a polypeptide and are typically removed enzymatically. Polypeptides that have their signal sequences are referred to as being full-length and/or unprocessed. Polypeptides that have had their signal sequences removed are referred to as being mature and/or processed.

As used herein, "microbial composition" refers to a composition comprising one or more microbes of the present disclosure.

As used herein, "carrier," "acceptable carrier," "commercially acceptable carrier," or "industrial acceptable carrier" refers to a diluent, adjuvant, excipient, or vehicle with which the microbe can be administered, stored, or transferred, which does not detrimentally effect the microbe.

As used herein, the term "productivity" refers to the total amount of bioproduct, such as (2,4-FDCA), produced per hour.

As used herein, "anaerobic conditions" when used in reference to a culture or growth condition is intended to mean that the amount of oxygen is less than about 0% saturation of dissolved oxygen in liquid media. The term is also intended to include sealed chambers of liquid or solid media maintained with an atmosphere of less than about 0% oxygen. Anaerobic conditions include conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism consuming the available oxygen of fermentation until oxygen is unavailable to the microorganism as a terminal electron acceptor.

As used herein, the term "aerobic" when used in reference to a culture or growth condition is intended to mean that the amount of oxygen is greater than about 10% of saturation for dissolved oxygen in liquid media. The term is also intended to include sealed chambers of liquid or solid media maintained with an atmosphere of about 10% oxygen to about 21% oxygen (as found in the atmosphere at sea level).

As used herein, the term "microaerobic" when used in reference to a culture or growth condition is intended to mean that the amount of oxygen is present in subsaturating amounts between anaerobic and aerobic conditions, wherein aerophilic microorganisms are capable of being sustained without an anoxic die off of the aerophilic microorganisms, the term "microaerobic" when used in reference to a culture or growth condition is intended to mean that the amount of oxygen is between 0% and 10% of saturation for dissolved oxygen in liquid media. The term is also intended to include sealed chambers of liquid or solid media maintained within a flow of oxygen that is utilized at about the same rate as it is provided without achieving aerobic conditions.

Recombinant Microorganisms

In some embodiments, the present disclosure provides a recombinant yeast capable of anaerobically co-producing 2,4-FDCA and ethanol, by replacing glycerol formation as the predominant redox sink in anaerobic yeast metabolism with 2,4-FDCA production. In some embodiments, the present disclosure provides a recombinant microorganism capable of anaerobically co-producing 2,4-FDCA, ethanol, and 1-propanol.

In some embodiments, the recombinant microorganism converts a carbon source to glyceraldehyde 3-phosphate (G3P). G3P is a common natural intermediary metabolite. In some embodiments, G3P can be produced from glucose via the glycolysis pathway or from xylose (e.g., from the pentose phosphate pathway) or from glycerol. In some embodiments, the recombinant microorganism capable of anaerobically producing 2,4-FDCA utilizes a carbon source that comprises a monosaccharide (e.g., a hexose or a pentose), or glycerol. In some embodiments, the recombinant microorganism comprises the capacity to anaerobically convert G3P to 2,4-FDCA via several enzymatically-catalyzed successive steps.

In some embodiments, the recombinant microorganisms of the present disclosure are fungi.

In some embodiments, the recombinant microorganism is a eukaryotic microorganism. In some embodiments, the eukaryotic microorganism is a yeast. In some embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Torulaspora, Rhodotorula, Scheffersomyces* and *Myxozyma*. In some embodiments, the yeast is selected from *Saccharomyces* spp, *Saccharomyces cerevisiae, Issatchenkia* spp., *Hansenula* spp., *Debaryomyces* spp., *Rhodotula* spp., *Pachysolen* spp., *Cryptococcus* spp., *Trichosporon* spp., *Myxozyma* spp., *Candida* spp., *Kluyveromyces* spp., *Pichia* spp., *Schizosaccharomyces* spp., *Torulaspora* spp., *Zygosaccharomyces* spp., *Yarrowia* spp., *Yarrowia lipolytica, Scheffersomyces* spp. or *Scheffersomyces stipites*.

4-HMF

In some embodiments, the present disclosure comprises recombinant microorganisms and related methods for: (1) converting one or more carbon sources to glyceraldehyde 3-phosphate (G3P); (2) converting G3P to (5-formylfuran-3-yl)methyl phosphate (also known as 4-hydroxymethylfurfural phosphate); and (3) converting (5-formylfuran-3-yl) methyl phosphate to 4-hydroxymethylfurfural (4-HMF). In some embodiments, the one or more carbon sources are selected from glycerol, a monosaccharide, or a combination thereof.

In some embodiments, the recombinant microorganism of any one of the embodiments disclosed herein comprises at least one endogenous and/or exogenous nucleic acid molecule encoding one or more polypeptides capable of converting a carbon source to glyceraldehyde 3-phosphate (G3P). In some embodiments, glycerol is converted to glycerol-3-phosphate by at least one endogenous or exogenous glycerol kinase. In some embodiments, glycerol-3-phosphate is converted to dihydroxyacetone phosphate (DHAP) by at least one endogenous or exogenous glycerol-3-phosphate dehydrogenase. In some embodiments, glycerol is converted to dihydroxyacetone by at least one endogenous or exogenous glycerol dehydrogenase. In some embodiments, dihydroxyacetone is converted to dihydroxyacetone phosphate (DHAP) by at least one endogenous or exogenous dihydroxyacetone kinase. In some embodiments, DHAP is converted to G3P by at least one endogenous or exogenous triose phosphate isomerase. See Zhang et al. (2010. Applied and Environmental Microbiology, 76.8:2397-2401) for exemplary, but non-limiting, glycerol assimilation pathways contemplated herein.

In some embodiments, the recombinant microorganism of any one of the embodiments of disclosed herein comprises at least one endogenous or exogenous nucleic acid molecule encoding a (5-formylfuran-3-yl)methyl phosphate synthase that catalyzes the conversion of G3P to (5-formylfuran-3-yl)methyl phosphate. In some embodiments, the (5-formylfuran-3-yl)methyl phosphate synthase is classified as EC number 4.2.3.153. In some embodiments the EC 4.2.3.153 (5-formylfuran-3-yl)methyl phosphate synthase can be derived from the gene mfnB. In some embodiments, mfnB can be derived from *Methanocaldococcus jannaschii*. In some embodiments, EC 4.2.3.153 can be derived from homologs of mfnB.

In some embodiments, the recombinant microorganism of any one of the embodiments disclosed herein comprises at least one endogenous or exogenous nucleic acid molecule encoding a phosphatase or a kinase that catalyzes the conversion of (5-formylfuran-3-yl)methyl phosphate to (4-HMF). In some embodiments, the phosphatase is classified as EC number 3.1.3. In some embodiments, the phosphatase EC number 3.1.3 is selected from alkaline phosphatase (EC number 3.1.3.1), acid phosphatase (EC number 3.1.3.2), fructose-bisphosphatase (EC number 3.1.3.11), sugar-phosphatase (EC number 3.1.3.23), or sugar-terminal-phosphatase (EC number 3.1.3.58). In some embodiments, the kinase is classified as EC number 2.7.1. In some embodiments, the kinase EC number 2.7.1 is selected from fructokinase (EC number 2.7.1.4), ribokinase (EC number 2.7.1.15), ribulokinase (EC number 2.7.1.16), xylulokinase (EC number 2.7.1.17), or D-ribulokinase (EC number 2.7.1.47).

Thus, in some embodiments, the recombinant microorganism comprises at least one endogenous and/or exogenous nucleic acid molecule encoding polypeptides capable of converting a carbon source to glyceraldehyde 3-phosphate (G3P); at least one endogenous or exogenous nucleic acid molecule encoding a (5-formylfuran-3-yl)methyl phosphate synthase that catalyzes the conversion of G3P to (5-formylfuran-3-yl)methyl phosphate; and at least one endogenous or exogenous nucleic acid molecule encoding a phosphatase or a kinase that catalyzes the conversion of (5-formylfuran-3-yl)methyl phosphate to 4-HMF. Additional suitable enzymes for converting a carbon source to G3P, G3P to (5-formylfuran-3-yl)methyl phosphate, and (5-formylfuran-3-yl)methyl phosphate to 4-hydroxymethylfurfural (4-HMF) are disclosed in U.S. Patent Application Publication No. 2020/0277639.

2,4-FDCA

In some embodiments, the present disclosure comprises recombinant microorganisms and related methods for converting one or more carbon sources to 2,4-furandicarboxylic acid (2,4-FDCA).

In some embodiments, the recombinant microorganism of any one of the embodiments disclosed herein comprises at least one endogenous and/or exogenous nucleic acid molecule encoding one or more polypeptides capable of converting G3P to 2,4-FDCA via several enzymatically-catalyzed successive steps as described herein. In some embodiments, the recombinant microorganism of any one of the embodiments disclosed herein comprises at least one endogenous and/or exogenous nucleic acid molecule encoding one or more polypeptides capable of converting 4-HMF, either directly or via several enzymatically-catalyzed successive steps as described herein, to 2,4-FDCA.

In some embodiments, the recombinant microorganism of any one of the embodiments disclosed herein comprises at least one endogenous and/or exogenous nucleic acid molecule encoding one or more polypeptides capable of: (1) converting 4-HMF to furan-2,4-dicarbaldehyde and/or 4-(hydroxymethyl)furoic acid; (2) converting furan-2,4-dicarbaldehyde to 4-formylfuran-2-carboxylate and/or 2-formylfuran-4-carboxylate and/or converting 4-(hydroxymethyl)furoic acid to 4-formylfuran-2-carboxylate; and/or (3) converting 4-formylfuran-2-carboxylate to 2,4-FDCA and/or converting 2-formylfuran-4-carboxylate to 2,4-FDCA.

In some embodiments, the recombinant microorganism comprises: (1) at least one endogenous or exogenous nucleic acid molecule encoding a dehydrogenase, an oxidase, or a peroxygenase that catalyzes the conversion of 4-HMF to furan-2,4-dicarbaldehyde and/or 4-(hydroxymethyl)furoic acid; (2) at least one endogenous or exogenous nucleic acid molecule encoding a dehydrogenase, an oxidase, or a peroxygenase that catalyzes the conversion of furan-2,4-dicarbaldehyde to 4-formylfuran-2-carboxylate and/or 2-formylfuran-4-carboxylate and/or the conversion of 4-(hydroxymethyl)furoic acid to 4-formylfuran-2-carboxylate; and/or (3) at least one endogenous or exogenous nucleic acid molecule encoding a dehydrogenase, an oxidase, or a peroxygenase that catalyzes the conversion of 2-formylfuran-4-carboxylate to 2,4-FDCA and/or 4-formylfuran-2-carboxylate to 2,4-FDCA. See U.S. patent application Ser. No. 16/806,728, which is hereby incorporated by reference in its entirety, WO2011026913, WO2017050815, and WO2016133384. See also Koopman et al. (2010. Efficient Whole-Cell Biotransformation of 5-(hydroxymethyl) furfural into FDCA, 2,5-furandicarboxylic acid. *Bioresource Technology*, 101(16):6291-6296), Hossain et al. (2016. Metabolic Engineering of *Raoultella ornithinolytica* BF60 for the production of 2,5-furandicarboxylic acid from 5-hydroxymethylfurfural. *Applied and Environmental Microbiology*, AEM-02312), and Carro et al. (2015. 5-hydroxymethylfurfural conversion by fungal aryl-alcohol oxidase and unspecific peroxygenase. *The FEBS Journal*, 128(16):3218-3229).

In some embodiments, the recombinant microorganism of any one of the embodiments disclosed herein comprises at least one endogenous or exogenous nucleic acid molecule encoding a dehydrogenase, an oxidase, or a peroxygenase that catalyzes the conversion of 4-HMF to furan-2,4-dicarbaldehyde. In some embodiments, the dehydrogenase is classified as EC number 1.1.1. In some embodiments, the dehydrogenase EC number 1.1.1 selected from alcohol dehydrogenase (EC number 1.1.1.1), or alcohol dehydrogenase (NADP+) (EC number 1.1.1.2), or D-xylose reductase (EC number 1.1.1.307), or aryl-alcohol dehydrogenase (EC number 1.1.1.90), or an aryl-alcohol dehydrogenase (NADP+) (EC number 1.1.1.91). In some embodiments, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from Methylovorus sp. MP688 or *Cupriavidus basilensis*. See Dijkman and Fraaije (2014. Applied Environmental Microbiology, 80.3:1082-1090) and Koopman et al. (2010. PNAS, 107(11):4919-4924). In some embodiments, the oxidase EC number 1.1.3 is aryl-alcohol oxidase (EC number 1.1.3.7). See Carro et al. (2015). In some embodiments, the peroxygenase is classified as EC number 1.11.2. In some embodiments, the peroxygenase EC number 1.11.2 is unspecific peroxygenase (EC number 1.11.2.1). See Carro et al. (2015).

In some embodiments, the recombinant microorganism of any one of the embodiments disclosed herein comprises at least one endogenous or exogenous nucleic acid molecule encoding a dehydrogenase, or an oxidase, or a peroxygenase that catalyzes the conversion of 4-HMF to 4-(hydroxymethyl)furoic acid. In some embodiments, the dehydrogenase is classified as EC number 1.2.1. In one embodiment, the dehydrogenase EC number 1.2.1 selected from an aldehyde dehydrogenase (NAD+) (EC number 1.2.1.3) or aldehyde dehydrogenase (NADP+) (EC number 1.2.1.4) or aldehyde dehydrogenase [NAD(P)+] (EC number 1.2.1.5) or 4-(γ-glutamylamino)butanal dehydrogenase (EC number 1.2.1.99). In some embodiments, the oxidase is classified as EC number 1.1.3. In some embodiments, the oxidase EC number 1.1.3 is a 5-(hydroxymethylfurfural oxidase (EC number 1.1.3.47). In some embodiments the EC 1.1.3.47 oxidase can be derived from the gene hmfH. In some embodiments, hmfH can be derived from Methylovorus sp. MP688 or *Cupriavidus basilensis*. In some embodiments, the oxidase EC number 1.1.3 is aryl-alcohol oxidase (EC number 1.1.3.7). In some embodiments, the peroxygenase is classified as EC number 1.11.2. In some embodiments, the peroxygenase EC number 1.11.2 is unspecific peroxygenase (EC number 1.11.2.1).

In some embodiments, the recombinant microorganism of any one of the embodiments disclosed herein comprises at least one endogenous or exogenous nucleic acid molecule encoding a dehydrogenase, or a oxidase, or a peroxygenase that catalyzes the conversion of furan-2,4-dicarbaldehyde to 4-formylfuran-2-carboxylate and/or to 2-formylfuran-4-carboxylate. In some embodiments, the dehydrogenase is classified as EC number 1.2.1. In some embodiments, the dehydrogenase EC number 1.2.1 selected from aldehyde dehydrogenase (NAD+) (EC number 1.2.1.3) or aldehyde dehydrogenase (NADP+) (EC number 1.2.1.4) or aldehyde dehydrogenase [NAD(P)+] (EC number 1.2.1.5) or 4-(γ-glutamylamino)butanal dehydrogenase (EC number 1.2.1.99). In some embodiments, the oxidase is classified as EC number 1.1.3. In some embodiments, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from Methylovorus sp. MP688 or *Cupriavidus basilensis*. In some embodiments, the oxidase EC number 1.1.3 is aryl-alcohol oxidase (EC number 1.1.3.7). In some embodiments, the peroxygenase is classified as EC number 1.11.2. In some embodiments, the peroxygenase EC number 1.11.2 is unspecific peroxygenase (EC number 1.11.2.1).

In some embodiments, the recombinant microorganism of any one of the embodiments disclosed herein comprises at least one endogenous or exogenous nucleic acid molecule encoding a dehydrogenase, or a oxidase, or a peroxygenase that catalyzes the conversion of 4-(hydroxymethyl)furoic acid to 4-formylfuran-2-carboxylate. In some embodiments, the dehydrogenase is classified as EC number 1.1.1. In some embodiments, the dehydrogenase EC number 1.1.1 selected from alcohol dehydrogenase (EC number 1.1.1.1), or alcohol dehydrogenase (NADP+) (EC number 1.1.1.2), or D-xylose reductase (EC number 1.1.1.307), or aryl-alcohol dehydrogenase (EC number 1.1.1.90), or aryl-alcohol dehydrogenase (NADP+) (EC number 1.1.1.91). In some embodiments, the oxidase is classified as EC number 1.1.3. In some embodiments, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from Methylovorus sp. MP688 or *Cupriavidus basilensis*. In some embodiments, the oxidase EC number 1.1.3 is aryl-alcohol oxidase (EC number 1.1.3.7). In some embodiments, the peroxygenase is classified as EC number 1.11.2. In some embodiments, the peroxygenase EC number 1.11.2 is unspecific peroxygenase (EC number 1.11.2.1).

In some embodiments, the recombinant microorganism of any one of the embodiments disclosed herein comprises at least one endogenous or exogenous nucleic acid molecule encoding a dehydrogenase, or a oxidase, or a peroxygenase that catalyzes the conversion of 4-formylfuran-2-carboxylate and/or 2-formylfuran-4-carboxylate to 2,4-FDCA. In some embodiments, the dehydrogenase is classified as EC number 1.2.1. In some embodiments, the dehydrogenase EC number 1.2.1 selected from aldehyde dehydrogenase (NAD+) (EC number 1.2.1.3) or aldehyde dehydrogenase (NADP+) (EC number 1.2.1.4) or aldehyde dehydrogenase [NAD(P)+] (EC number 1.2.1.5) or 4-(γ-glutamylamino)butanal dehydrogenase (EC number 1.2.1.99). In some embodiments, the oxidase is classified as EC number 1.1.3. In some embodiments, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from Methylovorus sp. MP688 or *Cupriavidus basilensis*. In some embodiments, the oxidase EC number 1.1.3 is aryl-alcohol oxidase (EC number 1.1.3.7). In some embodiments, the peroxygenase is classified as EC number 1.11.2. In some embodiments, the peroxygenase EC number 1.11.2 is unspecific peroxygenase (EC number 1.11.2.1).

Coupling 2,4-FDCA Production with Calvin Cycle Enzymes

In some embodiments, the present disclosure comprises recombinant microorganisms and related methods for anaerobically converting one or more carbon sources to 2,4-furandicarboxylic acid (2,4-FDCA) and ethanol.

In some embodiments, the 2,4-FDCA pathway disclosed herein is coupled to electron consuming pathways to provide redox balance and with an ethanol production pathway (e.g., the canonical ethanol production pathway in yeast) to provide ATP surplus. In some embodiments, the coupled pathways disclosed herein provide anaerobic production of 2,4-FDCA, more efficiently and more cost-effectively than aerobic pathways for 2,4-FDCA production. Coupling 2,4-

FDCA and ethanol production further advantageously enables production of 2,4-FDCA with an economically valuable chemical.

In some embodiments, the electron consuming pathway is provided by the Calvin cycle enzymes phosphoribulokinase (PRK) and ribulose-1,5-bisphosphate carboxylase (RuBisCO). In some embodiments, the 2,4-FDCA pathway disclosed herein is coupled to Calvin cycle enzymes phosphoribulokinase (PRK) and ribulose-1,5-bisphosphate carboxylase (RuBisCO), and to an ethanol production pathway. In some embodiments, the present disclosure comprises recombinant microorganisms and related methods for converting one or more carbon sources to 2,4-furandicarboxylic acid (2,4-FDCA) and for converting ribulose-5-phosphate to glycerate-3-phosphate.

In some embodiments, the present disclosure provides microorganisms and related methods for coupling 2,4-FDCA production with ethanol production and carbon dioxide ($CO_2$) fixation and/or recycling. In some embodiments, coupling 2,4-FDCA production with ethanol production from glucose provides ATP, for example, according to equation 2:

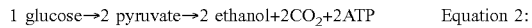

1 glucose→2 pyruvate→2 ethanol+2$CO_2$+2ATP     Equation 2:

In some embodiments, coupling 2,4-FDCA production with the enzymatic activity of PRK and RuBisCO provides redox balance by using of $CO_2$ as an electron acceptor for nicotinamide adenine dinucleotide (NADH) (or NADPH) oxidation to $NAD^+$ (or $NADP^+$).

In some embodiments, the recombinant microorganism of any one of the embodiments disclosed herein comprises: (1) at least one endogenous and/or exogenous nucleic acid molecule encoding one or more polypeptides capable of converting a carbon source to 2,4-FDCA via several enzymatically-catalyzed successive steps as described herein; (2) at least one endogenous and/or exogenous nucleic acid molecule encoding a polypeptide that catalyzes the production of ribulose-1,5-bisphosphate from ribulose-5-phosphate; and (3) at least one endogenous and/or exogenous nucleic acid molecule encoding a polypeptide that catalyzes the production of two molecules of glycerate-3-phosphate from the combination of $CO_2$ with ribulose-1,5-bisphosphate.

In some embodiments, the polypeptide that catalyzes the production of ribulose-1,5-bisphosphate from ribulose-5-phosphate is a phosphoribulokinase (PRK). In some embodiments, the phosphoribulokinase is classified as EC number 2.7.1.19. In some embodiments, the phosphoribulokinase (sPRK) is from *Spinacia oleracea*. In some embodiments, the phosphoribulokinase (PRK) is from *Synechococcus elongatus*. In some embodiments, the phosphoribulokinase (cfxPI) is from *Cupriavidus necator*. In some embodiments, the phosphoribulokinase (cbbP) is from *Nitrobacter vulgaris*.

In some embodiments, the polypeptide that catalyzes the production of glycerate-3-phosphate from the combination of $CO_2$ with ribulose-1,5-bisphosphate is a ribulose-1,5-bisphosphate carboxylase (RuBisCO). In some embodiments, the RuBisCO is classified as EC number 4.1.1.39. In some embodiments, the RuBisCO is selected from RuBisCO Form I, RuBisCO Form II, RuBisCO Form III, or a combination thereof. RuBisCO Form I is found in eukaryotes and bacteria, and consists of a hexadecamer composed of eight large subunits (RbcL) and eight small subunits (RbcS). The catalytic core is formed by eight L subunits, with eight S subunits on top and bottom of this core. RuBisCO Form II is comprised of dimers of L, ranging from L2-8 depending on the source. RuBisCO Form III is found only in some archaea, having dimers of L subunits. See Tabita et al., J Exp Bot, 59, 1515-24, 2008. In some embodiments, the RuBisCO Form I comprises large subunits (rbcL), small subunits (rbcS), or both, and is from *Synechococcus sp*. In some embodiments, the RuBisCO Form I (cbbL/cbbS) is from *Cupriavidus necator*. In some aspects, the RuBisCO Form I comprises large subunits (cbbL2), small subunits (cbbS2), or both, and is from *Cupriavidus necator*. In some embodiments, the RuBisCO Form II (cbbM) is from *Thiobacillus denitrificans*. In some embodiments, the RuBisCO Form II (cbbM) is from *Rhodospirillum rubrum*. In some embodiments, the RuBisCO Form II (cbbM) is from *Rhodoferax ferriducens*. In some embodiments, the RuBisCO Form II (cbbM) is from *Dechloromonas aromatica*. In some embodiments, the RuBisCO Form III (rbcL) is from *Thermococcus kodakarensis*. In some embodiments, the RuBisCO Form III (cbbL) is from *Haloferax sp*.

In some embodiments, the recombinant microorganism further comprises at least one endogenous and/or exogenous nucleic acid molecule encoding a protein-folding chaperone protein. In some embodiments, the chaperone protein promotes native folding and/or assembly of RuBisCO subunits. In some embodiments, RuBisCO is co-expressed in *S. cerevisiae* with chaperones from *E. coli* (GroES-GroEL), *Synechococcus elongatus* (RbcX), *S. cerevisiae* (HSP60-HSP10), or a combination thereof. In some embodiments, form II RuBisCO enzyme from *Thiobacillus denitrificans* is co-expressed in *S. cerevisiae* with chaperones GroES-GroEL and PRK from *Spinacia oleracea*. See Guadalupe-Medina et al. (Biotechnology for Biofuels, 6, 125, 2013) and Papapetridis et al. (Biotechnology for Biofuels, 11, 17, 2018). In some embodiments, form II RuBisCO from *Rhodospirillum rubrum* is co-expressed in a xylose-consuming *S. cerevisiae* strain with chaperones GroES-GroEL and PRK from *Spinacia oleracea*. See Xia et al. (ACS Synthetic Biology, 6, 2, 2017). In some embodiments, RuBisCO I and PRK, both from *Cupriavidus necator*, are co-expressed in a xylose-consuming *S. cerevisiae* strain with chaperones HSP6O-HSP10. See Li et al. (Scientific Reports, 6, 7, 2017). In some embodiments, the subunits of the form I RuBisCO enzyme from Synechococcus elongates is co-expressed in *S. cerevisiae* with the specific chaperone RbcX and GroES-GroEL. See U.S. Pat. No. 10,066,234. In some embodiments, a phosphoribulokinase from *Spinacia oleracea, Euglena gracilis* or Synechococcus elongates is expressed in *S. cerevisiae*.

Some embodiments of the present disclosure are shown in FIG. 1, which schematically depicts the biosynthetic conversion of a carbon feedstock (e.g., glucose) to 2,4-FDCA and ethanol, wherein the 2,4-FDCA pathway is coupled to the Calvin cycle enzymes phosphoribulokinase (PRK) and ribulose-1,5-bisphosphate carboxylase (RuBisCO), and to the canonical ethanol production pathway in yeast. In some embodiments, ribulose-5-phosphate is formed by the oxidative pentose pathway. In some embodiments, ribulose-5-phosphate is formed by the non-oxidative pentose pathway. In some embodiments, NADPH is not needed for biomass formation and ribulose-5-phosphate is primarily formed by the non-oxidative pentose pathway. In some embodiments, ribulose 1,5-bisphosphate is produced by phosphoribulokinases (PRK) from ATP and ribulose-5-phosphate. In some embodiments, RuBisCO catalyzes the combination of $CO_2$ with ribulose 1,5-bisphosphate, forming two molecules of glycerate-3-phosphate. In some embodiments, one molecule of glycerate-3-phosphate and one molecule of NADH are converted into one molecule of $CO_2$, one molecule of ethanol, and one molecule of ATP by yeast enzymes. In some aspects, the microorganism utilizes NADH and/or NADPH produced as a byproduct of 2,4-FDCA production to produce ethanol.

In some embodiments, ethanol produced from coupling the non-oxidative pentose pathway with RuBisCO allows $CO_2$ capture and an NADH negative ethanol-production pathway from glucose. In some embodiments, the recombinant microorganism comprises at least one genetic modification that leads to an up-regulation of an enzyme in a non-oxidative pentose pathway. In some embodiments, the genetic modification leads to an up-regulation of a gene selected from RPE1, TKL1, TAL1, NQM1, RKI1, or TKL2. In some embodiments, the recombinant microorganism comprises at least one genetic modification that leads to a down-regulation or deletion of an enzyme in a glycerol production pathway. In some embodiments, the recombinant microorganism comprises at least one genetic modification that leads to a down-regulation or deletion of glycerol-3-phosphate dehydrogenase (GPD2).

The present disclosure is also directed to methods of co-producing 2,4-FDCA and ethanol. In some embodiments, a method of co-producing 2,4-FDCA and ethanol comprises: contacting a recombinant microorganism as described herein with a fermentable carbon source under conditions sufficient to produce 2,4-FDCA and ethanol. In some embodiments, the carbon source comprises a hexose, a pentose, glycerol, and/or combinations thereof. In some embodiments, the conditions are anaerobic conditions. In some embodiments, the methods comprise cultivating the recombinant microorganism in a culture medium containing a feedstock providing a carbon source until 2,4-FDCA is produced in the absence of oxygen. In some embodiments, the methods produce a molar ratio of ethanol:2,4-FDCA of greater than 1:1, such as greater than 2:1, greater than 3:1, or greater than 4:1.

In some embodiments, the methods of co-producing 2,4-FDCA and ethanol in a recombinant microorganism comprise: (a) converting glyceraldehyde 3-phosphate (G3P) to 4-hydroxymethylfurfural phosphate; (b) converting 4-hydroxymethylfurfural phosphate to 4-hydroxymethylfurfural (4-HMF); (c) converting 4-HMF to 2,4-furandicarboxylic acid (2,4-FDCA), either directly or through production of one or more intermediates; (d) converting ribulose-5-phosphate to ribulose-1,5-bisphosphate; and (e) converting $CO_2$ and ribulose-1,5-bisphosphate to two molecules of glycerate-3-phosphate with a RiBisCO. In some embodiments, the methods comprise converting glyceraldehyde 3-phosphate (G3P) to 4-hydroxymethylfurfural phosphate with a methyl phosphate synthase. In some embodiments, the methods comprise converting 4-hydroxymethylfurfural phosphate to 4-hydroxymethylfurfural (4-HMF) with a phosphatase or a kinase. In some embodiments, the methods comprise converting 4-HMF to 2,4-furandicarboxylic acid (2,4-FDCA) directly. In some embodiments, the methods comprise converting 4-HMF to 2,4-furandicarboxylic acid (2,4-FDCA) through production of one or more intermediates. In some embodiments, the intermediates are furan-2,4-dicarbaldehyde, 4-(hydroxymethyl)furoic acid, 4-formylfuran-2-carboxylate, 4-formylfuran-2-carboxylate, and/or 2-formylfuran-4-carboxylate. In some embodiments, the methods comprise converting ribulose-5-phosphate to ribulose-1,5-bisphosphate with a phosphoribulokinase. In some embodiments, the methods comprise converting $CO_2$ and ribulose-1,5-bisphosphate to two molecules of glycerate-3-phosphate with a RiBisCO. In some embodiments, the RuBisCO is selected from Form I, Form II, Form III, or a combination thereof.

In some embodiments, the methods further comprise co-expressing a chaperone protein.

In some embodiments, the methods further comprise converting NADH and/or NADPH produced as a byproduct of 2,4-FDCA production and glycerate-3-phosphate to ethanol.

Coupling 2,4-FDCA Production with Phosphoketolase

In some embodiments, the present disclosure comprises recombinant microorganisms and related methods for anaerobically converting one or more carbon sources to 2,4-furandicarboxylic acid (2,4-FDCA) and ethanol. In some embodiments, the one or more carbon sources are selected from glycerol, a monosaccharide, or a combination thereof.

In some embodiments, the 2,4-FDCA pathway disclosed herein is coupled to electron consuming pathways to provide redox balance and with an ethanol production pathway (e.g., the canonical ethanol production pathway in yeast) to provide ATP surplus. In some embodiments, the coupled pathways disclosed herein provide anaerobic production of 2,4-FDCA, more efficiently and more cost-effectively than aerobic pathways for 2,4-FDCA production. Coupling 2,4-FDCA and ethanol production further advantageously enables production of 2,4-FDCA with an economically valuable chemical.

In some embodiments, the present disclosure provides microorganisms and related methods for coupling 2,4-FDCA production with ethanol production both from the redox-neutral canonical pathway and from an acetyl-CoA production pathway. Coupling the 2,4-FDCA pathway with ethanol production from glucose via the canonical pathway and with the acetyl-CoA production pathway advantageously provides a cofactor-balanced and ATP-positive 2,4-FDCA production process in the absence of oxygen.

In some embodiments, the electron consuming pathway is provided by the enzymes phosphoketolase (Pk) and phosphotransacetylase (PTA). In some embodiments, the 2,4-FDCA pathway disclosed herein is coupled to Pk and PTA, and to an ethanol production pathway. In some embodiments, the electron consuming pathway is provided by the enzymes phosphoketolase (Pk) and acetate kinase (Ack). In some embodiments, the 2,4-FDCA pathway disclosed herein is coupled to Pk and Ack, and to an ethanol production pathway.

In some embodiments, the present disclosure comprises recombinant microorganisms and related methods for converting one or more carbon sources to 2,4-furandicarboxylic acid (2,4-FDCA) and for converting xylulose-5-phosphate or fructose-6-phosphate to acetyl-CoA.

Figure 2:
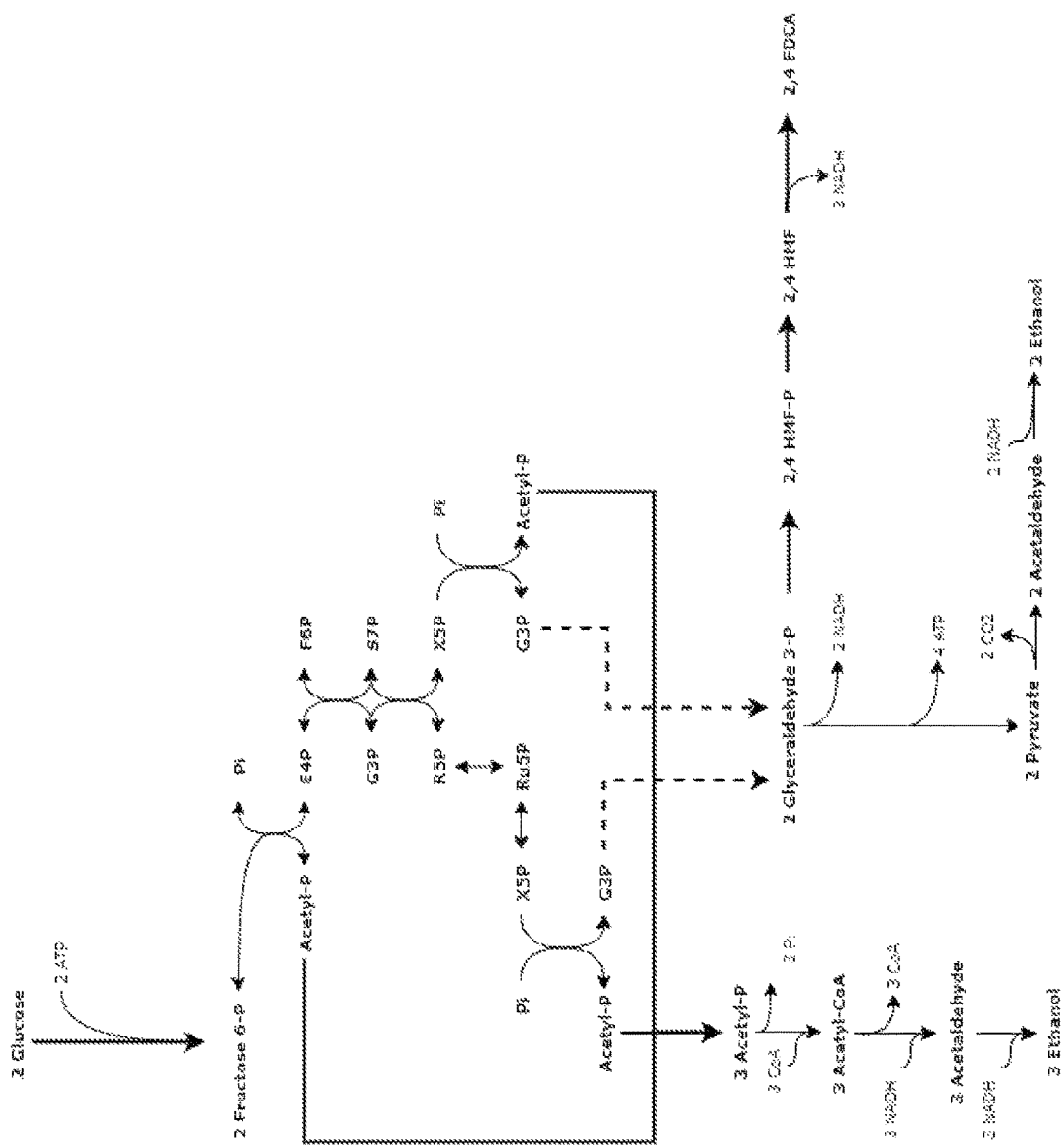
FIG. 2 is a schematic overview of a biosynthetic pathway utilized by recombinant microorganisms of the disclosure for 2,4-FDCA and ethanol production.

Some embodiments of the present disclosure are shown in FIG. 2, which schematically depicts the biosynthetic conversion of glucose to ethanol via the activities of Pk and PTA. In some embodiments, the Pk/PTA pathway consumes one molecule of NADH and produces 0.5 molecules of ATP per molecule of ethanol produced.

In some embodiments, the recombinant microorganism of any one of the embodiments disclosed herein comprises: (1) at least one endogenous and/or exogenous nucleic acid molecule encoding one or more polypeptides capable of converting a carbon source to 2,4-FDCA via several enzymatically-catalyzed successive steps as described herein; (2) at least one endogenous and/or exogenous nucleic acid molecule encoding a polypeptide that catalyzes the production of acetyl phosphate and D-glyceraldehyde-3-phosphate from D-xylulose-5-phosphate and phosphate, and/or at least one endogenous and/or exogenous nucleic acid molecule encoding a polypeptide that catalyzes the production of acetyl phosphate and erythrose-4-phosphate from fructose-6-phosphate and phosphate; (3) at least one endogenous and/or exogenous nucleic acid molecule encoding a polypeptide that catalyzes the production of acetyl-CoA from acetyl phosphate and free coenzyme A, and/or at least one endogenous and/or exogenous nucleic acid molecule encoding a polypeptide that catalyzes the production of acetate from acetyl phosphate and the production of acetyl-CoA from acetate; and (4) at least one nucleic acid molecule encoding one or more polypeptides that catalyze the production of acetaldehyde from acetyl-CoA, and/or at least one nucleic acid molecule encoding one or more polypeptides that catalyze the production of ethanol from acetyl-CoA.

In some embodiments, the intermediates for the production of 2,4-furandicarboxylic acid (2,4-FDCA) from 4-HMF are furan-2,4-dicarbaldehyde, 4-(hydroxymethyl)furoic acid, 4-formylfuran-2-carboxylate, 4-formylfuran-2-carboxylate, and/or 2-formylfuran-4-carboxylate.

In some embodiments, the polypeptide that catalyzes the production of acetyl phosphate and D-glyceraldehyde-3-phosphate from D-xylulose-5-phosphate and phosphate is a phosphoketolase. In some embodiments, the phosphoketolase utilizes xylulose-5-phosphate as a substrate and is classified as EC number 4.1.2.9. In some embodiments, the phosphoketolase is a single-specificity phosphoketolase with specificity for xylulose-5-phosphate.

In some embodiments, the polypeptide that catalyzes the production of acetyl phosphate and erythrose-4-phosphate from fructose-6-phosphate and phosphate is a phosphoketolase. In some embodiments, the phosphoketolase utilizes fructose-6-phosphate as a substrate and is classified as EC number 4.1.2.22. In some embodiments, the phosphoketolase is a single-specificity phosphoketolase with specificity for fructose-6-phosphate.

In some embodiments, the phosphoketolase is a dual-specificity phosphoketolase with specificity for both fructose-6-phosphate and xylulose-5-phosphate. In some embodiments, the phosphoketolase is a dual-specificity phosphoketolase with specificity for both fructose-6-phosphate and xylulose-5-phosphate, but with higher activity toward xylulose-5-phosphate.

In some embodiments, the phosphoketolase is from *Bifidobacterium breve*. In some embodiments, the phosphoketolase is from *Clostridium acetobutylicum*. In some embodiments, the phosphoketolase is from *Leuconostoc mesenteroides*. In some embodiments, the phosphoketolase is from *B. lactis*. In some embodiments, the phosphoketolase is from *B. adolescentis*. In some embodiments, the phosphoketolase is from *L. plantarum*. In some embodiments, the phosphoketolase is from *A. niger*. In some embodiments, the phosphoketolase is from *B. animalis*.

In some embodiments, the polypeptide that catalyzes the production of acetyl-CoA from acetyl phosphate and free coenzyme A is a phosphotransacetylase. In some embodiments, the phosphotransacetylase is classified as EC number 2.3.1.8. In some embodiments, the phosphotransacetylase is from *B. subtilis*. In some embodiments, the phosphotransacetylase is from *B. adolescentis*. In some embodiments, the phosphotransacetylase is from *L. plantarum*.

In some embodiments, the polypeptide that catalyzes the production of acetate from acetyl phosphate is an acetate kinase. In some embodiments, the acetate kinase is classified as EC number 2.7.2.12. In some embodiments, the polypeptide that catalyzes the production of acetyl-CoA from acetate is an acetyl-CoA synthetase or an acetate-CoA ligase. In some embodiments, the acetyl-CoA synthetase or an acetate-CoA ligase is classified as EC number 6.2.1.1.

In some embodiments, the polypeptide that catalyzes the production of acetaldehyde from acetyl-CoA is an acetaldehyde dehydrogenase. In some embodiments, the polypeptide that catalyzes the production of ethanol from acetaldehyde is an alcohol dehydrogenase.

In some embodiments, the polypeptide that catalyzes the production of ethanol from acetyl-CoA is a bifunctional acetaldehyde-alcohol dehydrogenase. In some embodiments, the bifunctional acetaldehyde-alcohol dehydrogenase is selected from enzymes classified as both EC number 1.2.1.10 and EC number 1.1.1.1. In some embodiments, the bifunctional acetaldehyde-alcohol dehydrogenase is an NADH- and/or NADPH-dependent bifunctional acetaldehyde-alcohol dehydrogenase. In some embodiments, the NADH- and/or NADPH-dependent bifunctional acetaldehyde-alcohol dehydrogenase is selected from enzymes classified as EC number 1.2.1.10 or EC number 1.1.1.2. In some embodiments, the acetaldehyde-alcohol dehydrogenase (adhE) is from *B. adolescentis*. In some embodiments, the acetaldehyde-alcohol dehydrogenase (EhADH2) is from *E. histolytica*.

In some embodiments, the recombinant microorganism further comprises at least one genetic modification that leads to a down-regulation or a deletion of an enzyme in a glycerol-production pathway. In some embodiments, the enzyme in the glycerol-production pathway is a glycerol-3-phosphate dehydrogenase. In some embodiments, the glycerol-3-phosphate dehydrogenase is classified as EC number 1.1.1.8. In some embodiments, the enzyme in the glycerol-production pathway is a glycerol-3-phosphate phosphatase. In some embodiments, the glycerol-3-phosphate phosphatase is classified as EC number 3.1.3.21. In some embodiments, the enzyme in the glycerol-production pathway is a glycerol-1-phosphate phosphohydrolase. In some embodiments, the enzyme in the glycerol-production pathway is a formate dehydrogenase.

In some embodiments, the recombinant microorganism comprises at least one genetic modification that leads to an up-regulation of an enzyme in a non-oxidative pentose phosphate pathway. In some embodiments, the enzyme in the non-oxidative pentose phosphate pathway is a transaldolase. In some embodiments, the transaldolase is classified as EC number 2.2.1.2. In some embodiments, the enzyme in the non-oxidative pentose phosphate pathway is a transketolase. In some embodiments, the transketolase is classified as EC number 2.2.1.1. In some embodiments, the enzyme in the non-oxidative pentose phosphate pathway is a ribose-5-phosphate isomerase. In some embodiments, the ribose-5-phosphate isomerase is classified as EC number 5.3.1.6. In some embodiments, the enzyme in the non-oxidative pentose phosphate pathway is a ribulose-5-phosphate 3-epimerase. In some embodiments, the ribulose-5-phosphate 3-epimerase is classified as EC number 5.1.3.1.

In some embodiments, the microorganism utilizes NADH and/or NADPH produced as a byproduct of 2,4-FDCA production to produce ethanol.

The present disclosure is also directed to methods of co-producing 2,4-FDCA and ethanol. In some embodiments, a method of co-producing 2,4-FDCA and ethanol comprises: contacting a recombinant microorganism as described herein with a fermentable carbon source under conditions sufficient to produce 2,4-FDCA and ethanol. In some embodiments, the carbon source comprises a hexose, a pentose, glycerol, and/or combinations thereof. In some embodiments, the conditions are anaerobic conditions. In some embodiments, the methods comprise cultivating the recombinant microorganism in a culture medium containing a feedstock providing a carbon source until 2,4-FDCA is produced in the absence of oxygen. In some embodiments, the methods produce a molar ratio of ethanol:2,4-FDCA of greater than 1:1, such as greater than 2:1, greater than 3:1, or greater than 4:1.

In some embodiments, the methods of co-producing 2,4-FDCA and ethanol in a recombinant microorganism comprise: (a) converting glyceraldehyde 3-phosphate (G3P) to 4-hydroxymethylfurfural phosphate; (b) converting 4-hydroxymethylfurfural phosphate to 4-hydroxymethylfurfural (4-HMF); (c) converting 4-HMF to 2,4-furandicarboxylic acid (2,4-FDCA), either directly or through production of one or more intermediates; (d) converting D-xylulose-5-phosphate and phosphate to acetyl phosphate and D-glyceraldehyde-3-phosphate, and/or converting fructose-6-phosphate and phosphate to acetyl phosphate and erythrose-4-phosphate; (e) converting: (1) acetyl phosphate and free coenzyme A to acetyl-CoA; and/or (2) acetyl phosphate to acetate and the acetate to acetyl-CoA; and (f) converting: (1) acetyl-CoA to acetaldehyde; and/or (2) acetyl-CoA to ethanol. In some embodiments, the methods comprise converting glyceraldehyde 3-phosphate (G3P) to 4-hydroxymethylfurfural phosphate with a methyl phosphate synthase. In some embodiments, the methods comprise converting 4-hydroxymethylfurfural phosphate to 4-hydroxymethylfurfural (4-HMF) with a phosphatase or a kinase. In some embodiments, the methods comprise converting 4-HMF to 2,4-furandicarboxylic acid (2,4-FDCA) directly. In some embodiments, the methods comprise converting 4-HMF to 2,4-furandicarboxylic acid (2,4-FDCA) through production of one or more intermediates. In some embodiments, the intermediates are furan-2,4-dicarbaldehyde, 4-(hydroxymethyl)furoic acid, 4-formylfuran-2-carboxylate, 4-formylfuran-2-carboxylate, and/or 2-formylfuran-4-carboxylate. In some embodiments, the methods comprise converting D-xylulose-5-phosphate and phosphate to acetyl phosphate and D-glyceraldehyde-3-phosphate, and/or converting fructose-6-phosphate and phosphate to acetyl phosphate and erythrose-4-phosphate with a phosphoketolase. In some embodiments, the methods comprise converting acetyl phosphate and free coenzyme A to acetyl-CoA with a phosphotransacetylase. In some embodiments, the methods comprise converting acetyl phosphate to acetate with an acetate kinase. In some embodiments, the methods comprise converting acetate to acetyl-CoA with an acetyl-CoA synthetase or an acetate-CoA ligase. In some embodiments, the methods comprise converting acetyl-CoA to acetaldehyde with an acetaldehyde dehydrogenase. In some embodiments, the methods comprise converting acetaldehyde to ethanol with an alcohol dehydrogenase. In some embodiments, the methods comprise converting acetyl-CoA to ethanol with a bifunctional acetaldehyde-alcohol dehydrogenase.

In some embodiments, the methods further comprise converting NADH and/or NADPH produced as a byproduct of 2,4-FDCA production and glycerate-3-phosphate to ethanol.

Coupling 2,4-FDCA Production with MSA-Based 1-Propanol Pathway

In some embodiments, the present disclosure comprises recombinant microorganisms and related methods for anaerobically converting one or more carbon sources to 2,4-furandicarboxylic acid (2,4-FDCA), 1-propanol, and ethanol. In some embodiments, the one or more carbon sources are selected from glycerol, a monosaccharide, or a combination thereof.

In some embodiments, the 2,4-FDCA pathway disclosed herein is coupled to electron consuming pathways to provide redox balance and with an ethanol production pathway (e.g., the canonical ethanol production pathway in yeast) to provide ATP surplus. In some embodiments, the coupled pathways disclosed herein provide anaerobic production of 2,4-FDCA, more efficiently and more cost-effectively than aerobic pathways for 2,4-FDCA production. Coupling 2,4-FDCA, 1-propaol, and ethanol production further advantageously enables production of 2,4-FDCA with economically valuable chemicals.

In some embodiments, the present disclosure provides microorganisms and related methods for coupling 2,4-FDCA production with 1-propanol product and ethanol production from the redox-neutral canonical pathway. Coupling the 2,4-FDCA pathway with 1-propanol production and ethanol production from glucose via the canonical advantageously provides a cofactor-balanced and ATP-positive 2,4-FDCA production process in the absence of oxygen.

In some embodiments, the present disclosure comprises recombinant microorganisms and related methods for converting one or more carbon sources to 2,4-furandicarboxylic acid (2,4-FDCA) and for converting phosphoenol pyruvate to 1-propanol via malonate semialdehyde.

Figure 3:
FIG. 3 is a schematic overview of a biosynthetic pathway utilized by recombinant microorganisms of the disclosure for 2,4-FDCA, ethanol, and 1-propanol production.

Some embodiments of the present disclosure are shown in FIG. 3, which schematically depicts the biosynthetic conversion of a carbon feedstock (e.g., glucose) to 2,4-FDCA and 1-propanol, wherein the 2,4-FDCA pathway is coupled to the MSA-based pathway to 1-propanol, and to the canonical ethanol production pathway in yeast.

In some embodiments, the recombinant microorganism of any one of the embodiments disclosed herein comprises: (1) at least one endogenous and/or exogenous nucleic acid molecule encoding one or more polypeptides capable of converting a carbon source to 2,4-FDCA via several enzymatically-catalyzed successive steps as described herein; (2) at least one endogenous and/or exogenous nucleic acid molecule encoding a polypeptide that catalyzes the production of oxaloacetate from phosphoenol pyruvate (PEP); (3) at least one endogenous and/or exogenous nucleic acid molecule encoding a polypeptide that catalyzes the production of malonate semialdehyde from oxaloacetate and/or the production of aspartate from oxaloacetate, the production of β-alanine from aspartate, and the production of malonate semialdehyde from β-alanine; (4) at least one nucleic acid molecule encoding one or more polypeptides that catalyze the production of 3-hydroxypropionic acid (3-HP) from malonate semialdehyde; (5) at least one nucleic acid molecule encoding one or more polypeptides that catalyze the production of propionyl-CoA from 3-HP; and (6) at least one nucleic acid molecule encoding one or more polypeptides that catalyze the production of 1-propanol from propionyl-CoA, and/or at least one nucleic acid molecule encoding one or more polypeptides that catalyze the production of propionaldehyde from propionyl-CoA and the production of 1-propanol from propionaldehyde.

In some embodiments, the intermediates are furan-2,4-dicarbaldehyde, 4-(hydroxymethyl)furoic acid, 4-formylfuran-2-carboxylate, 4-formylfuran-2-carboxylate, and/or 2-formylfuran-4-carboxylate.

In some embodiments, the polypeptide that catalyzes the production of oxaloacetate from phosphoenol pyruvate (PEP) is a phosphoenol pyruvate carboxylase (ppc) and/or a phosphoenol pyruvate carboxykinase (pepck). In some aspects, the phosphoenol pyruvate carboxylase and/or phosphoenol pyruvate carboxykinase are selected from a fungi, yeast, bacterium, insect, animal, plant, or flagellate. In some aspects, the phosphoenol pyruvate carboxylase and/or phosphoenol pyruvate carboxykinase are from *E. coli*.

In some embodiments, the polypeptide that catalyzes the production of malonate semialdehyde from oxaloacetate comprise an oxaloacetate decarboxylase that catalyzes the direct decarboxylation of oxaloacetate. In some embodiments, the recombinant microorganism comprises one or more oxaloacetate decarboxylases including, but not limited to, enzymes with EC number 4.1.1.72, EC number 4.1.1.7, or EC number 4.1.1.71. In some embodiments, the oxaloacetate decarboxylase is selected from an α-ketoisovalerate decarboxylase, a benzoylformate decarboxylase, or a 2-oxoglutarate decarboxylase. In some embodiments, the alpha-ketoisovalerate decarboxylase (kdca) is from *Lactococcus lactis*. In some embodiments, the benzoylformate decarboxylase (Mdlc) is from *Pseudomonas putida*. In some embodiments, the 2-oxoglutarate decarboxylase (Oxdc) is from *Oenococcus oeni*. In some embodiments, the 2-oxoglutarate decarboxylase (oxdc) is from *Euglena gracilis*. In some aspects, the oxaloacetate decarboxylase is a genetically modified variant of the foregoing enzymes. Examples of genetically modified enzyme variants that are suitable for catalyzing the direct conversion of oxaloacetate to malonate semialdehyde are described, for example, in U.S. Patent Application Publication No. 2010/0021978, U.S. Pat. No. 8,809,027, International Application Publication No. WO 2018/213349, and U.S. patent application Ser. No. 16/719,833, which are hereby incorporated by reference.

In some embodiments, the polypeptide that catalyzes the production of aspartate from oxaloacetate is an aspartate amino transferase (aat2). In some embodiments, the aspartate amino transferase is from *S. cerevisiae*.

In some embodiments, the polypeptide that catalyzes the production of β-alanine from aspartate is an aspartate decarboxylase (pand). In some embodiments, the aspartate decarboxylase is from *Tribolium castaneum*. In some embodiments, the aspartate decarboxylase is from *Corynebacterium glutamicum*.

In some embodiments, the polypeptide that catalyzes the production of malonate semialdehyde from β-alanine is a β-alanine pyruvate amino transferase (baat) and/or a β-alanine transaminase (pyd4). In some embodiments, the β-alanine pyruvate amino transferase is from *Bacillus cereus*. In some embodiments, the β-alanine transaminase is from *Lachancea kluyveri*.

In some embodiments, the aspartate amino transferase, aspartate decarboxylase, β-alanine pyruvate amino transferase, and/or β-alanine transaminase are selected from a fungi, yeast, bacterium, insect, animal, plant, or flagellate.

In some embodiments, the polypeptide that catalyzes the production of 3-HP from malonate semialdehyde is a 3-hydroxypropionic acid dehydrogenase. In some embodiments, the 3-hydroxypropionic acid dehydrogenase is classified as EC number 1.1.1.381 and/or EC number 1.1.1.298. In some embodiments, the 3-hydroxypropionic acid dehydrogenase is from a fungi, yeast, bacterium, insect, animal, plant, or flagellate. In some embodiments, the 3-hydroxypropionic acid dehydrogenase (mcr-1) is from *Chloroflexus aurantiacus*. In some embodiments, the 3-hydroxypropionic acid dehydrogenase (adh) is from *Arthrobacter enclensis*. In some embodiments, the 3-hydroxypropionic acid dehydrogenase (mmsb) is from *Bacillus cereus*. In some embodiments, the 3-hydroxypropionic acid dehydrogenase (ydfg-0) is from *E. coli*. In some embodiments, the 3-hydroxypropionic acid dehydrogenase (YDF1) is from *Saccharomyces cerevisiae*. In some embodiments, the 3-hydroxypropionic acid dehydrogenase (HPD1) is from *Candida albicans*.

In some embodiments, the polypeptide that catalyzes the production of propionyl-CoA from 3-HP is a propionyl-CoA synthase. In some embodiments, the propionyl-CoA synthase is from *Chloroflexus aggregans*. In some embodiments, the propionyl-CoA synthase is from *Roseiflexus castenholzii*. In some embodiments, the propionyl-CoA synthase is from *Chloroflexus aurantiacus*. In some embodiments, the propionyl-CoA synthase is classified as EC number 6.2.1.17 and/or EC number 6.2.1.36.

In some embodiments, the polypeptides that catalyze the production of propionyl-CoA from 3-HP are a 3-hydroxypropionyl-CoA synthetase/transferase, a 3-hydroxypropionyl-CoA dehydratase, and an acrylyl-CoA reductase. In some embodiments, the 3-hydroxypropionyl-CoA synthetase/transferase is classified as EC number 2.8.3.1, EC number 6.2.1.17, and/or EC number 6.2.1.36. In some embodiments, the 3-hydroxypropionyl-CoA dehydratase is classified as EC number 4.2.1.116, EC number 4.2.1.55, EC number 4.2.1.150, and/or EC number 4.2.1.17). In some embodiments, the acrylyl-CoA reductase is classified as EC number 1.3.1.84 and/or EC number 1.3.1.95.

In some embodiments, the polypeptide that catalyzes the production of 1-propanol from propionyl-CoA is a bifunctional alcohol/aldehyde dehydrogenase. In some embodiments, the bifunctional alcohol/aldehyde dehydrogenase is classified as EC number 1.1.1.1, EC number 1.2.1.4 and/or EC number 1.2.1.5.

In some embodiments, the polypeptide that catalyzes the production of propionaldehyde from propionyl-CoA is an aldehyde dehydrogenase (acetylating). In some embodiments, the aldehyde dehydrogenase (acetylating) is classified as EC number 1.2.1.10. In some embodiments, the polypeptide that catalyzes the production of 1-propanol from propionaldehyde is an alcohol dehydrogenase. In some embodiments, the alcohol dehydrogenase is classified as EC number 1.1.1.1. In some embodiments, the alcohol dehydrogenase is alcohol dehydrogenase E (ADHE) from *Clostridium beijerinckii*. In some embodiments, the alcohol dehydrogenase is alcohol dehydrogenase E (ADHE) from *Clostridium arbusti*.

In some embodiments, the microorganism utilizes NADH and/or NADPH produced as a byproduct of 2,4-FDCA production to produce ethanol.

The present disclosure is also directed to methods of co-producing 2,4-FDCA, 1-propanol, and ethanol. In some embodiments, a method of co-producing 2,4-FDCA, 1-propanol, and ethanol comprises: contacting a recombinant microorganism as described herein with a fermentable carbon source under conditions sufficient to produce 2,4-FDCA, 1-propanol, and ethanol. In some embodiments, the carbon source comprises a hexose, a pentose, glycerol, and/or combinations thereof. In some embodiments, the conditions are anaerobic conditions. In some embodiments, the methods comprise cultivating the recombinant microorganism in a culture medium containing a feedstock providing a carbon source until 2,4-FDCA is produced in the absence of oxygen. In some embodiments, the methods produce a molar ratio of ethanol:2,4-FDCA of greater than 1:1, such as greater than 2:1, greater than 3:1, or greater than 4:1.

In some embodiments, the methods of co-producing 2,4-FDCA, 1-propanol, and ethanol in a recombinant microorganism comprise: (a) converting glyceraldehyde 3-phosphate (G3P) to 4-hydroxymethylfurfural phosphate; (b)

converting 4-hydroxymethylfurfural phosphate to 4-hydroxymethylfurfural (4-HMF); (c) converting 4-HMF to 2,4-furandicarboxylic acid (2,4-FDCA), either directly or through production of one or more intermediates; (d) converting phosphoenol pyruvate (PEP) to oxaloacetate; (e) converting oxaloacetate to malonate semialdehyde, and/or converting oxaloacetate to aspartate, aspartate to β-alanine, and β-alanine to malonate semialdehyde; (f) converting malonate semialdehyde to 3-hydroxypropionic acid (3-HP); (g) converting 3-HP to propionyl-CoA; and (g) propionyl-CoA to 1-propanol, and/or propionyl-CoA to propionaldehyde and propionaldehyde to 1-propanol.

In some embodiments, the methods comprise converting glyceraldehyde 3-phosphate (G3P) to 4-hydroxymethylfurfural phosphate with a methyl phosphate synthase. In some embodiments, the methods comprise converting 4-hydroxymethylfurfural phosphate to 4-hydroxymethylfurfural (4-HMF) with a phosphatase or a kinase. In some embodiments, the methods comprise converting 4-HMF to 2,4-furandicarboxylic acid (2,4-FDCA) directly. In some embodiments, the methods comprise converting 4-HMF to 2,4-furandicarboxylic acid (2,4-FDCA) through production of one or more intermediates. In some embodiments, the intermediates are furan-2,4-dicarbaldehyde, 4-(hydroxymethyl)furoic acid, 4-formylfuran-2-carboxylate, 4-formylfuran-2-carboxylate, and/or 2-formylfuran-4-carboxylate.

In some embodiments, the methods comprise converting phosphoenol pyruvate (PEP) to oxaloacetate with a phosphoenol pyruvate carboxylase and/or phosphoenol pyruvate carboxykinase. In some embodiments, the methods comprise converting oxaloacetate to malonate semialdehyde with an oxaloacetate decarboxylase. In some embodiments, the methods comprise converting oxaloacetate to aspartate with aspartate amino transferase. In some embodiments, the methods comprise converting aspartate to β-alanine with aspartate decarboxylas. In some embodiments, the methods comprise converting β-alanine to malonate semialdehyde with β-alanine pyruvate amino transferase. In some embodiments, the methods comprise converting malonate semialdehyde to 3-hydroxypropionic acid (3-HP) with 3-hydroxypropionic acid dehydrogenase. In some embodiments, the methods comprise converting 3-HP to propionyl-CoA with propionyl-CoA synthase. In some embodiments, the methods comprise converting propionyl-CoA to 1-propanol with a bifunctional alcohol/aldehyde dehydrogenase. In some embodiments, the methods comprise converting propionyl-CoA to propionaldehyde with aldehyde dehydrogenase (acetylating). In some embodiments, the methods comprise converting propionaldehyde to 1-propanol with an alcohol dehydrogenase.

In some embodiments, the methods further comprise converting NADH and/or NADPH produced as a byproduct of 2,4-FDCA production to ethanol.

Coupling 2,4-FDCA Production with Glycerol and Ethanol Production

In some embodiments, the present disclosure comprises recombinant microorganisms and related methods for anaerobically converting one or more carbon sources to 2,4-furandicarboxylic acid (2,4-FDCA), ethanol and glycerol.

In some embodiments, the 2,4-FDCA pathway disclosed herein is coupled to electron consuming pathways to provide redox balance and with an ethanol production pathway (e.g., the canonical ethanol production pathway in yeast) to provide ATP surplus. In some embodiments, the coupled pathways disclosed herein provide anaerobic production of 2,4-FDCA, more efficiently and more cost-effectively than aerobic pathways for 2,4-FDCA production. Coupling 2,4-FDCA and ethanol production further advantageously enables production of 2,4-FDCA with an economically valuable chemical.

In some embodiments, the electron consuming pathway is provided by the yeast glycerol-production pathway. In some embodiments, the 2,4-FDCA pathway disclosed herein is coupled to a glycerol-production pathway, and to an ethanol production pathway. In some embodiments, the present disclosure comprises recombinant microorganisms and related methods for converting one or more carbon sources to 2,4-furandicarboxylic acid (2,4-FDCA) and for converting dihydroxyacetone phosphate (DHAP) into glycerol.

In some embodiments, the present disclosure provides microorganisms and related methods for coupling 2,4-FDCA production with ethanol and glycerol production. In some embodiments, coupling 2,4-FDCA production with ethanol production from glucose provides ATP, for example, according to equation 2:

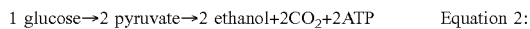

1 glucose→2 pyruvate→2 ethanol+2CO$_2$+2ATP    Equation 2:

In some embodiments, the excess of NADH, generated from FDCA production and from biosynthetic reactions, is reoxidized by reducing part of the sugar substrate to glycerol, according to equations 3 and 4:

1 glucose→2DHAP    Equation 3:

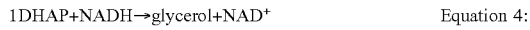

1DHAP+NADH→glycerol+NAD$^+$    Equation 4:

In some embodiments, coupling 2,4-FDCA production with the yeast glycerol-production pathway provides redox balance by using glycerol as an electron acceptor for nicotinamide adenine dinucleotide (NADH) (or NADPH) oxidation to NAD$^+$ (or NADP$^+$).

In some embodiments, the recombinant microorganism of any one of the embodiments disclosed herein comprises: (1) at least one endogenous and/or exogenous nucleic acid molecule encoding one or more polypeptides capable of converting a carbon source to 2,4-FDCA via several enzymatically-catalyzed successive steps as described herein; (2) at least one endogenous and/or exogenous nucleic acid molecule encoding a polypeptide that catalyzes the production of glycerol from DHAP.

In some embodiments, the reduction of dihydroxyacetone phosphate (DHAP) to glycerol-3-phosphate (G3P) is catalyzed by a glycerol-3-phosphate dehydrogenase. In some embodiments, G3P is subsequently dephosphorylated by a glycerol-3-phosphatase.

In some embodiments, the endogenous and/or exogenous nucleic acid molecule encoding a polypeptide that catalyzes the production of glycerol-3-phosphate (G3P) from DHAP, is a glycerol-3-phosphate dehydrogenase. In some embodiments, the glycerol-3-phosphate dehydrogenase is classified as EC number 1.1.1.8 or EC number 1.1.5.3. In some embodiments, the glycerol-3-phosphate dehydrogenase is encoded by the GPD1 gene. In some embodiments, the glycerol-3-phosphate dehydrogenase is encoded by the GPD2. In some embodiments, the glycerol-3-phosphate dehydrogenase polypeptides are encoded by both GPD1 and GPD2 genes. In some embodiments, a GPD1 gene, a GPD2 gene, or both are up-regulated in the microorganism. In some embodiments, extras copies of the GPD1 gene, GPD2 gene, or both are integrated into the microorganism.

In some embodiments, the endogenous and/or exogenous nucleic acid molecule encoding a polypeptide that catalyzes the production of glycerol from glycerol-3-phosphate (G3P) is a glycerol-3-phosphatase. In some embodiments, the glycerol-3-phosphatase is classified as EC number 3.1.3.21. In some embodiments, the glycerol-3-phosphatase is encoded by the RHR2 gene. In some embodiments, the glycerol-3-phosphatase is encoded by the HOR2 gene. In some embodiments, glycerol-3-phosphatase polypeptides are encoded by both RHR2 and HOR2 genes. In some embodiments, a RHR2 gene, a HOR2 gene, or both are up-regulated in the microorganism. In some embodiments, extras copies of the RHR2 gene, HOR2 gene, or both are integrated into the microorganism.

Figure 4:
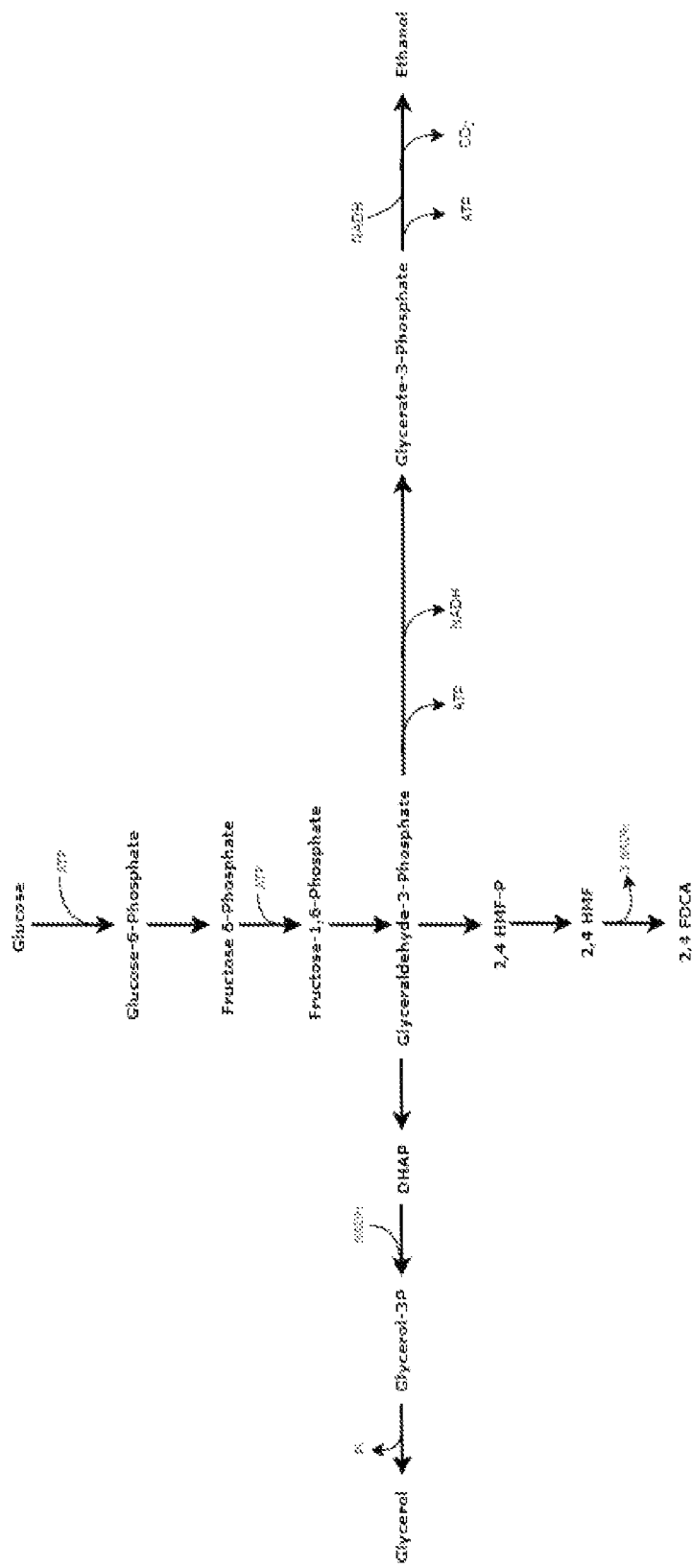
FIG. 4 is a schematic overview of a biosynthetic pathway utilized by recombinant microorganisms of the disclosure for 2,4-FDCA, ethanol, and glycerol production.

Some embodiments of the present disclosure are shown in FIG. 4, which schematically depicts the biosynthetic conversion of a carbon feedstock (e.g., glucose) to 2,4-FDCA, ethanol and glycerol, wherein the 2,4-FDCA pathway is coupled to yeast glycerol-producing pathway and to the canonical ethanol production pathway in yeast.

Culturing and Feedstock

Culturing of the microorganisms used in the methods of the disclosure may be conducted using any number of processes known in the art for culturing and fermenting substrates using the microorganisms of the present disclosure.

The fermentation may be carried out in any suitable bioreactor, such as Continuous Stirred Tank Bioreactor, Bubble Column Bioreactor, Airlift Bioreactor, Fluidized Bed Bioreactor, Packed Bed Bioreactor, Photo-Bioreactor, Immobilized Cell Reactor, Trickle Bed Reactor, Moving Bed Biofilm Reactor, Bubble Column, Gas Lift Fermenter, Membrane Reactors such as Hollow Fiber Membrane Bioreactor. In some aspects, the bioreactor comprises a first, growth reactor in which the microorganisms are cultured, and a second, fermentation reactor, to which fermentation broth from the growth reactor is fed and in which most of the fermentation product is produced. In some aspects, the bioreactor simultaneously accomplishes the culturing of microorganism and the producing the fermentation product from carbon sources such substrates and/or feedstocks provided.

During fermentation, anaerobic conditions can be maintained by, for example, sparging nitrogen through the culture medium. A suitable temperature for fermentation (e.g., about 30° C.) can be maintained using any method known in the art. A near physiological pH (e.g., about 6.5) can be maintained by, for example, automatic addition of sodium hydroxide. The bioreactor can be agitated at, for example, about 50 rpm until fermentation has run to completion.

In some embodiments, the methods of the present disclosure further comprise recovering, collecting, and/or isolating a 2,4-FDCA monomer or polymer. The recovery/collection/isolation can be by methods known in the art, such as distillation, solid-liquid separation, crystallization, precipitation, membrane-based separation gas stripping, solvent extraction, and expanded bed adsorption.

In some embodiments, the feedstock comprises a carbon source. In some embodiments, the carbon source may be selected from sugars, glycerol, alcohols, organic acids, alkanes, fatty acids, lignocellulose, proteins, carbon dioxide, and carbon monoxide. In some embodiments, the carbon source is a sugar. In some embodiments, the sugar is a monosaccharide. In some embodiments, the sugar is a polysaccharide. In some embodiments, the sugar is glucose or oligomers of glucose thereof. In some embodiments, the oligomers of glucose are selected from fructose, sucrose, starch, cellobiose, maltose, lactose and cellulose. In some embodiments, the sugar is a five carbon sugar. In some embodiments, the sugar is a six carbon sugar. In some embodiments, the feedstock comprises one or more five carbon sugars and/or one or more six carbon sugars. In some embodiments, the feedstock comprises one or more of xylose, glucose, arabinose, galactose, maltose, fructose, mannose, sucrose, and/or combinations thereof. In some embodiments, the feedstock comprises one or more of xylose and/or glucose. In some embodiments, the feedstock comprises one or more of arabinose, galactose, maltose, fructose, mannose, sucrose, and/or combinations thereof.

In some embodiments, the microbes utilize one or more five carbon sugars (pentoses) and/or one or more six carbon sugars (hexoses). In some embodiments, the microbes utilize one or more of xylose and/or glucose. In some embodiments, the microbes utilize one or more of arabinose, galactose, maltose, fructose, mannose, sucrose, and/or combinations thereof. In some embodiments, the microbes utilize one or more of xylose, glucose, arabinose, galactose, maltose, fructose, mannose, sucrose, and/or combinations thereof.

In some embodiments, hexoses may be selected from D-allose, D-altrose, D-glucose, D-mannose, D-gulose, D-idose, D-galactose, D-talose, D-tagtose, D-sorbose, D-fructose, D-psicose, and other hexoses known in the art. In some embodiments, pentoses may be selected from D-xylose, D-ribose, D-arabinose, D-lyxose, D-xylulose, D-ribulose, and other pentoses known in the art. In some embodiments, the hexoses and pentoses may be selected from the levorotary or dextrorotary enantiomer of any of the hexoses and pentoses disclosed herein.

TABLE 1

Candidate Phosphoribulokinases

| Name | Organism | ID | SEQ ID NO: |
|---|---|---|---|
| sPRK | Spinacia oleracea | P09559.1 | 1 |
| PRK | Synechococcus | BAD78757.1 | 2 |
| cfxP1 | Cupriavidus necator | P19923.3 | 3 |
| cbbP | Nitrobacter vulgaris | P37100.1 | 4 |

TABLE 2

Candidates for Form I RuBisCO

| Name | Organism | ID | SEQ ID NO: |
|---|---|---|---|
| rbcL | Synechococcus sp | P00880 | 5 |
| rbeS | Synechococcus sp | P04716 | 6 |
| cbbL/cbbS | Cupriavidus necator | AAA83745.1 | 7 |
| cbbL2 | Cupriavidus necator | CAJ96184.1 | 8 |
| cbbS2 | Cupriavidus necator | P09658.2 | 9 |

TABLE 3

Candidates for Form II RuBisCO

| Name | Organism | ID | SEQ ID NO: |
|---|---|---|---|
| cbbM | Thiobacillus denitrificans | Q60028 | 10 |
| cbbM | Rhodospirillum rubrum | P04718 | 11 |
| cbbM | Rhodoferax ferriducens | Q21YM9.1 | 12 |
| cbbM | Dechloromonas aromatica | Q479W5.1 | 13 |

TABLE 4

Candidates for Form III RuBisCO

| Name | Organism | ID | SEQ ID NO: |
|---|---|---|---|
| rbcL | Thermococcus kodakarensis | O93627.5 | 14 |
| cbbL | Haloferax sp. | CQR50548.1 | 15 |

TABLE 5

Candidate Phosphoketolases

| Organism | ID | SEQ ID NO: |
|---|---|---|
| KND53308.1 | Bifidobacterium breve | 16 |
| KHD36088.1 | Clostridium acetobutylicum | 17 |
| AAV66077.1 | Leuconostoc mesenteroides | 18 |

TABLE 6

Candidate Phosphotransacetylases

| Organism | SEQ ID NO: |
|---|---|
| B. subtilis | 19 |
| B. adolescentis | 20 |
| L. plantarum | 21 |

TABLE 7

Candidate Acetaldehyde-Alcohol/Alcohol Dehydrogenases

| Organism | SEQ ID NO: |
|---|---|
| E. histolytica | 22 |
| B. adolescentis | 23 |

EXAMPLES

Example 1: Construction of Recombinant Yeast Strain Having 2,4-FDCA Pathway Coupled to the Canonical Ethanol Production Pathway and to the Glycerol Production Pathway This example describes the construction of an exemplary yeast cell to demonstrate the in vivo anaerobic co-production of 2,4-FDCA, ethanol and glycerol from sugar feedstocks including, for example, glucose.

The co-production of 2,4-FDCA, ethanol and glycerol in anaerobic conditions is achieved in a recombinant yeast by the pathway shown in FIG. 4, wherein glycerol formation is responsible for maintaining the redox balance.

More specifically, an ethanol producing-yeast strain harboring endogenous glycerol-production pathway is genetically engineered by any methods known in the art to comprise: i) one or more polynucleotides coding for enzymes in a pathway that catalyze a conversion of the sugar feedstock to glyceraldehyde 3-phosphate (G3P) and at least one exogenous nucleic acid molecule encoding a polypeptide that catalyzes the production of 4-hydroxymethylfurfural phosphate from glyceraldehyde 3-phosphate (G3P); ii) at least one nucleic acid molecule encoding a polypeptide that catalyzes the production of 4-hydroxymethylfurfural (4-HMF) from 4-hydroxymethylfurfural phosphate and iii) at least one nucleic acid molecule encoding one or more polypeptides that catalyzes the production of 2,4-furandicarboxylic acid (2,4-FDCA) from 4-HMF, either directly or through production of one or more intermediates.

The parental strain used is FY23 (haploid and isogenic to Saccharomyces cerevisiae S288C) which has a genotype MATa ura3-52 trp1Δ63 leu2Δ1 GAL2+. The microorganism is engineered to harbor at least one copy a gene encoding a (5-formylfuran-3-yl)methyl phosphate synthase that catalyzes the conversion of G3P to (5-formylfuran-3-yl)methyl phosphate. The (5-formylfuran-3-yl)methyl phosphate synthase is classified as EC number 4.2.3.153 and includes enzymes as listed in U.S. Patent Application Publication No. 2021/0238639, which is incorporated by reference herein in its entirety, as well as homologous or similar enzymes. For example, suitable (5-formylfuran-3-yl)methyl phosphate synthase include, but are not limited to, the following enzymes disclosed in U.S. Patent Application Publication No. 2021/0238639: MfnB1, derived from Methanocaldococcus jannaschii; MfnB2, derived from Methanocaldococcus fervens; MfnB3, derived from Methanocaldococcus vulcanius; MfnB4, derived from Methanocaldococcus infernos; MfnB5, derived from Methanothermococcus okinawensis; MfnB6, derived from Methanococcales archaeon HHB; MfnB7, derived from Methanobrevibacter smithii; MfnB8, derived from Methanobacterium sp. PtaB.Bin024; MfnB9, derived from Methanopyrus sp. KOL6; MfnB10, derived from Candidatus Argoarchaeum ethanivorans; MfnB11, derived from Methanobacterium congolense; MfnB12, derived from Methanobrevibacter arboriphilus; MfnB13, derived from Methanococcus maripaludis; MfnB14, derived from Methanococcus vannielii; MfnB15, derived from Methanosarcina acetivorans; MfnB16, derived from Methanosarcina barkeri; MfnB17, derived from Methylorubrum extorquens; MfnB18, derived from Methylobacterium sp.; MfnB19, derived from Methanosarcina mazei; MfnB20, derived from Methyloversatilis universalis; MfnB21, derived from Nitrosocuccus watsonii; MfnB22, derived from Streptomyces cattleya NRRL 8057; MfnB23, derived from Streptomyces coelicolor; MfnB24, derived from Streptomyces EFF88969; MfnB25, derived from Streptomyces griseus; MfnB26, derived from Streptomyces sp. DH-12; and MfnB27, derived from Streptomyces venezuelae.

Preferably, the (5-formylfuran-3-yl)methyl phosphate synthase is MfnB1, derived from Methanocaldococcus jannaschii. Suitable methods for expressing and purifying (5-formylfuran-3-yl)methyl phosphate synthases include, but are not limited to, the methods disclosed in Example 1 of U.S. Patent Application Publication No. 2021/0238639, which is incorporated by reference herein. Suitable methods for assessing the activity of (5-formylfuran-3-yl)methyl phosphate synthases include, but are not limited to, the methods disclosed in Example 2 of U.S. Patent Application Publication No. 2021/0238639, which is incorporated by reference herein. Additionally, the microorganism is modified to overexpress one or more endogenous phosphatases, which catalyze the conversion of 4-hydroxymethylfurfural phosphate to 4-HMF. Preferably, the overexpressed phosphatase is classified as a haloacid dehalogenase. Alternatively, the microorganism is modified to comprise at least one copy of an exogenous gene coding for a phosphatase, for example, wherein the phosphatase is derived from Streptomyces coelicolor or Escherichia coli. Such microorganism is modified to further contain one or more genes encoding dehydrogenases that are capable of oxidizing the 4-HMF to 2,4-FDCA (directly or through the production of intermediates). The dehydrogenase is an alcohol dehydrogenase classified as EC number 1.1.1 or an aldehyde dehydrogenase classified as EC number 1.2.1. Alternatively, the microorganism contains a combination of an alcohol dehydrogenase with an aldehyde dehydrogenase. Suitable alcohol dehydrogenases and aldehyde dehydrogenases include those disclosed in U.S. Patent Application Publication No. 2021/0238639, which is incorporated by reference herein in its entirety, as well as homologous or similar enzymes. For example, suitable alcohol dehydrogenases and aldehyde dehydrogenases include, but are not limited to, the following enzymes disclosed in U.S. Patent Application Publication No. 2021/0238639: DH1, derived from *Zymomonas mobilis*; DH2, derived from *Zymomonas mobilis* subsp. *pomaceae* ATCC 29192; DH3, derived from *Shewanella baltica*; DH4, derived from *Burkholderia pseudomallei*; DH5, derived from *Saccharomyces cerevisiae*; DH6, derived from *Saccharomyces cerevisiae*; DH7, derived from *Pseudomonas putida*; DH8, derived from *Pseudomonas putida*; DH9, derived from *Pseudomonas* sp. NBRC 111139; DH10, derived from *Pseudomonas* sp. JUb52; and DH11, derived from *Pseudomonas citronellohs*. Preferably, the alcohol dehydrogenase is DH6 derived from *S. cerevisiae* and is combined with the aldehyde dehydrogenase DH8, derived from *Pseudomonas putida*.

Example 2: Construction of Recombinant Yeast Strain Having 2,4-FDCA Pathway Coupled to the Calvin Cycle Enzymes and to the Canonical Ethanol Production Pathway This example describes the construction of an exemplary yeast cell to demonstrate the in vivo anaerobic co-production of 2,4-FDCA and ethanol from sugar feedstocks including, for example, glucose.

The co-production of 2,4-FDCA and ethanol in anaerobic conditions is achieved in a recombinant yeast by the pathway shown in FIG. 1, wherein $CO_2$ generated in the canonical ethanol production pathway is used as an electron acceptor for NADH oxidation by coupling 2,4-FDCA pathway with the Calvin cycle enzymes phosphoribulokinase (PRK) and ribulose-1,5-bisphosphate carboxylase (RuBisCo).

The Calvin cycle is the primary pathway for carbon fixation in most plants, algae and various autotrophic microorganisms (Hatch et al., Annual Review of Plant Physiology (1970), 21(1): 141-162). It comprises a series of biochemical reactions, including the production of ribulose-1,5-bisphosphate from ribulose-5-phosphate by a phosphoribulokinase (PRK) and the conversion of $CO_2$ and ribulose-1,5-bisphosphate to two molecules of glycerate-3-phosphate by a ribulose-1,5-bisphosphate carboxylase (RuBisCO). The co-expression of PRK and RuBisCo in *S. cerevisiae* has been reported (Guadalupe-Medina et al., Biotechnology for Biofuels (2013) 6:125) and Papapetridis et al., Biotechnology for Biofuels (2018), 11:17). In this example, the Calvin cycle is used as a pathway to enable reoxidation of NADH.

More specifically, the recombinant yeast strain described in Example 1 (co-producing 2,4-FDCA, ethanol and glycerol) is genetically engineered by any methods known in the art to further comprise: i) at least one nucleic acid molecule encoding a polypeptide that catalyzes the production of ribulose-1,5-bisphosphate from ribulose-5-phosphate and ii) at least one nucleic acid molecule encoding a polypeptide that catalyzes the production of two molecules of glycerate-3-phosphate from the combination of $CO_2$ with ribulose-1,5-bisphosphate.

The microorganism is engineered to harbor at least one copy of the gene encoding a phosphoribulokinase (PRK), that catalyzes the conversion of ribulose-5-phosphate to ribulose-1,5-bisphosphate. The PRK is classified as EC number 2.7.1.19 and includes, but is not limited to, enzymes as listed in Table 1, as well as homologous or similar enzymes. Preferably, the phosphoribulokinase (sPRK) is SEQ ID NO: 1, derived from *Spinacia oleracea*. Furthermore, the microorganism is modified to have a ribulose-1,5-bisphosphate carboxylase (RuBisCO), selected from Form I, Form II, Form III, or a combination thereof. The RuBisCO is classified as EC number 4.1.1.39 and includes, but is not limited to, enzymes as listed in Tables 2, 3 and 4, as well as homologous or similar enzymes. Preferably, the RuBisCO is RuBisCO Form I (cbbL/cbbS) derived from *Cupriavidus necator*. Optionally, such microorganism may further contain at least one gene encoding a chaperone protein, preferably wherein chaperone protein is GroEL/GroES derived from *E. coli*.

It is well-known in the art that ethanol producing-yeast, for example *S. cerevisiae*, harbor an endogenous glycerol production-pathway, wherein glycerol is a required end-product of yeast ethanolic fermentation due to its redox imbalance in anaerobic conditions (Bakker et al., FEMS Microbiology Reviews (2001), 25(1):15-37). Therefore, although coupling 2,4-FDCA pathway, ethanol production pathway and Calvin cycle enzymes may provide redox-cofactor balanced pathways for anaerobic production (reducing or even eliminating the need of glycerol formation to act as electron sink), the recombinant yeast of this example still produces reduced amounts of glycerol in addition to 2,4-FDCA and ethanol.

Example 3: Construction of Recombinant Yeast Strain Having 2,4-FDCA Pathway Coupled to the Phosphoketolase Pathway and to the Canonical Ethanol Production Pathway This example describes the construction of an exemplary yeast cell to demonstrate the in vivo anaerobic co-production of 2,4-FDCA and ethanol from sugar feedstocks including, for example, glucose.

The co-production of 2,4-FDCA and ethanol in anaerobic conditions is achieved in a recombinant yeast described in Example 1 by the pathway shown in FIG. 2, wherein ethanol production by phosphoketolase pathway is used for NADH oxidation and coupled with 2,4-FDCA pathway. Phosphoketolase pathway consists of phosphoketolase (Pk), phosphotransacetylase (Pta) and acetaldehyde dehydrogenase (AlDH) enzymes. Phosphoketolases convert the pentose phosphate pathway intermediate xylulose-5P to acetyl-P plus glyceraldehyde-3P (E.C. 4.1.2.9) and/or the glycolytic intermediate fructose-6P to acetyl-P plus erythrose-4P (E.C. 4.1.2.22), considering that most of them exhibit dual substrate specificity. Suitable phosphoketolases include, but are not limited to, the phosphoketolases listed in Table 5, as well as homologous or similar enzymes. Preferably, the phosphoketolase is SEQ ID NO: 16 derived from *Bifidobacterium breve*.

Phosphotransacetylases convert acetyl-P to acetyl-CoA plus inorganic phosphate without any energy input. Suitable phosphotransacetylases include, but are not limited to, the phosphotransacetylases listed in Table 6, as well as homologous or similar enzymes. Preferably, the phosphotransacetylase is SEQ ID NO: 19 derived from *Bacillus subtilis*.

Acetaldehyde dehydrogenase converts acetyl-CoA to acetaldehyde. Acetaldehyde is further converted to ethanol by endogenous alcohol dehydrogenases. Suitable acetaldehyde dehydrogenases include, but are not limited to, acetaldehyde dehydrogenases listed in Table 7, as well as homologous or similar enzymes. Preferably, the acetaldehyde dehydrogenase is SEQ ID NO: 22 derived from *Entamoeba histolytica*.

More specifically, the recombinant yeast from Example 1 is genetically engineered by any methods in the art to comprise: i) one or more polynucleotides coding for enzymes in a pathway that catalyze a conversion of the fermentable carbon source to xylulose-5P or fructose-6P; ii) one or more polynucleotides coding for enzymes that catalyze the conversion of xylulose-5P to acetyl-P plus glyceraldehyde-3P or fructose-6P to acetyl-P and erythrose-4P; iii) one or more polynucleotides coding for enzymes that catalyze the conversion of acetyl-P to acetyl-CoA and inorganic phosphate and iv) one or more polynucleotides coding for enzymes that catalyze the conversion of acetyl-CoA to acetaldehyde.

The microorganism is modified to decrease acetate formation from acetaldehyde through deletion or attenuation of alcohol dehydrogenase 6 (Adh6). Furthermore, the microorganism is modified to decrease acetate formation from acetyl-P through deletion or attenuation of glycerol-3-phosphate phosphatases GPP1 and/or GPP2.

Therefore, co-expression of phosphoketolase pathway and 2,4-FDCA pathway enables redox balance in *S. cerevisiae* and consequently co-production of 2,4-FDCA and ethanol from glucose or other fermentative sources cultivated in anaerobic conditions.

Example 4: Construction of Recombinant Glycerol-Null Yeast Strain Having 2,4-FDCA Pathway Coupled to the Calvin-Cycle Enzymes and to the Canonical Ethanol Production Pathway This example describes the construction of an exemplary yeast cell to demonstrate the in vivo anaerobic co-production of 2,4-FDCA and ethanol, wherein glycerol production is significantly reduced or eliminated.

The anaerobic co-production of 2,4-FDCA and ethanol from sugar feedstocks including, for example, glucose, is achieved in a recombinant yeast described in Example 2 by deletion of glycerol-production pathway.

The glycerol-production pathway includes glycerol-3-phosphate dehydrogenases (GPD1 and GPD2) and glycerol-3-phosphate phosphatases (GPP1 and GPP2). Glycerol-3-phosphate dehydrogenases convert dihydroxyacetone-phosphate and NADH to glycerol-3-phosphate and $NAD^+$. GPD1 is classified as E.C. number 1.1.1.8 and GPD2 is classified as E.C. number 1.1.5.3. Glycerol-3-phosphate phosphatases GPP1 and GPP2 convert glycerol-3-phosphate to glycerol and are classified as E.C. number 3.1.3.21.

More specifically, the recombinant yeast from Example 2 is genetically engineered by any methods in the art to comprise deletion of GPD1 and GPD2.

Using this microorganism, 2,4-FDCA and ethanol are anaerobically co-produced from glucose or other fermentative sources with significantly reduced or no glycerol formation. Therefore, coupling 2,4-FDCA pathway, ethanol production pathway and Calvin cycle enzymes will provide redox-cofactor balanced pathways for anaerobic production.

Example 5: Construction of Recombinant Glycerol-Null Yeast Strain Having 2,4-FDCA Pathway Coupled to the Phosphoketolase Pathway and to the Canonical Ethanol Production Pathway This example describes the construction of an exemplary yeast cell to demonstrate the in vivo anaerobic co-production of 2,4-FDCA and ethanol, wherein glycerol production is significantly reduced or eliminated.

The anaerobic co-production of 2,4-FDCA and ethanol from sugar feedstocks including, for example, glucose, is achieved in a recombinant yeast described in Example 3 by deletion of a glycerol-production pathway.

The glycerol-production pathway includes glycerol-3-phosphate dehydrogenases (GPD1 and GPD2) and glycerol-3-phosphate phosphatases (GPP1 and GPP2). Glycerol-3-phosphate dehydrogenases convert dihydroxyacetone-phosphate and NADH to glycerol-3-phosphate and $NAD^+$. GPD1 is classified as E.C. number 1.1.1.8 and GPD2 is classified as E.C. number 1.1.5.3. Glycerol-3-phosphate phosphatases GPP1 and GPP2 convert glycerol-3-phosphate to glycerol and are classified as E.C. number 3.1.3.21.

More specifically, the recombinant yeast from example 3 is genetically engineered by any methods in the art to comprise deletion of GPD1 and GPD2.

Using this microorganism, 2,4-FDCA and ethanol are anaerobically co-produced from glucose or other fermentative sources with significantly reduced or no glycerol formation. Therefore, coupling 2,4-FDCA pathway, ethanol production pathway and phosphoketolase pathway provides redox-cofactor balanced pathways for anaerobic production.

Example 6: Anaerobic Co-Production of 2,4-FDCA and Ethanol

This example describes an exemplary method to demonstrate the co-production of 2,4-FDCA and ethanol in anaerobic conditions where the recombinant yeasts described in Examples 4 and 5 are used to ferment a sugar feedstock.

Precultures of the recombinant yeast strains described either in Examples 4 and 5 are prepared by inoculating a single colony of each strain in YP (Yeast Extract Peptone) medium with addition of 2% w/w glucose, at 30° C. and 210 rpm. After 18 hours of incubation, cells are harvested by centrifugation and washed with synthetic fermentation medium.

Batch anaerobic fermentation is carried out in 250 mL screw cap flasks equipped with ports for aseptic sampling and nitrogen injection. Oxygen permeation is mitigated by using norprene tubing and by injection of high purity nitrogen (<0.5 ppm oxygen) after inoculation and sampling. Synthetic fermentation medium comprises, for example $(NH_4)_2SO_4$, 5.0 g/L, $CaCl_2$), 0.1 g/L, NaCl, 0.1 g/L, $MgSO_4$, 0.5 g/L, $KH_2PO_4$, 1.0 g/L, biotin, 2.0 µg/L, calcium pantothenate, 400 µg/L, folic acid, 2.0 µg/L, inositol, 2.0 mg/L, nicotinic acid, 400 µg/L, p-aminobenzoic acid, 200 µg/L, pyridoxine HCl, 400 µg/L, riboflavin, 200 µg/L, thiamine HCl, 400 µg/L, boric acid, 500 µg/L, copper sulphate, 40 µg/L, potassium iodide, 100 µg/L, ferric chloride, 200 µg/L, manganese sulphate, 400 µg/L, sodium molybdate, 200 µg/L, and zinc sulphate, 400 µg/L. Amino acids may be supplemented as 1.62 g/L of Yeast Synthetic Drop-out Medium Supplements—without the appropriate amino acid (depending on the auxotrophic marker harbored by the yeast strain). Ergosterol (0.01 g/L) and Tween 80 (0.42 g/L) are supplemented as anaerobic growth factors.

The fermentation systems containing 100 mL of culture media and 1% inoculum ratio are incubated at 30° C. and 210 rpm until carbon source depletion. Periodic samples are taken throughout the assay. The main fermentation metabolites, including glycerol and ethanol, are quantified by HPLC-IR (Thermo Ultimate 3000) using Bio-Rad Aminex HPX-87H column (50° C., $H_2SO_4$ 5 mM at 1 mL/min, isocratic gradient mode). 2,4-FDCA can be identified using HPLC-DAD (Thermo Ultimate 3000) equipped with an Aminex HPX-87H (Bio-Rad). The column is maintained at 50° C. The mobile phase used is a 5 mM H2SO4 solution with flow rate of 0.75 mL/min and isocratic gradient mode. 2,4-FDCA is detected at 245 nm. The recombinant yeast strains grown under the anaerobic conditions described above are able to co-produce ethanol and 2,4-FDCA, besides showing significant reduction on glycerol production.

NUMBERED EMBODIMENTS

Embodiment 1. A recombinant microorganism comprising:
(a) at least one nucleic acid molecule encoding a polypeptide that catalyzes the production of 4-hydroxymethylfurfural phosphate from glyceraldehyde 3-phosphate (G3P);
(b) at least one nucleic acid molecule encoding a polypeptide that catalyzes the production of 4-hydroxymethylfurfural (4-HMF) from 4-hydroxymethylfurfural phosphate;
(c) at least one nucleic acid molecule encoding one or more polypeptides that catalyze the production of 2,4-furandicarboxylic acid (2,4-FDCA) from 4-HMF, either directly or through production of one or more intermediates;
(d) at least one nucleic acid molecule encoding a polypeptide that catalyzes the production of ribulose-1,5-bisphosphate from ribulose-5-phosphate; and
(e) at least one nucleic acid molecule encoding a polypeptide that catalyzes the production of two molecules of glycerate-3-phosphate from the combination of $CO_2$ with ribulose-1,5-bisphosphate.

Embodiment 2. The recombinant microorganism of embodiment 1, wherein the intermediates are furan-2,4-dicarbaldehyde, 4-(hydroxymethyl)furoic acid, 4-formylfuran-2-carboxylate, 4-formylfuran-2-carboxylate, and/or 2-formylfuran-4-carboxylate.

Embodiment 3. The recombinant microorganism of embodiment 1 or 2, wherein the polypeptide that catalyzes the production of ribulose-1,5-bisphosphate from ribulose-5-phosphate is a phosphoribulokinase (PRK).

Embodiment 4. The recombinant microorganism of any one of embodiments 1 to 3, wherein the polypeptide that catalyzes the production of glycerate-3-phosphate from the combination of $CO_2$ with ribulose-1,5-bisphosphate is a ribulose-1,5-bisphosphate carboxylase (RuBisCO).

Embodiment 5. The recombinant microorganism of embodiment 4, wherein the RuBisCO is selected from Form I, Form II, Form III, or a combination thereof.

Embodiment 6. The recombinant microorganism of any one of embodiments 1 to 5, further comprising at least one nucleic acid molecule encoding a chaperone protein.

Embodiment 7. The recombinant microorganism of any one of embodiments 1 to 6, wherein the microorganism utilizes NADH and/or NADPH produced as a byproduct of 2,4-FDCA production to produce ethanol.

Embodiment 8. A recombinant microorganism comprising:
(a) at least one nucleic acid molecule encoding a polypeptide that catalyzes the production of 4-hydroxymethylfurfural phosphate from glyceraldehyde 3-phosphate (G3P);
(b) at least one nucleic acid molecule encoding a polypeptide that catalyzes the production of 4-hydroxymethylfurfural (4-HMF) from 4-hydroxymethylfurfural phosphate;
(c) at least one nucleic acid molecule encoding one or more polypeptides that catalyze the production of 2,4-furandicarboxylic acid (2,4-FDCA) from 4-HMF, either directly or through production of intermediates;
(d) at least one nucleic acid molecule encoding a polypeptide that catalyzes the production of acetyl phosphate and D-glyceraldehyde-3-phosphate from D-xylulose-5-phosphate and phosphate, and/or at least one nucleic acid molecule encoding a polypeptide that catalyzes the production of acetyl phosphate and erythrose-4-phosphate from fructose-6-phosphate and phosphate;
(e) at least one nucleic acid molecule encoding one or more polypeptides that catalyze:
(1) the production of acetyl-CoA from acetyl phosphate and free coenzyme A; and/or
(2) the production of acetate from acetyl phosphate and the production of acetyl-CoA from acetate; and
(f) at least one nucleic acid molecule encoding one or more polypeptides that catalyze:
(1) the production of acetaldehyde from acetyl-CoA; and/or
(2) the production of ethanol from acetyl-CoA.

Embodiment 9. The recombinant microorganism of embodiment 8, wherein the intermediates are furan-2,4-dicarbaldehyde, 4-(hydroxymethyl)furoic acid, 4-formylfuran-2-carboxylate, 4-formylfuran-2-carboxylate, and/or 2-formylfuran-4-carboxylate.

Embodiment 10. The recombinant microorganism of embodiment 8 or 9, further comprising at least one genetic modification that leads to a down-regulation or a deletion of an enzyme in a glycerol-production pathway.

Embodiment 11. The recombinant microorganism of embodiment 10, wherein the enzyme in the glycerol-production pathway is a glycerol-3-phosphate dehydrogenase, preferably wherein the glycerol-3-phosphate dehydrogenase is classified as EC number 1.1.1.8.

Embodiment 12. The recombinant microorganism of embodiment 10 or 11, wherein the enzyme in the glycerol-production pathway is a glycerol-3-phosphate phosphatase, preferably wherein the glycerol-3-phosphate phosphatase is classified as EC number 3.1.3.21. Embodiment 13. The recombinant microorganism of any one of embodiments 8 to 12, wherein the polypeptide that catalyzes the production of acetyl phosphate and D-glyceraldehyde-3-phosphate from D-xylulose-5-phosphate and phosphate is a phosphoketolase, preferably wherein the phosphoketolase is classified as EC number 4.1.2.9.

Embodiment 14. The recombinant microorganism of any one of embodiments 8 to 12, wherein the polypeptide that catalyzes the production of acetyl phosphate and erythrose-4-phosphate from fructose-6-phosphate and phosphate is a phosphoketolase, preferably wherein the phosphoketolase is classified as EC number 4.1.2.22.

Embodiment 15. The recombinant microorganism of embodiment 13 or 14, wherein the phosphoketolase is a single-specificity phosphoketolase.

Embodiment 16. The recombinant microorganism of embodiment 13 or 14, wherein the phosphoketolase is a dual-specificity phosphoketolase.

Embodiment 17. The recombinant microorganism of any one of embodiments 8 to 16, wherein the polypeptide that catalyzes the production of acetyl-CoA from acetyl phosphate and free coenzyme A is a phosphotransacetylase, preferably wherein the phosphotransacetylase is classified as EC number 2.3.1.8.

Embodiment 18. The recombinant microorganism of any one of embodiments 8 to 16, wherein the polypeptide that catalyzes the production of acetate from acetyl phosphate is an acetate kinase, preferably wherein the acetate kinase is classified as EC number 2.7.2.12. Embodiment 19. The recombinant microorganism of any one of embodiments 8 to 16 or 18, wherein the polypeptide that catalyzes the production of acetyl-CoA from acetate is an acetyl-CoA synthetase or an acetate-CoA ligase, preferably wherein the acetyl-CoA synthetase or an acetate-CoA ligase is classified as EC number 6.2.1.1.

Embodiment 20. The recombinant microorganism of any one of embodiments 8 to 19, wherein the polypeptide that catalyzes the production of acetaldehyde from acetyl-CoA is an acetaldehyde dehydrogenase.

Embodiment 21. The recombinant microorganism of any one of embodiments 8 to 20, wherein the polypeptide that catalyzes the production of ethanol from acetaldehyde is an alcohol dehydrogenase.

Embodiment 22. The recombinant microorganism of any one of embodiments 8 to 19, wherein the polypeptide that catalyzes the production of ethanol from acetyl-CoA is a bifunctional acetaldehyde-alcohol dehydrogenase.

Embodiment 23. The recombinant microorganism of embodiment 22, wherein the bifunctional acetaldehyde-alcohol dehydrogenase is selected from enzymes classified as both EC number 1.2.1.10 and EC number 1.1.1.1.

Embodiment 24. The recombinant microorganism of embodiment 22, wherein the bifunctional acetaldehyde-alcohol dehydrogenase is an NADH- and/or NADPH-dependent bifunctional acetaldehyde-alcohol dehydrogenase, preferably wherein the NADH- and/or NADPH-dependent bifunctional acetaldehyde-alcohol dehydrogenase is selected from enzymes classified as EC number 1.2.1.10 or EC number 1.1.1.2.

Embodiment 25. The recombinant microorganism of any one of embodiments 8 to 24, further comprising at least one genetic modification that leads to an up-regulation of an enzyme in a non-oxidative pentose phosphate pathway.

Embodiment 26. The recombinant microorganism of embodiment 25, wherein the enzyme in the non-oxidative pentose phosphate pathway is a transaldolase, preferably wherein the transaldolase is classified as EC number 2.2.1.2.

Embodiment 27. The recombinant microorganism of embodiment 25 or 26, wherein the enzyme in the non-oxidative pentose phosphate pathway is a transketolase, preferably wherein the transketolase is classified as EC number 2.2.1.1.

Embodiment 28. The recombinant microorganism of any one of embodiments 25 to 27, wherein the enzyme in the non-oxidative pentose phosphate pathway is a ribose-5-phosphate isomerase, preferably wherein the ribose-5-phosphate isomerase is classified as EC number 5.3.1.6.

Embodiment 29. The recombinant microorganism of any one of embodiments 25 to 28, wherein the enzyme in the non-oxidative pentose phosphate pathway is a ribulose-5-phosphate 3-epimerase, preferably wherein the ribulose-5-phosphate 3-epimerase is classified as EC number 5.1.3.1.

Embodiment 30. The recombinant microorganism of any one of embodiments 8 to 29, wherein the microorganism utilizes NADH and/or NADPH produced as a byproduct of 2,4-FDCA production to produce ethanol.

Embodiment 31. A recombinant microorganism comprising:
(a) at least one nucleic acid molecule encoding a polypeptide that catalyzes the production of 4-hydroxymethylfurfural phosphate from glyceraldehyde 3-phosphate (G3P);
(b) at least one nucleic acid molecule encoding a polypeptide that catalyzes the production of 4-hydroxymethylfurfural (4-HMF) from 4-hydroxymethylfurfural phosphate;
(c) at least one nucleic acid molecule encoding one or more polypeptides that catalyze the production of 2,4-furandicarboxylic acid (2,4-FDCA) from 4-HMF, either directly or through production of intermediates;
(d) at least one nucleic acid molecule encoding a polypeptide that catalyzes the production of oxaloacetate from phosphoenol pyruvate (PEP);
(e) at least one nucleic acid molecule encoding one or more polypeptides that catalyze:
(1) the production of malonate semialdehyde from oxaloacetate; and/or
(2) the production of aspartate from oxaloacetate, the production of β-alanine from aspartate, and the production of malonate semialdehyde from β-alanine;
(f) at least one nucleic acid molecule encoding a polypeptide that catalyzes the production of 3-hydroxypropionic acid (3-HP) from malonate semialdehyde;
(g) at least one nucleic acid molecule encoding one or more polypeptides that catalyze the production of propionyl-CoA from 3-HP; and
(h) at least one nucleic acid molecule encoding a polypeptide that catalyzes the production of 1-propanol from propionyl-CoA; and/or at least one nucleic acid molecule encoding one or more polypeptides that catalyze the production of propionaldehyde from propionyl-CoA and the production of 1-propanol from propionaldehyde.

Embodiment 32. The recombinant microorganism of embodiment 31, wherein the intermediates are furan-2,4-dicarbaldehyde, 4-(hydroxymethyl)furoic acid, 4-formylfuran-2-carboxylate, 4-formylfuran-2-carboxylate, and/or 2-formylfuran-4-carboxylate.

Embodiment 33. The recombinant microorganism of embodiment 31 or 32, wherein the polypeptide that catalyzes the production of aspartate from oxaloacetate is an aspartate amino transferase.

Embodiment 34. The recombinant microorganism of any one of embodiments 31 to 33, wherein the polypeptide that catalyzes the production of β-alanine from aspartate is an aspartate decarboxylase.

Embodiment 35. The recombinant microorganism of any one of embodiments 31 to 34, wherein the polypeptide that catalyzes the production of malonate semialdehyde from β-alanine is a β-alanine pyruvate amino transferase and/or a β-alanine transaminase.

Embodiment 36. The recombinant microorganism of any one of embodiments 31 to 35, wherein the polypeptide that catalyzes the production of 3-HP from malonate semialdehyde is a 3-hydroxypropionic acid dehydrogenase.

Embodiment 37. The recombinant microorganism of any one of embodiments 31 to 36, wherein the polypeptide that catalyzes the production of propionyl-CoA from 3-HP is a propionyl-CoA synthase.

Embodiment 38. The recombinant microorganism of any one of embodiments 31 to 36, wherein the polypeptides that catalyze the production of propionyl-CoA from 3-HP are a 3-hydroxypropionyl-CoA synthetase/transferase, a 3-hydroxypropionyl-CoA dehydratase, and an acrylyl-CoA reductase.

Embodiment 39. The recombinant microorganism of any one of embodiments 31 to 38, wherein the polypeptide that catalyzes the production of 1-propanol from propionyl-CoA is an alcohol/aldehyde dehydrogenase.

Embodiment 40. The recombinant microorganism of any one of embodiments 31 to 39, wherein the polypeptide that catalyzes the production of propionaldehyde from propionyl-CoA is an aldehyde dehydrogenase (acetylating).

Embodiment 41. The recombinant microorganism of any one of embodiments 31 to 40, wherein the polypeptide that catalyzes the production of 1-propanol from propionaldehyde is an alcohol dehydrogenase.

Embodiment 42. The recombinant microorganism of any one of embodiments 31 to 41, wherein the microorganism utilizes NADH and/or NADPH produced as a byproduct of 2,4-FDCA production to produce ethanol.

Embodiment 43. The recombinant microorganism of any one of the preceding embodiments, wherein the microorganism is selected from a bacterium, a fungus, or a yeast.

Embodiment 44. A method of co-producing 2,4-FDCA and ethanol comprising: contacting the recombinant microorganism of any one of the preceding embodiments with a fermentable carbon source under conditions sufficient to produce 2,4-FDCA and ethanol.

Embodiment 45. The method of embodiment 44, wherein the recombinant microorganism produces a molar ratio of ethanol:2,4-FDCA of greater than 1:1, such as greater than 2:1, greater than 3:1, or greater than 4:1.

Embodiment 46. The method of embodiment 44 or 45, wherein the recombinant microorganism further produces 1-propanol.

Embodiment 47. The method of any one of embodiments 44 to 46, wherein the conditions comprise anaerobic conditions.

Embodiment 48. A method of co-producing 2,4-FDCA and ethanol in a recombinant microorganism comprising:

(a) converting glyceraldehyde 3-phosphate (G3P) to 4-hydroxymethylfurfural phosphate;

(b) converting 4-hydroxymethylfurfural phosphate to 4-hydroxymethylfurfural (4-HMF);

(c) converting 4-HMF to 2,4-furandicarboxylic acid (2,4-FDCA), either directly or through production of one or more intermediates;

(d) converting ribulose-5-phosphate to ribulose-1,5-bisphosphate; and (e) converting $CO_2$ and ribulose-1,5-bisphosphate to two molecules of glycerate-3-phosphate.

Embodiment 49. The method of embodiment 45, further comprising converting NADH and/or NADPH produced as a byproduct of 2,4-FDCA production and glycerate-3-phosphate to ethanol.

Embodiment 50. The method of embodiment 48 or 49, wherein glyceraldehyde 3-phosphate (G3P) is converted to 4-hydroxymethylfurfural phosphate with a methyl phosphate synthase; 4-hydroxymethylfurfural phosphate is converted to 4-hydroxymethylfurfural (4-HMF) with a phosphatase or a kinase; ribulose-5-phosphate is converted to ribulose-1,5-bisphosphate with a phosphoribulokinase; and $CO_2$ and ribulose-1,5-bisphosphate are converted to two molecules of glycerate-3-phosphate with a RiBisCO.

Embodiment 51. A method of co-producing 2,4-FDCA, 1-propanol, and ethanol in a recombinant microorganism comprising:

(a) converting glyceraldehyde 3-phosphate (G3P) to 4-hydroxymethylfurfural phosphate;

(b) converting 4-hydroxymethylfurfural phosphate to 4-hydroxymethylfurfural (4-HMF);

(c) converting 4-HMF to 2,4-furandicarboxylic acid (2,4-FDCA), either directly or through production of intermediates;

(d) converting phosphoenol pyruvate (PEP) to oxaloacetate;

(e) converting oxaloacetate to malonate semialdehyde; and/or converting oxaloacetate to aspartate, aspartate to β-alanine, and β-alanine to malonate semialdehyde;

(f) converting malonate semialdehyde to 3-hydroxypropionic acid (3-HP);

(g) converting 3-HP to propionyl-CoA; and (h) converting propionyl-CoA to 1-propanol; and/or converting propionyl-CoA to propionaldehyde and propionaldehyde to 1-propanol.

Embodiment 52. The method of embodiment 51, further comprising converting NADH and/or NADPH produced as a byproduct of 2,4-FDCA production to ethanol.

Embodiment 53. The method of embodiment 51 or 52, wherein glyceraldehyde 3-phosphate (G3P) is converted to 4-hydroxymethylfurfural phosphate with a methyl phosphate synthase; 4-hydroxymethylfurfural phosphate is converted to 4-hydroxymethylfurfural (4-HMF) with a phosphatase or a kinase; phosphoenol pyruvate (PEP) is converted to oxaloacetate with a phosphoenol pyruvate carboxylase and/or a phosphoenol pyruvate carboxykinase; oxaloacetate is converted to asparate with an aspartate amino transferase; aspartate is converted to β-alanine with an aspartate decarboxylase; β-alanine is converted to malonate semialdehyde with a β-alanine pyruvate amino transferase and/or a β-alanine transaminase; malonate semialdehyde is converted to 3-hydroxypropionic acid (3-HP) with a 3-hydroxypropionic acid dehydrogenase; 3-HP is converted to propionyl-CoA with a propionyl-CoA synthase, and/or 3-HP is converted to propionyl-CoA with a 3-hydroxypropionyl-CoA synthetase/transferase, a 3-hydroxypropionyl-CoA dehydratase, and an acrylyl-CoA reductase; and propionyl-CoA is converted to 1-propanol with an alcohol/aldehyde dehydrogenase, and/or propionyl-CoA is converted to propionaldehyde with an aldehyde dehydrogenase (acetylating) and propionaldehyde is converted to 1-propanol with an alcohol dehydrogenase.

Embodiment 54. A method of producing a recombinant microorganism capable of producing 2,4-FDCA, the method comprising introducing into and/or overexpressing in the recombinant microorganism the following:

(a) at least one nucleic acid molecule encoding a polypeptide that catalyzes the production of 4-hydroxymethylfurfural phosphate from glyceraldehyde 3-phosphate (G3P);

(b) at least one nucleic acid molecule encoding a polypeptide that catalyzes the production of 4-hydroxymethylfurfural (4-HMF) from 4-hydroxymethylfurfural phosphate;

(c) at least one nucleic acid molecule encoding one or more polypeptides that catalyze the production of 2,4-furandicarboxylic acid (2,4-FDCA) from 4-HMF, either directly or through production of intermediates, wherein the intermediates are preferably furan-2,4-dicarbaldehyde, 4-(hydroxymethyl)furoic acid, 4-formylfuran-2-carboxylate, 4-formylfuran-2-carboxylate, and/or 2-formylfuran-4-carboxylate;

(d) at least one nucleic acid molecule encoding a polypeptide that catalyzes the production of ribulose-1,5-bisphosphate from ribulose-5-phosphate; and (e) at least one nucleic acid molecule encoding a polypeptide that catalyzes the production of two molecules of glycerate-3-phosphate from the combination of $CO_2$ with ribulose-1,5-bisphosphate.

Embodiment 55. A method of producing a recombinant microorganism capable of producing 2,4-FDCA, the method comprising introducing into and/or overexpressing in the recombinant microorganism the following:

(a) at least one nucleic acid molecule encoding a polypeptide that catalyzes the production of 4-hydroxymethylfurfural phosphate from glyceraldehyde 3-phosphate (G3P);

(b) at least one nucleic acid molecule encoding a polypeptide that catalyzes the production of 4-hydroxymethylfurfural (4-HMF) from 4-hydroxymethylfurfural phosphate;

(c) at least one nucleic acid molecule encoding one or more polypeptides that catalyze the production of 2,4- furandicarboxylic acid (2,4-FDCA) from 4-HMF, either directly or through production of intermediates, wherein the intermediates are preferably furan-2,4-dicarbaldehyde, 4-(hydroxymethyl)furoic acid, 4-formylfuran-2-carboxylate, 4-formylfuran-2-carboxylate, and/or 2-formylfuran-4-carboxylate;

(d) at least one nucleic acid molecule encoding a polypeptide that catalyzes the production of acetyl phosphate and D-glyceraldehyde-3-phosphate from D-xylulose-5-phosphate and phosphate, and/or at least one nucleic acid molecule encoding a polypeptide that catalyzes the production of acetyl phosphate and erythrose-4-phosphate from fructose-6-phosphate and phosphate;

(e) at least one nucleic acid molecule encoding one or more polypeptides that catalyze:
 (1) the production of acetyl-CoA from acetyl phosphate and free coenzyme A; and/or
 (2) the production of acetate from acetyl phosphate and the production of acetyl-CoA from acetate; and (f) at least one nucleic acid molecule encoding one or more polypeptides that catalyze:
 (1) the production of acetaldehyde from acetyl-CoA, and/or the production of ethanol from acetaldehyde; and/or
 (2) the production of ethanol from acetyl-CoA.

Embodiment 56. A method of producing a recombinant microorganism capable of producing 2,4-FDCA, the method comprising introducing into and/or overexpressing in the recombinant microorganism the following:

(a) at least one nucleic acid molecule encoding a polypeptide that catalyzes the production of 4-hydroxymethylfurfural phosphate from glyceraldehyde 3-phosphate (G3P);

(b) at least one nucleic acid molecule encoding a polypeptide that catalyzes the production of 4-hydroxymethylfurfural (4-HMF) from 4-hydroxymethylfurfural phosphate;

(c) at least one nucleic acid molecule encoding one or more polypeptides that catalyze the production of 2,4-furandicarboxylic acid (2,4-FDCA) from 4-HMF, either directly or through production of intermediates, wherein the intermediates are preferably furan-2,4-dicarbaldehyde, 4-(hydroxymethyl)furoic acid, 4-formylfuran-2-carboxylate, 4-formylfuran-2-carboxylate, and/or 2-formylfuran-4-carboxylate;

(d) at least one nucleic acid molecule encoding a polypeptide that catalyzes the production of oxaloacetate from phosphoenol pyruvate (PEP);

(e) at least one nucleic acid molecule encoding one or more polypeptides that catalyze:
 (1) the production of malonate semialdehyde from oxaloacetate; and/or
 (2) the production of aspartate from oxaloacetate, the production of β-alanine from aspartate, and the production of malonate semialdehyde from β-alanine;

(f) at least one nucleic acid molecule encoding a polypeptide that catalyzes the production of 3-hydroxypropionic acid (3-HP) from malonate semialdehyde;

(g) at least one nucleic acid molecule encoding one or more polypeptides that catalyze the production of propionyl-CoA from 3-HP; and (h) at least one nucleic acid molecule encoding a polypeptide that catalyzes the production of 1-propanol from propionyl-CoA; and/or at least one nucleic acid molecule encoding one or more polypeptides that catalyze the production of propionaldehyde from propionyl-CoA and the production of 1-propanol from propionaldehyde.

Embodiment 57. A method of producing a polymer from 2,4-FDCA produced by the microorganism of any one of embodiments 1 to 43, wherein the 2,4-FDCA and a diol are catalytically polymerized in a non-biological process.

Embodiment 58. The method of embodiment 57, wherein the diol is selected from ethylene glycol, 1,3-propanediol, 1,2-propanediol, 1,4-butanediol, 1,3-butanediol, 2,3-butanediol, 1,5-pentanediol, or 1,6-hexanediol.

The invention claimed is:

1. A recombinant microorganism that is an ethanol-producing yeast comprising:
   (a) at least one exogenous nucleic acid molecule encoding a polypeptide that catalyzes the production of 4-hydroxymethylfurfural phosphate from glyceraldehyde 3-phosphate (G3P);
   (b) at least one endogenous and/or exogenous nucleic acid molecule encoding a polypeptide that catalyzes the production of 4-hydroxymethylfurfural (4-HMF) from 4-hydroxymethylfurfural phosphate;
   (c) at least one endogenous and/or exogenous nucleic acid molecule encoding one or more polypeptides that catalyze the production of 2,4-furandicarboxylic acid (2,4-FDCA) from 4-HMF through the production of the intermediates furan-2,4-dicarbaldehyde, 4-(hydroxymethyl)furoic acid, 4-formylfuran-2-carboxylate, 4-formylfuran-2-carboxylate, and/or 2-formylfuran-4-carboxylate, wherein the production of 2,4-FDCA leads to the reduction of (i) NAD to NADH or (ii) NADP to NADPH;
   (d) at least one nucleic acid molecule encoding a polypeptide that catalyzes the production of ribulose-1,5-bisphosphate from ribulose-5-phosphate; and
   (e) at least one nucleic acid molecule encoding a polypeptide that catalyzes the production of two molecules of glycerate-3-phosphate from the combination of $CO_2$ with ribulose-1,5-bisphosphate; and
   wherein the recombinant microorganism utilizes the glycerate-3-phosphate from (e) and the NADH and/or NADPH generated as a byproduct of 2,4-FDCA production at (c) to produce ethanol; and
wherein the 2,4-FDCA and ethanol are coproduced under anaerobic or microaerobic conditions.

2. The recombinant microorganism of claim 1, wherein the polypeptide that catalyzes the production of ribulose-1,5-bisphosphate from ribulose-5-phosphate is a phosphoribulokinase (PRK).

3. The recombinant microorganism of claim 1, wherein the polypeptide that catalyzes the production of glycerate-3-phosphate from the combination of $CO_2$ with ribulose-1,5-bisphosphate is a ribulose-1,5-bisphosphate carboxylase (RuBisCO), wherein the RuBisCO is selected from Form I, Form II, Form III, or a combination thereof.

4. The recombinant microorganism of claim 1, further comprising at least one genetic modification that leads to a down-regulation or a deletion of an enzyme in a glycerol-production pathway, wherein the enzyme in the glycerol-production pathway is a GPD1 and/or a GPD2, and/or a glycerol-3-phosphate phosphatase.

5. The recombinant microorganism of claim 1, further comprising at least one nucleic acid molecule encoding a chaperone protein.

6. A recombinant microorganism that is an ethanol-producing yeast comprising:
(a) at least one exogenous nucleic acid molecule encoding a polypeptide that catalyzes the production of 4-hydroxymethylfurfural phosphate from glyceraldehyde 3-phosphate (G3P);
(b) at least one endogenous and/or exogenous nucleic acid molecule encoding a polypeptide that catalyzes the production of 4-hydroxymethylfurfural (4-HMF) from 4-hydroxymethylfurfural phosphate;
(c) at least one endogenous and/or exogenous nucleic acid molecule encoding one or more polypeptides that catalyze the production of 2,4-furandicarboxylic acid (2,4-FDCA) from 4-HMF through the production of the intermediates furan-2,4-dicarbaldehyde, 4-(hydroxymethyl)furoic acid, 4-formylfuran-2-carboxylate, 4-formylfuran-2-carboxylate, and/or 2-formylfuran-4-carboxylate, wherein the production of 2,4-FDCA leads to the reduction of (i) NAD to NADH or (ii) NADP to NADPH;
(d) at least one nucleic acid molecule encoding a polypeptide that catalyzes the production of acetyl phosphate and D-glyceraldehyde-3-phosphate from D-xylulose-5-phosphate and phosphate, and/or at least one nucleic acid molecule encoding a polypeptide that catalyzes the production of acetyl phosphate and erythrose-4-phosphate from fructose-6-phosphate and phosphate;
(e) at least one nucleic acid molecule encoding one or more polypeptides that catalyze:
(1) the production of acetyl-CoA from acetyl phosphate and free coenzyme A; and/or
(2) the production of acetate from acetyl phosphate and the production of acetyl-CoA from acetate; and
(f) at least one nucleic acid molecule encoding one or more polypeptides that catalyze:
(1) the production of acetaldehyde from acetyl-CoA; and/or
(2) the production of ethanol from acetyl-CoA;
and;
wherein the recombinant microorganism utilizes the NADH and/or NADPH generated as a byproduct of 2,4-FDCA production at (c) to produce ethanol, and;
wherein the 2,4-FDCA and ethanol are coproduced under anaerobic or microaerobic conditions.

7. The recombinant microorganism of claim 6, further comprising at least one genetic modification that leads to a down-regulation or a deletion of an enzyme in a glycerol-production pathway, wherein the enzyme in the glycerol-production pathway is a GPD1 and/or a GPD2, and/or a glycerol-3-phosphate phosphatase.

8. The recombinant microorganism of claim 6, wherein the polypeptide that catalyzes the production of acetyl phosphate and D-glyceraldehyde-3-phosphate from D-xylulose-5-phosphate and phosphate is a phosphoketolase, wherein the phosphoketolase is classified as EC number 4.1.2.9.

9. The recombinant microorganism of claim 6, wherein the polypeptide that catalyzes the production of acetyl phosphate and erythrose-4-phosphate from fructose phosphate and phosphate is a phosphoketolase, wherein the phosphoketolase is classified as EC number 4.1.2.22.

10. The recombinant microorganism of claim 6, wherein the polypeptide that catalyzes the production of acetyl-CoA from acetyl phosphate and free coenzyme A is a phosphotransacetylase, wherein the phosphotransacetylase is classified as EC number 2.3.1.8.

11. The recombinant microorganism of claim 6, wherein the polypeptide that catalyzes the production of acetate from acetyl phosphate is an acetate kinase, wherein the acetate kinase is classified as EC number 2.7.2.12.

12. The recombinant microorganism of claim 6, wherein the polypeptide that catalyzes the production of acetyl-CoA from acetate is an acetyl-CoA synthetase or an acetate-CoA ligase, wherein the acetyl-CoA synthetase or acetate-CoA ligase is classified as EC number 6.2.1.1.

13. The recombinant microorganism of claim 6, wherein the polypeptide that catalyzes the production of acetaldehyde from acetyl-CoA is an acetaldehyde dehydrogenase.

14. The recombinant microorganism of claim 6, wherein the polypeptide that catalyzes the production of ethanol from acetaldehyde is an alcohol dehydrogenase.

15. The recombinant microorganism of claim 6, wherein the polypeptide that catalyzes the production of ethanol from acetyl-CoA is a bifunctional NADH- and/or NADPH-dependent acetaldehyde-alcohol dehydrogenase, wherein the enzyme is classified as both EC number 1.2.1.10 and EC number 1.1.1.1.

16. The recombinant microorganism of claim 6, further comprising at least one genetic modification that leads to an up-regulation of an enzyme in a non-oxidative pentose phosphate pathway, wherein the enzyme is a transaldolase classified as EC number 2.2.1.2, and/or wherein the enzyme is a transketolase classified as EC number 2.2.1.1, and/or wherein the enzyme is a ribose-5-phosphate isomerase classified as EC number 5.3.1.6, and/or wherein the enzyme is a ribulose-5-phosphate 3-epimerase.

17. A recombinant microorganism that is an ethanol-producing yeast comprising:
(a) at least one exogenous nucleic acid molecule encoding a polypeptide that catalyzes the production of 4-hydroxymethylfurfural phosphate from glyceraldehyde 3-phosphate (G3P);
(b) at least one endogenous and/or exogenous nucleic acid molecule encoding a polypeptide that catalyzes the production of 4-hydroxymethylfurfural (4-HMF) from 4-hydroxymethylfurfural phosphate;
(c) at least one endogenous and/or exogenous nucleic acid molecule encoding one or more polypeptides that catalyze the production of 2,4-furandicarboxylic acid (2,4-

FDCA) from 4-HMF through the production of the intermediates furan-2,4-dicarbaldehyde, 4-(hydroxymethyl)furoic acid, 4-formylfuran-2-carboxylate, 4-formylfuran-2-carboxylate, and/or 2-formylfuran-4-carboxylate, wherein the production of 2,4-FDCA leads to the reduction of (i) NAD to NADH or (ii) NADP to NADPH;

(d) a glycerol-production pathway, and;

wherein the recombinant microorganism utilizes the NADH and/or NADPH generated as a byproduct of 2,4-FDCA production to produce glycerol, and;

wherein the 2,4-FDCA and ethanol are coproduced under anaerobic or microaerobic conditions.

18. The recombinant microorganism of claim 1, wherein the microorganism is selected from *Saccharomyces* spp, *Saccharomyces cerevisiae*, *Issatchenkia* spp., *Hansenula* spp., *Debaryomyces* spp., *Rhodotula* spp.,*Pachysolen* spp., *Cryptococcus* spp., *Trichosporon* spp., *Myxozyma* spp., *Candida* spp., *Kluyveromyces* spp., *Pichia* spp., *Schizosaccharomyces* spp., *Torulaspora* spp., *Zygosaccharomyces* spp., *Yarrowia* spp., *Yarrowia Scheffersomyces* spp. or *Scheffersomyces* stipites.

19. A method of co-producing 2,4-FDCA and ethanol comprising: contacting the recombinant microorganism of claim 1 with a fermentable carbon source under conditions sufficient to produce 2,4-FDCA and ethanol.

20. The method of claim 19, wherein the recombinant microorganism produces a molar ratio of ethanol:2,4-FDCA of greater than 1:1.

21. The recombinant microorganism of claim 9, wherein the phosphoketolase is a single-specificity phosphoketolase or wherein the phosphoketolase is a dual-specificity phosphoketolase.

22. The method of claim 19, wherein the conditions comprise anaerobic or microaerobic conditions.

23. The method of claim 20, wherein the recombinant microorganism produces a molar ratio of ethanol:2,4-FDCA of greater than 4:1.

* * * * *

SEQUENCE LISTING

```
<160> NUMBER OF SEQ ID NOS: 23

<210> SEQ ID NO 1
<211> LENGTH: 402
<212> TYPE: PRT
<213> ORGANISM: Spinacia oleracea

<400> SEQUENCE: 1

Met Ala Val Cys Thr Val Tyr Thr Ile Pro Thr Thr Thr His Leu Gly
1               5                   10                  15

Ser Ser Phe Asn Gln Asn Asn Lys Gln Val Phe Phe Asn Tyr Lys Arg
            20                  25                  30

Ser Ser Ser Ser Asn Asn Thr Leu Phe Thr Thr Arg Pro Ser Tyr Val
        35                  40                  45

Ile Thr Cys Ser Gln Gln Gln Thr Ile Val Ile Gly Leu Ala Ala Asp
    50                  55                  60

Ser Gly Cys Gly Lys Ser Thr Phe Met Arg Arg Leu Thr Ser Val Phe
65                  70                  75                  80

Gly Gly Ala Ala Glu Pro Pro Lys Gly Gly Asn Pro Asp Ser Asn Thr
                85                  90                  95

Leu Ile Ser Asp Thr Thr Thr Val Ile Cys Leu Asp Asp Phe His Ser
            100                 105                 110

Leu Asp Arg Asn Gly Arg Lys Val Glu Lys Val Thr Ala Leu Asp Pro
```

```
            115                 120                 125
Lys Ala Asn Asp Phe Asp Leu Met Tyr Glu Gln Val Lys Ala Leu Lys
    130                 135                 140

Glu Gly Lys Ala Val Asp Lys Pro Ile Tyr Asn His Val Ser Gly Leu
145                 150                 155                 160

Leu Asp Pro Pro Glu Leu Ile Gln Pro Pro Lys Ile Leu Val Ile Glu
                165                 170                 175

Gly Leu His Pro Met Tyr Asp Ala Arg Val Arg Glu Leu Leu Asp Phe
            180                 185                 190

Ser Ile Tyr Leu Asp Ile Ser Asn Glu Val Lys Phe Ala Trp Lys Ile
        195                 200                 205

Gln Arg Asp Met Lys Glu Arg Gly His Ser Leu Glu Ser Ile Lys Ala
    210                 215                 220

Ser Ile Glu Ser Arg Lys Pro Asp Phe Asp Ala Tyr Ile Asp Pro Gln
225                 230                 235                 240

Lys Gln His Ala Asp Val Val Ile Glu Val Leu Pro Thr Glu Leu Ile
                245                 250                 255

Pro Asp Asp Asp Glu Gly Lys Val Leu Arg Val Arg Met Ile Gln Lys
            260                 265                 270

Glu Gly Val Lys Phe Phe Asn Pro Val Tyr Leu Phe Asp Glu Gly Ser
        275                 280                 285

Thr Ile Ser Trp Ile Pro Cys Gly Arg Lys Leu Thr Cys Ser Tyr Pro
    290                 295                 300

Gly Ile Lys Phe Ser Tyr Gly Pro Asp Thr Phe Tyr Gly Asn Glu Val
305                 310                 315                 320

Thr Val Val Glu Met Asp Gly Met Phe Asp Arg Leu Asp Glu Leu Ile
                325                 330                 335

Tyr Val Glu Ser His Leu Ser Asn Leu Ser Thr Lys Phe Tyr Gly Glu
            340                 345                 350

Val Thr Gln Gln Met Leu Lys His Gln Asn Phe Pro Gly Ser Asn Asn
        355                 360                 365

Gly Thr Gly Phe Phe Gln Thr Ile Ile Gly Leu Lys Ile Arg Asp Leu
    370                 375                 380

Phe Glu Gln Leu Val Ala Ser Arg Ser Thr Ala Thr Ala Thr Ala Ala
385                 390                 395                 400

Lys Ala

<210> SEQ ID NO 2
<211> LENGTH: 333
<212> TYPE: PRT
<213> ORGANISM: Synechococcus elongatus

<400> SEQUENCE: 2

Met Ser Lys Pro Asp Arg Val Val Leu Ile Gly Val Ala Gly Asp Ser
1               5                   10                  15

Gly Cys Gly Lys Ser Thr Phe Leu Asn Arg Leu Ala Asp Leu Phe Gly
            20                  25                  30

Thr Glu Leu Met Thr Val Ile Cys Leu Asp Asp Tyr His Ser Leu Asp
        35                  40                  45

Arg Lys Gly Arg Lys Glu Ala Gly Val Thr Ala Leu Asp Pro Arg Ala
    50                  55                  60

Asn Asn Phe Asp Leu Met Tyr Glu Gln Val Lys Ala Leu Lys Asn Gly
65                  70                  75                  80

Glu Thr Ile Met Lys Pro Ile Tyr Asn His Glu Thr Gly Leu Ile Asp
```

```
                85                  90                  95
Pro Pro Glu Lys Ile Glu Pro Asn Arg Ile Val Ile Glu Gly Leu
            100                 105                 110
His Pro Leu Tyr Asp Glu Arg Val Arg Glu Leu Leu Asp Phe Ser Val
            115                 120                 125
Tyr Leu Asp Ile Asp Asp Glu Val Lys Ile Ala Trp Lys Ile Gln Arg
130                 135                 140
Asp Met Ala Glu Arg Gly His Ser Tyr Glu Asp Val Leu Ala Ser Ile
145                 150                 155                 160
Glu Ala Arg Arg Pro Asp Phe Lys Ala Tyr Ile Glu Pro Gln Arg Gly
                165                 170                 175
His Ala Asp Ile Val Ile Arg Val Met Pro Thr Gln Leu Ile Pro Asn
                180                 185                 190
Asp Thr Glu Arg Lys Val Leu Arg Val Gln Leu Ile Gln Arg Glu Gly
                195                 200                 205
Arg Asp Gly Phe Glu Pro Ala Tyr Leu Phe Asp Glu Gly Ser Thr Ile
            210                 215                 220
Gln Trp Thr Pro Cys Gly Arg Lys Leu Thr Cys Ser Tyr Pro Gly Ile
225                 230                 235                 240
Arg Leu Ala Tyr Gly Pro Asp Thr Tyr Tyr Gly His Glu Val Ser Val
                245                 250                 255
Leu Glu Val Asp Gly Gln Phe Glu Asn Leu Glu Glu Met Ile Tyr Val
                260                 265                 270
Glu Gly His Leu Ser Lys Thr Asp Thr Gln Tyr Tyr Gly Glu Leu Thr
                275                 280                 285
His Leu Leu Gln His Lys Asp Tyr Pro Gly Ser Asn Asn Gly Thr
            290                 295                 300
Gly Leu Phe Gln Val Leu Thr Gly Leu Lys Met Arg Ala Ala Tyr Glu
305                 310                 315                 320
Arg Leu Thr Ser Gln Ala Ala Pro Val Ala Ala Ser Val
                325                 330

<210> SEQ ID NO 3
<211> LENGTH: 292
<212> TYPE: PRT
<213> ORGANISM: Cupriavidus necator

<400> SEQUENCE: 3

Met Ser Glu Arg Tyr Pro Ile Ile Ala Ile Thr Gly Ser Ser Gly Ala
1               5                   10                  15
Gly Thr Thr Ser Val Thr Arg Thr Phe Glu Asn Ile Phe Arg Arg Glu
                20                  25                  30
Gly Val Lys Ser Val Val Ile Glu Gly Asp Ser Phe His Arg Tyr Asp
            35                  40                  45
Arg Ala Glu Met Lys Val Lys Met Ala Glu Ala Glu Arg Thr Gly Asn
50                  55                  60
Met Asn Phe Ser His Phe Gly Glu Glu Asn Asn Leu Phe Gly Glu Leu
65                  70                  75                  80
Glu Asn Leu Phe Arg Ser Tyr Ala Glu Thr Gly Thr Gly Met His Arg
                85                  90                  95
His Tyr Leu His Ser Pro Glu Glu Ala Ala Pro Phe Gly Gln Glu Pro
            100                 105                 110
Gly Thr Phe Thr Gln Trp Glu Pro Leu Pro Ala Asp Thr Asp Leu Leu
            115                 120                 125
```

```
Phe Tyr Glu Gly Leu His Gly Gly Val Val Thr Asp Ser Val Asn Val
            130                 135                 140

Ala Gln Tyr Pro Asn Leu Leu Ile Gly Val Val Pro Val Ile Asn Leu
145                 150                 155                 160

Glu Trp Ile Gln Lys Leu Trp Arg Asp Lys Lys Gln Arg Gly Tyr Ser
                165                 170                 175

Thr Glu Ala Val Thr Asp Thr Ile Leu Arg Arg Met Pro Asp Tyr Val
            180                 185                 190

Asn Tyr Ile Cys Pro Gln Phe Ser Arg Thr His Val Asn Phe Gln Arg
        195                 200                 205

Val Pro Cys Val Asp Thr Ser Asn Pro Phe Ile Ser Arg Glu Ile Pro
210                 215                 220

Ala Pro Asp Glu Ser Met Val Val Ile Arg Phe Ala Asn Pro Lys Gly
225                 230                 235                 240

Ile Asp Phe Gln Tyr Leu Leu Ser Met Ile His Asp Ser Phe Met Ser
                245                 250                 255

Arg Ala Asn Thr Ile Val Val Pro Gly Gly Lys Met Glu Leu Ala Met
            260                 265                 270

Gln Leu Ile Phe Thr Pro Phe Val Leu Arg Met Met Glu Arg Arg Lys
        275                 280                 285

Arg Ala Ala Gln
    290

<210> SEQ ID NO 4
<211> LENGTH: 290
<212> TYPE: PRT
<213> ORGANISM: Nitrobacter vulgaris

<400> SEQUENCE: 4

Met Leu Arg Lys His Pro Ile Ile Ser Ile Thr Gly Ser Ser Gly Ala
1               5                   10                  15

Gly Thr Thr Ser Val Lys Arg Thr Phe Glu Gln Ile Phe Arg Arg Glu
            20                  25                  30

Asn Val Val Ala Ala Tyr Ile Glu Gly Asp Ala Phe His Arg Tyr Asn
        35                  40                  45

Arg Ala Glu Met Arg Thr Arg Met Ala Glu Glu Ser Asp Lys Gly Asn
50                  55                  60

Lys His Phe Ser His Phe Ser Pro Glu Thr Asn Leu Phe Ala Glu Leu
65                  70                  75                  80

Glu Gly Val Phe Arg Ser Tyr Gly Glu Thr Gly Thr Gly Asn Thr Arg
                85                  90                  95

Tyr Tyr Val His Asp Asp Ala Glu Ser Ala Leu His Gly Val Pro Pro
            100                 105                 110

Gly Thr Phe Thr Asp Trp Gln Pro Leu Pro Asp Ala Ser Asp Leu Leu
        115                 120                 125

Phe Tyr Glu Gly Leu His Gly Ala Val Val Thr Asp Lys Val Asn Val
            130                 135                 140

Ala Gln Tyr Ala Asp Leu Lys Ile Gly Val Val Pro Val Ile Asn Leu
145                 150                 155                 160

Glu Trp Ile Gln Lys Leu His Arg Asp Arg Asn Ala Arg Gly Tyr Ser
                165                 170                 175

Thr Glu Ala Val Thr Asp Thr Ile Leu Arg Arg Met Pro Asp Tyr Val
            180                 185                 190

Asn Tyr Ile Cys Pro Gln Phe Ala Glu Thr Asp Ile Asn Phe Gln Arg
        195                 200                 205
```

```
Val Pro Thr Val Asp Thr Ser Asn Pro Phe Ile Ser Arg Trp Ile Pro
    210                 215                 220

Thr Pro Asp Glu Ser Met Val Val Ile Arg Leu Lys Asn Pro Arg Gly
225                 230                 235                 240

Ile Asp Phe Pro Tyr Leu Leu Ser Met Ile Pro Ser Ser Phe Met Ser
                245                 250                 255

Arg Ala Asn Ser Ile Val Ile His Gly Ser Lys Leu Asp Leu Ala Met
            260                 265                 270

Gln Leu Ile Leu Thr Pro Leu Ile Leu Gln Leu Ile Glu Arg Lys Lys
        275                 280                 285

Arg Ala
    290

<210> SEQ ID NO 5
<211> LENGTH: 472
<212> TYPE: PRT
<213> ORGANISM: Synechococcus sp

<400> SEQUENCE: 5

Met Pro Lys Thr Gln Ser Ala Ala Gly Tyr Lys Ala Gly Val Lys Asp
1               5                   10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
```

```
                275                 280                 285
        His Ile His Arg Ala Met His Ala Val Ile Asp Arg Gln Arg Asn His
            290                 295                 300

Gly Ile His Phe Arg Val Leu Ala Lys Cys Leu Arg Leu Ser Gly Gly
        305                 310                 315                 320

Asp His Leu His Ser Gly Thr Val Val Gly Lys Leu Glu Gly Asp Lys
                        325                 330                 335

Ala Ser Thr Leu Gly Phe Val Asp Leu Met Arg Glu Asp His Ile Glu
                    340                 345                 350

Ala Asp Arg Ser Arg Gly Val Phe Phe Thr Gln Asp Trp Ala Ser Met
                355                 360                 365

Pro Gly Val Leu Pro Val Ala Ser Gly Gly Ile His Val Trp His Met
        370                 375                 380

Pro Ala Leu Val Glu Ile Phe Gly Asp Asp Ser Val Leu Gln Phe Gly
        385                 390                 395                 400

Gly Gly Thr Leu Gly His Pro Trp Gly Asn Ala Pro Gly Ala Thr Ala
                        405                 410                 415

Asn Arg Val Ala Leu Glu Ala Cys Val Gln Ala Arg Asn Glu Gly Arg
                    420                 425                 430

Asp Leu Tyr Arg Glu Gly Gly Asp Ile Leu Arg Glu Ala Gly Lys Trp
                435                 440                 445

Ser Pro Glu Leu Ala Ala Ala Leu Asp Leu Trp Lys Glu Ile Lys Phe
            450                 455                 460

Glu Phe Glu Thr Met Asp Lys Leu
        465                 470

<210> SEQ ID NO 6
<211> LENGTH: 111
<212> TYPE: PRT
<213> ORGANISM: Synechococcus sp

<400> SEQUENCE: 6

Met Ser Met Lys Thr Leu Pro Lys Glu Arg Arg Phe Glu Thr Phe Ser
1               5                   10                  15

Tyr Leu Pro Pro Leu Ser Asp Arg Gln Ile Ala Ala Gln Ile Glu Tyr
                20                  25                  30

Met Ile Glu Gln Gly Phe His Pro Leu Ile Glu Phe Asn Glu His Ser
            35                  40                  45

Asn Pro Glu Glu Phe Tyr Trp Thr Met Trp Lys Leu Pro Leu Phe Asp
    50                  55                  60

Cys Lys Ser Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
                85                  90                  95

Gln Cys Gln Thr Val Ser Phe Ile Val His Arg Pro Gly Arg Tyr
            100                 105                 110

<210> SEQ ID NO 7
<211> LENGTH: 485
<212> TYPE: PRT
<213> ORGANISM: Cupriavidus necator

<400> SEQUENCE: 7

Met Asn Ala Pro Glu Ser Val Gln Ala Lys Pro Arg Lys Arg Tyr Asp
1               5                   10                  15

Ala Gly Val Met Lys Tyr Lys Glu Met Gly Tyr Trp Asp Gly Asp Tyr
```

```
                    20                  25                  30
Glu Pro Lys Asp Thr Asp Leu Leu Ala Leu Phe Arg Ile Thr Pro Gln
                35                  40                  45

Asp Gly Val Asp Pro Val Glu Ala Ala Ala Val Ala Gly Glu Ser
            50                  55                  60

Ser Thr Ala Thr Trp Thr Val Val Trp Thr Asp Arg Leu Thr Ala Cys
65                  70                  75                  80

Asp Met Ser Val Gln Gly Leu Arg Val Asp Pro Val Pro Asn Asn Pro
                85                  90                  95

Glu Gln Phe Phe Cys Tyr Val Ala Tyr Asp Leu Ser Leu Phe Glu Glu
                100                 105                 110

Gly Ser Ile Ala Asn Leu Thr Ala Ser Ile Ile Gly Asn Val Phe Ser
                115                 120                 125

Phe Lys Pro Ile Lys Ala Ala Arg Leu Glu Asp Met Arg Phe Pro Val
                130                 135                 140

Ala Tyr Val Lys Thr Phe Ala Gly Pro Ser Thr Gly Ile Ile Val Glu
145                 150                 155                 160

Arg Glu Arg Leu Asp Lys Phe Gly Arg Pro Leu Leu Gly Ala Thr Thr
                165                 170                 175

Lys Pro Lys Leu Gly Leu Ser Gly Arg Asn Tyr Gly Arg Val Val Tyr
                180                 185                 190

Glu Gly Leu Lys Gly Gly Leu Asp Phe Met Lys Asp Asp Glu Asn Ile
                195                 200                 205

Asn Ser Gln Pro Phe Met His Trp Arg Asp Arg Phe Leu Phe Val Met
                210                 215                 220

Asp Ala Val Asn Lys Ala Ser Ala Ala Thr Gly Glu Val Lys Gly Ser
225                 230                 235                 240

Tyr Leu Asn Val Thr Ala Gly Thr Met Glu Glu Met Tyr Arg Arg Ala
                245                 250                 255

Glu Phe Ala Lys Ser Leu Gly Ser Val Ile Ile Met Ile Asp Leu Ile
                260                 265                 270

Val Gly Trp Thr Cys Ile Gln Ser Met Ser Asn Trp Cys Arg Gln Asn
                275                 280                 285

Asp Met Ile Leu His Leu His Arg Ala Gly His Gly Thr Tyr Thr Arg
                290                 295                 300

Gln Lys Asn His Gly Val Ser Phe Arg Val Ile Ala Lys Trp Leu Arg
305                 310                 315                 320

Leu Ala Gly Val Asp His Met His Thr Gly Thr Ala Val Gly Lys Leu
                325                 330                 335

Glu Gly Asp Pro Leu Thr Val Gln Gly Tyr Tyr Asn Val Cys Arg Asp
                340                 345                 350

Ala Tyr Thr His Ala Asp Leu Ser Arg Gly Leu Phe Phe Asp Gln Asp
                355                 360                 365

Trp Ala Ser Leu Arg Lys Val Met Pro Val Ala Ser Gly Gly Ile His
                370                 375                 380

Ala Gly Gln Met His Gln Leu Ile Ser Leu Phe Gly Asp Asp Val Val
385                 390                 395                 400

Leu Gln Phe Gly Gly Gly Thr Ile Gly His Pro Gln Gly Ile Gln Ala
                405                 410                 415

Gly Ala Thr Ala Asn Arg Val Ala Leu Glu Ala Met Val Leu Ala Arg
                420                 425                 430

Asn Glu Gly Arg Asp Ile Leu Asn Glu Gly Pro Glu Ile Leu Arg Asp
                435                 440                 445
```

```
Ala Ala Arg Trp Cys Gly Pro Leu Arg Ala Ala Leu Asp Thr Trp Gly
    450                 455                 460

Asp Ile Ser Phe Asn Tyr Thr Pro Thr Asp Thr Ser Asp Phe Ala Pro
465                 470                 475                 480

Thr Ala Ser Val Ala
                485

<210> SEQ ID NO 8
<211> LENGTH: 486
<212> TYPE: PRT
<213> ORGANISM: Cupriavidus necator

<400> SEQUENCE: 8

Met Asn Ala Pro Glu Ser Val Gln Ala Lys Pro Arg Lys Arg Tyr Asp
1               5                   10                  15

Ala Gly Val Met Lys Tyr Lys Glu Met Gly Tyr Trp Asp Gly Asp Tyr
                20                  25                  30

Glu Pro Lys Asp Thr Asp Leu Leu Ala Leu Phe Arg Ile Thr Pro Gln
            35                  40                  45

Asp Gly Val Asp Pro Val Glu Ala Ala Ala Val Ala Gly Glu Ser
    50                  55                  60

Ser Thr Ala Thr Trp Thr Val Trp Thr Asp Arg Leu Thr Ala Cys
65              70                  75                  80

Asp Met Tyr Arg Ala Lys Ala Tyr Arg Val Asp Pro Val Pro Asn Asn
                85                  90                  95

Pro Glu Gln Phe Phe Cys Tyr Val Ala Tyr Asp Leu Ser Leu Phe Glu
            100                 105                 110

Glu Gly Ser Ile Ala Asn Leu Thr Ala Ser Ile Ile Gly Asn Val Phe
        115                 120                 125

Ser Phe Lys Pro Ile Lys Ala Ala Arg Leu Glu Asp Met Arg Phe Pro
130                 135                 140

Val Ala Tyr Val Lys Thr Phe Ala Gly Pro Ser Thr Gly Ile Ile Val
145                 150                 155                 160

Glu Arg Glu Arg Leu Asp Lys Phe Gly Arg Pro Leu Leu Gly Ala Thr
                165                 170                 175

Thr Lys Pro Lys Leu Gly Leu Ser Gly Arg Asn Tyr Gly Arg Val Val
            180                 185                 190

Tyr Glu Gly Leu Lys Gly Gly Leu Asp Phe Met Lys Asp Asp Glu Asn
        195                 200                 205

Ile Asn Ser Gln Pro Phe Met His Trp Arg Asp Arg Phe Leu Phe Val
    210                 215                 220

Met Asp Ala Val Asn Lys Ala Ser Ala Ala Thr Gly Glu Val Lys Gly
225                 230                 235                 240

Ser Tyr Leu Asn Val Thr Ala Gly Thr Met Glu Glu Met Tyr Arg Arg
                245                 250                 255

Ala Glu Phe Ala Lys Ser Leu Gly Ser Val Ile Ile Met Ile Asp Leu
            260                 265                 270

Ile Val Gly Trp Thr Cys Ile Gln Ser Met Ser Asn Trp Cys Arg Gln
        275                 280                 285

Asn Asp Met Ile Leu His His Arg Ala Gly His Gly Thr Tyr Thr
    290                 295                 300

Arg Gln Lys Asn His Gly Val Ser Phe Arg Val Ile Ala Lys Trp Leu
305                 310                 315                 320

Arg Leu Ala Gly Val Asp His Met His Thr Gly Thr Ala Val Gly Lys
```

```
                        325                 330                 335
Leu Glu Gly Asp Pro Leu Thr Val Gln Gly Tyr Tyr Asn Val Cys Arg
            340                 345                 350

Asp Ala Tyr Thr His Ala Asp Leu Ser Arg Gly Leu Phe Phe Asp Gln
        355                 360                 365

Asp Trp Ala Ser Leu Arg Lys Val Met Pro Val Ala Ser Gly Gly Ile
    370                 375                 380

His Ala Gly Gln Met His Gln Leu Ile Ser Leu Phe Gly Asp Asp Val
385                 390                 395                 400

Val Leu Gln Phe Gly Gly Thr Ile Gly His Pro Gln Gly Ile Gln
                405                 410                 415

Ala Gly Ala Thr Ala Asn Arg Val Ala Leu Glu Ala Met Val Leu Ala
            420                 425                 430

Arg Asn Glu Gly Arg Asp Ile Leu Asn Glu Gly Pro Glu Ile Leu Arg
        435                 440                 445

Asp Ala Ala Arg Trp Cys Gly Pro Leu Arg Ala Ala Leu Asp Thr Trp
    450                 455                 460

Gly Asp Ile Ser Phe Asn Tyr Thr Pro Thr Asp Thr Ser Asp Phe Ala
465                 470                 475                 480

Pro Thr Ala Ser Val Ala
                485

<210> SEQ ID NO 9
<211> LENGTH: 139
<212> TYPE: PRT
<213> ORGANISM: Cupriavidus necator

<400> SEQUENCE: 9

Met Arg Ile Thr Gln Gly Thr Phe Ser Phe Leu Pro Glu Leu Thr Asp
1               5                   10                  15

Glu Gln Ile Thr Lys Gln Leu Glu Tyr Cys Leu Asn Gln Gly Trp Ala
            20                  25                  30

Val Gly Leu Glu Tyr Thr Asp Asp Pro His Pro Arg Asn Thr Tyr Trp
        35                  40                  45

Glu Met Phe Gly Leu Pro Met Phe Asp Leu Arg Asp Ala Ala Gly Ile
    50                  55                  60

Leu Met Glu Ile Asn Asn Ala Arg Asn Thr Phe Pro Asn His Tyr Ile
65                  70                  75                  80

Arg Val Thr Ala Phe Asp Ser Thr His Thr Val Glu Ser Val Val Met
                85                  90                  95

Ser Phe Ile Val Asn Arg Pro Ala Asp Glu Pro Gly Phe Arg Leu Val
            100                 105                 110

Arg Gln Glu Glu Pro Gly Arg Thr Leu Arg Tyr Ser Ile Glu Ser Tyr
        115                 120                 125

Ala Val Gln Ala Arg Pro Glu Gly Ser Arg Tyr
    130                 135

<210> SEQ ID NO 10
<211> LENGTH: 459
<212> TYPE: PRT
<213> ORGANISM: Thiobacillus denitrificans

<400> SEQUENCE: 10

Met Asp Gln Ser Ala Arg Tyr Ala Asp Leu Ser Leu Lys Glu Glu Asp
1               5                   10                  15

Leu Ile Lys Gly Gly Arg His Ile Leu Val Ala Tyr Lys Met Lys Pro
```

```
            20                  25                  30
Lys Ser Gly Tyr Gly Tyr Leu Glu Ala Ala His Phe Ala Ala Glu
            35                  40                  45
Ser Ser Thr Gly Thr Asn Val Glu Val Ser Thr Thr Asp Asp Phe Thr
        50                  55                  60
Lys Gly Val Asp Ala Leu Val Tyr Tyr Ile Asp Glu Ala Ser Glu Asp
65                  70                  75                  80
Met Arg Ile Ala Tyr Pro Leu Glu Leu Phe Asp Arg Asn Val Thr Asp
                85                  90                  95
Gly Arg Phe Met Leu Val Ser Phe Leu Thr Leu Ala Ile Gly Asn Asn
            100                 105                 110
Gln Gly Met Gly Asp Ile Glu His Ala Lys Met Ile Asp Phe Tyr Val
            115                 120                 125
Pro Glu Arg Cys Ile Gln Met Phe Asp Gly Pro Ala Thr Asp Ile Ser
            130                 135                 140
Asn Leu Trp Arg Ile Leu Gly Arg Pro Val Val Asn Gly Gly Tyr Ile
145                 150                 155                 160
Ala Gly Thr Ile Ile Lys Pro Lys Leu Gly Leu Arg Pro Glu Pro Phe
                165                 170                 175
Ala Lys Ala Ala Tyr Gln Phe Trp Leu Gly Gly Asp Phe Ile Lys Asn
            180                 185                 190
Asp Glu Pro Gln Gly Asn Gln Val Phe Cys Pro Leu Lys Lys Val Leu
            195                 200                 205
Pro Leu Val Tyr Asp Ala Met Lys Arg Ala Gln Asp Asp Thr Gly Gln
            210                 215                 220
Ala Lys Leu Phe Ser Met Asn Ile Thr Ala Asp Asp His Tyr Glu Met
225                 230                 235                 240
Cys Ala Arg Ala Asp Tyr Ala Leu Glu Val Phe Gly Pro Asp Ala Asp
                245                 250                 255
Lys Leu Ala Phe Leu Val Asp Gly Tyr Val Gly Gly Pro Gly Met Val
            260                 265                 270
Thr Thr Ala Arg Arg Gln Tyr Pro Gly Gln Tyr Leu His Tyr His Arg
            275                 280                 285
Ala Gly His Gly Ala Val Thr Ser Pro Ser Ala Lys Arg Gly Tyr Thr
            290                 295                 300
Ala Phe Val Leu Ala Lys Met Ser Arg Leu Gln Gly Ala Ser Gly Ile
305                 310                 315                 320
His Val Gly Thr Met Gly Tyr Gly Lys Met Glu Gly Glu Gly Asp Asp
                325                 330                 335
Lys Ile Ile Ala Tyr Met Ile Glu Arg Asp Glu Cys Gln Gly Pro Val
            340                 345                 350
Tyr Phe Gln Lys Trp Tyr Gly Met Lys Pro Thr Thr Pro Ile Ile Ser
            355                 360                 365
Gly Gly Met Asn Ala Leu Arg Leu Pro Gly Phe Phe Glu Asn Leu Gly
            370                 375                 380
His Gly Asn Val Ile Asn Thr Ala Gly Gly Gly Ser Tyr Gly His Ile
385                 390                 395                 400
Asp Ser Pro Ala Ala Gly Ala Ile Ser Leu Arg Gln Ser Tyr Glu Cys
                405                 410                 415
Trp Lys Gln Gly Ala Asp Pro Ile Glu Phe Ala Lys Glu His Lys Glu
            420                 425                 430
Phe Ala Arg Ala Phe Glu Ser Phe Pro Lys Asp Ala Asp Lys Leu Phe
            435                 440                 445
```

```
Pro Gly Trp Arg Glu Lys Leu Gly Val His Lys
    450                 455

<210> SEQ ID NO 11
<211> LENGTH: 466
<212> TYPE: PRT
<213> ORGANISM: Rhodospirillum rubrum

<400> SEQUENCE: 11

Met Asp Gln Ser Ser Arg Tyr Val Asn Leu Ala Leu Lys Glu Glu Asp
1               5                   10                  15

Leu Ile Ala Gly Gly Glu His Val Leu Cys Ala Tyr Ile Met Lys Pro
            20                  25                  30

Lys Ala Gly Tyr Gly Tyr Val Ala Thr Ala Ala His Phe Ala Ala Glu
        35                  40                  45

Ser Ser Thr Gly Thr Asn Val Glu Val Cys Thr Thr Asp Asp Phe Thr
    50                  55                  60

Arg Gly Val Asp Ala Leu Val Tyr Glu Val Asp Glu Ala Arg Glu Leu
65                  70                  75                  80

Thr Lys Ile Ala Tyr Pro Val Ala Leu Phe His Arg Asn Ile Thr Asp
                85                  90                  95

Gly Lys Ala Met Ile Ala Ser Phe Leu Thr Leu Thr Met Gly Asn Asn
            100                 105                 110

Gln Gly Met Gly Asp Val Glu Tyr Ala Lys Met His Asp Phe Tyr Val
        115                 120                 125

Pro Glu Ala Tyr Arg Ala Leu Phe Asp Gly Pro Ser Val Asn Ile Ser
    130                 135                 140

Ala Leu Trp Lys Val Leu Gly Arg Pro Glu Val Asp Gly Gly Leu Val
145                 150                 155                 160

Val Gly Thr Ile Ile Lys Pro Lys Leu Gly Leu Arg Pro Lys Pro Phe
                165                 170                 175

Ala Glu Ala Cys His Ala Phe Trp Leu Gly Gly Asp Phe Ile Lys Asn
            180                 185                 190

Asp Glu Pro Gln Gly Asn Gln Pro Phe Ala Pro Leu Arg Asp Thr Ile
        195                 200                 205

Ala Leu Val Ala Asp Ala Met Arg Arg Ala Gln Asp Glu Thr Gly Glu
    210                 215                 220

Ala Lys Leu Phe Ser Ala Asn Ile Thr Ala Asp Asp Pro Phe Glu Ile
225                 230                 235                 240

Ile Ala Arg Gly Glu Tyr Val Leu Glu Thr Phe Gly Glu Asn Ala Ser
                245                 250                 255

His Val Ala Leu Leu Val Asp Gly Tyr Val Ala Gly Ala Ala Ala Ile
            260                 265                 270

Thr Thr Ala Arg Arg Arg Phe Pro Asp Asn Phe Leu His Tyr His Arg
        275                 280                 285

Ala Gly His Gly Ala Val Thr Ser Pro Gln Ser Lys Arg Gly Tyr Thr
    290                 295                 300

Ala Phe Val His Cys Lys Met Ala Arg Leu Gln Gly Ala Ser Gly Ile
305                 310                 315                 320

His Thr Gly Thr Met Gly Phe Gly Lys Met Glu Gly Glu Ser Ser Asp
                325                 330                 335

Arg Ala Ile Ala Tyr Met Leu Thr Gln Asp Glu Ala Gln Gly Pro Phe
            340                 345                 350

Tyr Arg Gln Ser Trp Gly Gly Met Lys Ala Cys Thr Pro Ile Ile Ser
```

```
                     355                 360                 365
Gly Gly Met Asn Ala Leu Arg Met Pro Gly Phe Phe Glu Asn Leu Gly
    370                 375                 380

Asn Ala Asn Val Ile Leu Thr Ala Gly Gly Ala Phe Gly His Ile
385                 390                 395                 400

Asp Gly Pro Val Ala Gly Ala Arg Ser Leu Arg Gln Ala Trp Gln Ala
                405                 410                 415

Trp Arg Asp Gly Val Pro Val Leu Asp Tyr Ala Arg Glu His Lys Glu
            420                 425                 430

Leu Ala Arg Ala Phe Glu Ser Phe Pro Gly Asp Ala Asp Gln Ile Tyr
        435                 440                 445

Pro Gly Trp Arg Lys Ala Leu Gly Val Glu Asp Thr Arg Ser Ala Leu
    450                 455                 460

Pro Ala
465

<210> SEQ ID NO 12
<211> LENGTH: 459
<212> TYPE: PRT
<213> ORGANISM: Rhodoferax ferriducens

<400> SEQUENCE: 12

Met Asp Gln Ser Lys Arg Tyr Ala Asp Leu Ser Leu Gln Glu Ala Ala
1               5                   10                  15

Leu Ile Ala Gly Gly Gln His Ile Leu Cys Ala Tyr Lys Met Ala Pro
            20                  25                  30

Lys Asp Gly Leu Asn Tyr Leu Glu Ala Ala His Phe Ala Ala Glu
        35                  40                  45

Ser Ser Thr Gly Thr Asn Val Glu Val Cys Thr Thr Asp Asp Phe Thr
    50                  55                  60

Arg Asp Val Asp Ala Leu Val Tyr Tyr Val Asn Glu Ala Thr Glu Asp
65                  70                  75                  80

Met Arg Ile Ala Tyr Pro Leu Ala Leu Phe Asp Arg Asn Ile Thr Asp
                85                  90                  95

Gly Arg Phe Met Leu Val Ser Phe Leu Thr Leu Ala Val Gly Asn Asn
            100                 105                 110

Gln Gly Met Gly Asp Ile Lys His Ala Lys Met Ile Asp Phe Tyr Val
        115                 120                 125

Pro Glu Arg Val Ile Gln Met Phe Asp Gly Pro Ala Lys Asp Ile Ser
    130                 135                 140

Asp Leu Trp Arg Ile Leu Gly Arg Pro Val Lys Asp Gly Gly Phe Ile
145                 150                 155                 160

Val Gly Thr Ile Ile Lys Pro Lys Leu Gly Leu Arg Pro Glu Pro Phe
                165                 170                 175

Ala Gln Ala Ala Tyr Gln Phe Trp Leu Gly Gly Asp Phe Ile Lys Asn
            180                 185                 190

Asp Glu Pro Gln Gly Asn Gln Val Phe Ser Pro Ile Lys Lys Thr Leu
        195                 200                 205

Pro Leu Val Tyr Asp Ala Leu Lys Arg Ala Gln Asp Glu Thr Gly Gln
    210                 215                 220

Ala Lys Leu Phe Ser Met Asn Ile Thr Ala Asp Asp His Phe Glu Met
225                 230                 235                 240

Cys Ala Arg Ala Asp Phe Ala Leu Glu Thr Phe Gly Ala Asp Ala Asp
                245                 250                 255
```

```
Lys Leu Ala Phe Leu Val Asp Gly Phe Val Gly Pro Gly Met Val
            260                 265                 270

Thr Thr Ala Arg Arg Gln Tyr Pro Asn Gln Tyr Leu His Tyr His Arg
        275                 280                 285

Gly Gly His Gly Met Val Thr Ser Pro Ser Ser Lys Arg Gly Tyr Thr
    290                 295                 300

Ala Leu Val Leu Ala Lys Met Ser Arg Leu Gln Gly Ala Ser Gly Ile
305                 310                 315                 320

His Val Gly Thr Met Gly His Gly Lys Met Glu Gly Ala Gly Asp Asp
                325                 330                 335

Arg Val Met Ala Tyr Met Ile Glu Arg Asp Glu Cys Gln Gly Pro Val
            340                 345                 350

Tyr Phe Gln Lys Trp Tyr Gly Ile Lys Pro Thr Thr Pro Ile Val Ser
        355                 360                 365

Gly Gly Met Asn Ala Leu Arg Leu Pro Gly Phe Phe Asp Asn Leu Gly
    370                 375                 380

His Gly Asn Ile Ile Asn Thr Ala Gly Gly Ser Tyr Gly His Leu
385                 390                 395                 400

Asp Ser Pro Ala Ala Gly Ala Val Ser Leu Arg Gln Ala Tyr Glu Cys
            405                 410                 415

Trp Lys Ala Gly Ala Asp Pro Ile Glu Trp Ala Lys Glu His Arg Glu
        420                 425                 430

Phe Ala Arg Ala Phe Glu Ser Phe Pro Gln Asp Ala Asp Arg Leu Phe
    435                 440                 445

Ala Gly Trp Arg Asp Lys Leu Gly Val Gly Ala
450                 455

<210> SEQ ID NO 13
<211> LENGTH: 459
<212> TYPE: PRT
<213> ORGANISM: Dechloromonas aromatica

<400> SEQUENCE: 13

Met Asp Gln Ser Asn Arg Tyr Ala Asp Leu Ser Leu Thr Glu Ala Glu
1               5                   10                  15

Leu Ile Ala Gly Gly Gln His Ile Leu Cys Ala Tyr Lys Met Lys Pro
            20                  25                  30

Lys Ala Gly His Arg Tyr Leu Glu Ala Ala His Phe Ala Ala Glu
        35                  40                  45

Ser Ser Thr Gly Thr Asn Val Glu Val Cys Thr Thr Asp Glu Phe Thr
    50                  55                  60

Lys Gly Val Asp Ala Leu Val Tyr His Ile Asp Glu Ala Ser Glu Asp
65                  70                  75                  80

Met Arg Ile Ala Tyr Pro Leu Asp Leu Phe Asp Arg Asn Met Thr Asp
            85                  90                  95

Gly Arg Met Met Met Ala Ser Phe Leu Thr Leu Thr Ile Gly Asn Asn
        100                 105                 110

Gln Gly Met Gly Asp Ile Glu His Ala Lys Met Val Asp Phe Tyr Val
    115                 120                 125

Pro Arg Arg Gly Ile Glu Leu Phe Asp Gly Pro Ser Lys Asp Ile Ser
130                 135                 140

Asp Leu Trp Arg Met Leu Gly Arg Pro Val Lys Asp Gly Gly Tyr Ile
145                 150                 155                 160

Ala Gly Thr Ile Ile Lys Pro Lys Leu Gly Leu Arg Pro Glu Pro Phe
            165                 170                 175
```

Ala Arg Ala Ala Tyr Glu Phe Trp Leu Gly Gly Asp Phe Ile Lys Asn
            180                 185                 190

Asp Glu Pro Gln Gly Asn Gln Val Phe Ala Pro Leu Lys Lys Val Ile
        195                 200                 205

Pro Leu Val Tyr Asp Ser Met Lys Arg Ala Met Asp Glu Thr Gly Glu
    210                 215                 220

Ala Lys Leu Phe Ser Met Asn Ile Thr Ala Asp Asp His Phe Glu Met
225                 230                 235                 240

Cys Ala Arg Ala Asp Phe Ala Leu Glu Ala Phe Gly Pro Asp Ala Asp
                245                 250                 255

Lys Leu Ala Phe Leu Val Asp Gly Tyr Val Gly Gly Pro Gly Met Ile
                260                 265                 270

Thr Thr Ala Arg Arg Gln Tyr Pro Asn Gln Tyr Leu His Tyr His Arg
            275                 280                 285

Ala Gly His Gly Ala Val Thr Ser Pro Ser Ser Lys Arg Gly Tyr Thr
        290                 295                 300

Ala Tyr Val Leu Ala Lys Met Ser Arg Leu Gln Gly Ala Ser Gly Ile
305                 310                 315                 320

His Val Gly Thr Met Gly Tyr Gly Lys Met Glu Gly Asp Lys Asp Asp
                325                 330                 335

Arg Ala Cys Ala Tyr Ile Ile Glu Arg Asp Ser Tyr Thr Gly Pro Val
                340                 345                 350

Tyr His Gln Glu Trp Tyr Gly Met Lys Pro Thr Thr Pro Ile Ile Ser
            355                 360                 365

Gly Gly Met Asn Ala Leu Arg Leu Pro Gly Phe Phe Glu Asn Leu Gly
        370                 375                 380

His Gly Asn Val Ile Asn Thr Ala Gly Gly Ala Tyr Gly His Ile
385                 390                 395                 400

Asp Ser Pro Ala Ala Gly Ala Arg Ser Leu Arg Gln Ala Tyr Asp Cys
                405                 410                 415

Trp Lys Ala Gly Ala Asp Pro Val Glu Trp Ala Arg Asp His Tyr Glu
            420                 425                 430

Phe Ala Arg Ala Phe Glu Ser Phe Pro Gln Asp Ala Asp Gln Leu Tyr
        435                 440                 445

Pro Gly Trp Arg His Lys Leu Arg Pro Ala Ala
    450                 455

<210> SEQ ID NO 14
<211> LENGTH: 444
<212> TYPE: PRT
<213> ORGANISM: Thermococcus kodakarensis

<400> SEQUENCE: 14

Met Val Glu Lys Phe Asp Thr Ile Tyr Asp Tyr Val Asp Lys Gly
1               5                   10                  15

Tyr Glu Pro Ser Lys Lys Arg Asp Ile Ile Ala Val Phe Arg Val Thr
            20                  25                  30

Pro Ala Glu Gly Tyr Thr Ile Glu Gln Ala Ala Gly Ala Val Ala Ala
        35                  40                  45

Glu Ser Ser Thr Gly Thr Trp Thr Thr Leu Tyr Pro Trp Tyr Glu Gln
    50                  55                  60

Glu Arg Trp Ala Asp Leu Ser Ala Lys Ala Tyr Asp Phe His Asp Met
65                  70                  75                  80

Gly Asp Gly Ser Trp Ile Val Arg Ile Ala Tyr Pro Phe His Ala Phe

```
            85                  90                  95
Glu Glu Ala Asn Leu Pro Gly Leu Leu Ala Ser Ile Ala Gly Asn Ile
            100                 105                 110

Phe Gly Met Lys Arg Val Lys Gly Leu Arg Leu Glu Asp Leu Tyr Phe
            115                 120                 125

Pro Glu Lys Leu Ile Arg Glu Phe Asp Gly Pro Ala Phe Gly Ile Glu
            130                 135                 140

Gly Val Arg Lys Met Leu Glu Ile Lys Asp Arg Pro Ile Tyr Gly Val
145                 150                 155                 160

Val Pro Lys Pro Lys Val Gly Tyr Ser Pro Glu Glu Phe Glu Lys Leu
                    165                 170                 175

Ala Tyr Asp Leu Leu Ser Asn Gly Ala Asp Tyr Met Lys Asp Asp Glu
            180                 185                 190

Asn Leu Thr Ser Pro Trp Tyr Asn Arg Phe Glu Glu Arg Ala Glu Ile
            195                 200                 205

Met Ala Lys Ile Ile Asp Lys Val Glu Asn Glu Thr Gly Glu Lys Lys
            210                 215                 220

Thr Trp Phe Ala Asn Ile Thr Ala Asp Leu Leu Glu Met Glu Gln Arg
225                 230                 235                 240

Leu Glu Val Leu Ala Asp Leu Gly Leu Lys His Ala Met Val Asp Val
                    245                 250                 255

Val Ile Thr Gly Trp Gly Ala Leu Arg Tyr Ile Arg Asp Leu Ala Ala
            260                 265                 270

Asp Tyr Gly Leu Ala Ile His Gly His Arg Ala Met His Ala Ala Phe
            275                 280                 285

Thr Arg Asn Pro Tyr His Gly Ile Ser Met Phe Val Leu Ala Lys Leu
            290                 295                 300

Tyr Arg Leu Ile Gly Ile Asp Gln Leu His Val Gly Thr Ala Gly Ala
305                 310                 315                 320

Gly Lys Leu Glu Gly Gly Lys Trp Asp Val Ile Gln Asn Ala Arg Ile
                    325                 330                 335

Leu Arg Glu Ser His Tyr Lys Pro Asp Glu Asn Asp Val Phe His Leu
            340                 345                 350

Glu Gln Lys Phe Tyr Ser Ile Lys Ala Ala Phe Pro Thr Ser Ser Gly
            355                 360                 365

Gly Leu His Pro Gly Asn Ile Gln Pro Val Ile Glu Ala Leu Gly Thr
            370                 375                 380

Asp Ile Val Leu Gln Leu Gly Gly Gly Thr Leu Gly His Pro Asp Gly
385                 390                 395                 400

Pro Ala Ala Gly Ala Arg Ala Val Arg Gln Ala Ile Asp Ala Ile Met
                    405                 410                 415

Gln Gly Ile Pro Leu Asp Glu Tyr Ala Lys Thr His Lys Glu Leu Ala
            420                 425                 430

Arg Ala Leu Glu Lys Trp Gly His Val Thr Pro Val
            435                 440

<210> SEQ ID NO 15
<211> LENGTH: 414
<212> TYPE: PRT
<213> ORGANISM: Haloferax sp.

<400> SEQUENCE: 15

Met Gly Ile Thr Tyr Glu Asp Phe Leu Asp Leu Asp Tyr Glu Pro Thr
1               5                   10                  15
```

Asp Glu Asp Leu Val Cys Thr Phe Arg Ile Asp Pro Ala Thr Gly Met
            20                  25                  30

Ser Thr Glu Ala Ala Ala Ser Arg Val Ala Ser Glu Ser Ser Asn Gly
        35                  40                  45

Thr Trp Ala Ala Leu Gln Thr Gly Ala Asp Phe Thr Asp Met Gly Ala
    50                  55                  60

Thr Thr Phe Asp Ile Asp Gly Asp Leu Ile Arg Val Ala Tyr Pro Ala
65                  70                  75                  80

Gly Leu Phe Glu Pro Gly Asn Met Pro Gln Val Leu Ser Cys Ile Ala
                85                  90                  95

Gly Asn Ile Met Gly Met Lys Ala Val Asp Thr Ile Arg Leu Leu Asp
            100                 105                 110

Cys Glu Trp Pro Glu Ser Val Val Ser Ala Tyr Pro Gly Pro Leu Tyr
        115                 120                 125

Gly Ser Ser Val Arg Glu Glu Ile Phe Gly Val Thr Asp Arg Pro Ile
    130                 135                 140

Thr Ala Thr Val Pro Lys Pro Lys Val Gly Leu Ser Thr Ala Ala His
145                 150                 155                 160

Ala Gln Val Gly Tyr Asp Ala Trp Val Gly Gly Val Asp Leu Leu Lys
                165                 170                 175

Asp Asp Glu Asn Leu Thr Asp Gln Ala Phe Asn Pro Phe Ser Asp Arg
            180                 185                 190

Leu Thr Glu Ser Leu Ser Leu Arg Asp Asp Ala Glu Asp Glu Thr Gly
        195                 200                 205

Glu Thr Lys Ser Tyr Leu Ile Asn Val Thr Ala Asp Thr Arg Thr Met
    210                 215                 220

Leu Asp Arg Val Asp Glu Val Ala Ala Gln Gly Gly Glu Tyr Val Met
225                 230                 235                 240

Val Asp Ile Ile Thr Ala Gly Trp Ala Gly Leu Gln Thr Val Arg Glu
                245                 250                 255

Arg Thr Glu Lys His Gly Leu Ala Ile His Ala His Arg Ala Met His
            260                 265                 270

Ala Ala Phe Asp Arg Leu Pro Ala His Gly Val Ser Met Arg Val Leu
        275                 280                 285

Ala Gln Ile Ser Arg Leu Cys Gly Val Asp Gln Leu His Thr Gly Thr
    290                 295                 300

Ala Gly Leu Gly Lys Leu Ala Asn Glu Asp Thr Val Gly Ile Asn Gly
305                 310                 315                 320

Trp Leu Ala Gly Asp Leu Tyr Gly Thr Thr Asp Val Leu Pro Val Ala
                325                 330                 335

Ser Gly Gly Leu His Pro Gly Leu Leu Pro Asp Leu Leu Asp Ala Thr
            340                 345                 350

Gly Thr Asn Val Cys Val Gln Leu Gly Gly Gly Ile His Gly His Pro
        355                 360                 365

Asp Gly Thr Arg Ser Gly Ala Val Ala Leu Arg Ser Ala Ile Asp Ala
    370                 375                 380

Tyr Val Glu Gly Arg Ser Ile Thr Glu Ala Ala Glu Glu Thr Pro Glu
385                 390                 395                 400

Leu Ala Val Ala Leu Asp Lys Trp Gly Thr Glu Thr Pro Arg
                405                 410

<210> SEQ ID NO 16
<211> LENGTH: 825
<212> TYPE: PRT

<213> ORGANISM: Bifidobacterium breve

<400> SEQUENCE: 16

```
Met Thr Ser Pro Val Ile Gly Thr Pro Trp Lys Lys Leu Asn Ala Pro
1               5                   10                  15
Val Ser Glu Glu Ser Leu Glu Gly Val Asp Lys Tyr Trp Arg Val Ala
            20                  25                  30
Asn Tyr Leu Ser Ile Gly Gln Ile Tyr Leu Arg Ser Asn Pro Leu Met
        35                  40                  45
Lys Ala Pro Phe Thr Arg Glu Asp Val Lys His Arg Leu Val Gly His
    50                  55                  60
Trp Gly Thr Thr Pro Gly Leu Asn Phe Leu Ile Gly His Ile Asn Arg
65                  70                  75                  80
Phe Ile Ala Asp His Gly Gln Asn Thr Val Ile Met Gly Pro Gly
                85                  90                  95
His Gly Gly Pro Ala Gly Thr Ser Gln Ser Tyr Leu Asp Gly Thr Tyr
            100                 105                 110
Thr Glu Thr Phe Pro Lys Ile Thr Lys Asp Glu Ala Gly Leu Gln Lys
        115                 120                 125
Phe Phe Arg Gln Phe Ser Tyr Pro Gly Gly Ile Pro Ser His Phe Ala
    130                 135                 140
Pro Glu Thr Pro Gly Ser Ile His Glu Gly Gly Glu Leu Gly Tyr Ala
145                 150                 155                 160
Leu Ser His Ala Tyr Gly Ala Ile Met Asp Asn Pro Ser Leu Phe Val
                165                 170                 175
Pro Ala Ile Val Gly Asp Gly Glu Ala Glu Thr Gly Pro Leu Ala Thr
            180                 185                 190
Gly Trp Gln Ser Asn Lys Leu Val Asn Pro Arg Thr Asp Gly Ile Val
        195                 200                 205
Leu Pro Ile Leu His Leu Asn Gly Tyr Lys Ile Ala Asn Pro Thr Ile
    210                 215                 220
Leu Ser Arg Ile Ser Asp Glu Glu Leu His Glu Phe Phe His Gly Met
225                 230                 235                 240
Gly Tyr Glu Pro Tyr Glu Phe Val Ala Gly Phe Asp Asp Glu Asp His
                245                 250                 255
Met Ser Ile His Arg Arg Phe Ala Glu Leu Trp Glu Thr Ile Trp Asp
            260                 265                 270
Glu Ile Cys Asp Ile Lys Ala Ala Gln Thr Asp Asn Val His Arg
        275                 280                 285
Pro Phe Tyr Pro Met Leu Ile Phe Arg Thr Pro Lys Gly Trp Thr Cys
    290                 295                 300
Pro Lys Tyr Ile Asp Gly Lys Lys Thr Glu Gly Ser Trp Arg Ala His
305                 310                 315                 320
Gln Val Pro Leu Ala Ser Ala Arg Asp Thr Glu Ala His Phe Glu Val
                325                 330                 335
Leu Lys Asn Trp Leu Glu Ser Tyr Lys Pro Glu Glu Leu Phe Asp Ala
            340                 345                 350
Asn Gly Ala Val Lys Asp Asp Val Leu Ala Phe Met Pro Lys Gly Glu
        355                 360                 365
Leu Arg Ile Gly Ala Asn Pro Asn Ala Asn Gly Gly Val Ile Arg Asp
    370                 375                 380
Asp Leu Lys Leu Pro Asn Leu Glu Asp Tyr Glu Val Lys Glu Val Ala
385                 390                 395                 400
```

```
Glu Tyr Gly His Gly Trp Gly Gln Leu Glu Ala Thr Arg Thr Leu Gly
                405                 410                 415
Ala Tyr Thr Arg Asp Ile Ile Arg Asn Asn Pro Arg Asp Phe Arg Ile
                420                 425                 430
Phe Gly Pro Asp Glu Thr Ala Ser Asn Arg Leu Gln Ala Ser Tyr Glu
                435                 440                 445
Val Thr Asn Lys Gln Trp Asp Ala Gly Tyr Ile Ser Asp Glu Val Asp
                450                 455                 460
Glu His Met His Val Ser Gly Gln Val Val Glu Gln Leu Ser Glu His
465                 470                 475                 480
Gln Met Glu Gly Phe Leu Glu Ala Tyr Leu Leu Thr Gly Arg His Gly
                485                 490                 495
Ile Trp Ser Ser Tyr Glu Ser Phe Val His Val Ile Asp Ser Met Leu
                500                 505                 510
Asn Gln His Ala Lys Trp Leu Glu Ala Thr Val Arg Glu Ile Pro Trp
                515                 520                 525
Arg Lys Pro Ile Ala Ser Met Asn Leu Leu Val Ser Ser His Val Trp
                530                 535                 540
Arg Gln Asp His Asn Gly Phe Ser His Gln Asp Pro Gly Val Thr Ser
545                 550                 555                 560
Val Leu Leu Asn Lys Cys Phe His Asn Asp His Val Ile Gly Ile Tyr
                565                 570                 575
Phe Ala Thr Asp Ala Asn Met Leu Leu Ala Ile Ala Glu Lys Cys Tyr
                580                 585                 590
Lys Ser Thr Asn Lys Ile Asn Ala Ile Ile Ala Gly Lys Gln Pro Ala
                595                 600                 605
Ala Thr Trp Leu Thr Leu Asp Glu Ala Arg Ala Glu Leu Ala Lys Gly
                610                 615                 620
Ala Ala Ala Trp Asp Trp Ala Ser Thr Ala Lys Asn Asn Asp Glu Ala
625                 630                 635                 640
Glu Val Val Leu Ala Ala Ala Gly Asp Val Pro Thr Gln Glu Ile Met
                645                 650                 655
Ala Ala Ser Asp Lys Leu Lys Glu Leu Gly Val Lys Phe Lys Val Val
                660                 665                 670
Asn Val Ala Asp Leu Leu Ser Leu Gln Ser Ala Lys Glu Asn Asp Glu
                675                 680                 685
Ala Leu Ser Asp Glu Glu Phe Ala Asp Ile Phe Thr Ala Asp Lys Pro
                690                 695                 700
Val Leu Phe Ala Tyr His Ser Tyr Ala His Asp Val Arg Gly Leu Ile
705                 710                 715                 720
Tyr Asp Arg Pro Asn His Asp Asn Phe Asn Val His Gly Tyr Glu Glu
                725                 730                 735
Glu Gly Ser Thr Thr Thr Pro Tyr Asp Met Val Arg Val Asn Arg Ile
                740                 745                 750
Asp Arg Tyr Glu Leu Thr Ala Glu Ala Leu Arg Met Ile Asp Ala Asp
                755                 760                 765
Lys Tyr Ala Asp Lys Ile Asp Glu Leu Glu Lys Phe Arg Asp Glu Ala
                770                 775                 780
Phe Gln Phe Ala Val Asp Lys Gly Tyr Asp His Pro Asp Tyr Thr Asp
785                 790                 795                 800
Trp Val Tyr Ser Gly Val Asn Thr Asp Lys Lys Gly Ala Val Thr Ala
                805                 810                 815
Thr Ala Ala Thr Ala Gly Asp Asn Glu
```

<210> SEQ ID NO 17
<211> LENGTH: 796
<212> TYPE: PRT
<213> ORGANISM: Clostridium acetobutylicum

<400> SEQUENCE: 17

Met Gln Ser Ile Ile Gly Lys His Lys Asp Glu Gly Lys Ile Thr Pro
1               5                   10                  15

Glu Tyr Leu Lys Lys Ile Asp Ala Tyr Trp Arg Ala Ala Asn Phe Ile
            20                  25                  30

Ser Val Gly Gln Leu Tyr Leu Leu Asp Asn Pro Leu Leu Arg Glu Pro
        35                  40                  45

Leu Lys Pro Glu His Leu Lys Arg Lys Val Val Gly His Trp Gly Thr
50                  55                  60

Ile Pro Gly Gln Asn Phe Ile Tyr Ala His Leu Asn Arg Val Ile Lys
65                  70                  75                  80

Lys Tyr Asp Leu Asp Met Ile Tyr Val Ser Gly Pro Gly His Gly Gly
                85                  90                  95

Gln Val Met Val Ser Asn Ser Tyr Leu Asp Gly Thr Tyr Ser Glu Val
            100                 105                 110

Tyr Pro Asn Val Ser Arg Asp Leu Asn Gly Leu Lys Lys Leu Cys Lys
        115                 120                 125

Gln Phe Ser Phe Pro Gly Gly Ile Ser Ser His Met Ala Pro Glu Thr
130                 135                 140

Pro Gly Ser Ile Asn Glu Gly Gly Glu Leu Gly Tyr Ser Leu Ala His
145                 150                 155                 160

Ser Phe Gly Ala Val Phe Asp Asn Pro Asp Leu Ile Thr Ala Cys Val
                165                 170                 175

Val Gly Asp Gly Glu Ala Glu Thr Gly Pro Leu Ala Thr Ser Trp Gln
            180                 185                 190

Ala Asn Lys Phe Leu Asn Pro Val Thr Asp Gly Ala Val Leu Pro Ile
        195                 200                 205

Leu His Leu Asn Gly Tyr Lys Ile Ser Asn Pro Thr Val Leu Ser Arg
210                 215                 220

Ile Pro Lys Asp Glu Leu Glu Lys Phe Phe Glu Gly Asn Gly Trp Lys
225                 230                 235                 240

Pro Tyr Phe Val Glu Gly Glu Asp Pro Glu Ala Met His Lys Leu Met
                245                 250                 255

Ala Glu Thr Leu Asp Ile Val Thr Glu Ile Leu Asn Ile Gln Lys
            260                 265                 270

Asn Ala Arg Glu Asn Asn Asp Cys Ser Arg Pro Lys Trp Pro Met Ile
        275                 280                 285

Val Leu Arg Thr Pro Lys Gly Trp Thr Gly Pro Lys Phe Val Asp Gly
290                 295                 300

Val Pro Asn Glu Gly Ser Phe Arg Ala His Gln Val Pro Leu Ala Val
305                 310                 315                 320

Asp Arg Tyr His Thr Glu Asn Leu Asp Gln Leu Glu Glu Trp Leu Lys
                325                 330                 335

Ser Tyr Lys Pro Glu Glu Leu Phe Asp Glu Asn Tyr Arg Leu Ile Pro
            340                 345                 350

Glu Leu Glu Glu Leu Thr Pro Lys Gly Asn Lys Arg Met Ala Ala Asn
        355                 360                 365

-continued

```
Leu His Ala Asn Gly Gly Leu Leu Arg Glu Leu Arg Thr Pro Asp
370                 375                 380

Phe Arg Asp Tyr Ala Val Asp Val Pro Thr Pro Gly Ser Thr Val Lys
385                 390                 395                 400

Gln Asp Met Ile Glu Leu Gly Lys Tyr Val Arg Asp Val Val Lys Leu
                405                 410                 415

Asn Glu Asp Thr Arg Asn Phe Arg Ile Phe Gly Pro Asp Glu Thr Met
                420                 425                 430

Ser Asn Arg Leu Trp Ala Val Phe Glu Gly Thr Lys Arg Gln Trp Leu
            435                 440                 445

Ser Glu Ile Lys Glu Pro Asn Asp Glu Phe Leu Ser Asn Asp Gly Arg
450                 455                 460

Ile Val Asp Ser Met Leu Ser Glu His Leu Cys Glu Gly Trp Leu Glu
465                 470                 475                 480

Gly Tyr Leu Leu Thr Gly Arg His Gly Phe Phe Ala Ser Tyr Glu Ala
                485                 490                 495

Phe Leu Arg Ile Val Asp Ser Met Ile Thr Gln His Gly Lys Trp Leu
                500                 505                 510

Lys Val Thr Ser Gln Leu Pro Trp Arg Lys Asp Ile Ala Ser Leu Asn
            515                 520                 525

Leu Ile Ala Thr Ser Asn Val Trp Gln Gln Asp His Asn Gly Tyr Thr
530                 535                 540

His Gln Asp Pro Gly Leu Leu Gly His Ile Val Asp Lys Lys Pro Glu
545                 550                 555                 560

Ile Val Arg Ala Tyr Leu Pro Ala Asp Ala Asn Thr Leu Leu Ala Val
                565                 570                 575

Phe Asp Lys Cys Leu His Thr Lys His Lys Ile Asn Leu Leu Val Thr
                580                 585                 590

Ser Lys His Pro Arg Gln Gln Trp Leu Thr Met Asp Gln Ala Val Lys
            595                 600                 605

His Val Glu Gln Gly Ile Ser Ile Trp Asp Trp Ala Ser Asn Asp Lys
610                 615                 620

Gly Gln Glu Pro Asp Val Val Ile Ala Ser Cys Gly Asp Thr Pro Thr
625                 630                 635                 640

Leu Glu Ala Leu Ala Ala Val Thr Ile Leu His Glu His Leu Pro Glu
                645                 650                 655

Leu Lys Val Arg Phe Val Asn Val Val Asp Met Met Lys Leu Leu Pro
                660                 665                 670

Glu Asn Glu His Pro His Gly Leu Ser Asp Lys Asp Tyr Asn Ala Leu
            675                 680                 685

Phe Thr Thr Asp Lys Pro Val Ile Phe Ala Phe His Gly Phe Ala His
690                 695                 700

Leu Ile Asn Gln Leu Thr Tyr His Arg Glu Asn Arg Asn Leu His Val
705                 710                 715                 720

His Gly Tyr Met Glu Glu Gly Thr Ile Thr Thr Pro Phe Asp Met Arg
                725                 730                 735

Val Gln Asn Lys Leu Asp Arg Phe Asn Leu Val Lys Asp Val Val Glu
                740                 745                 750

Asn Leu Pro Gln Leu Gly Asn Arg Gly Ala His Leu Val Gln Leu Met
            755                 760                 765

Asn Asp Lys Leu Val Glu His Asn Gln Tyr Ile Arg Glu Val Gly Glu
770                 775                 780

Asp Leu Pro Glu Ile Thr Asn Trp Gln Trp His Val
```

<210> SEQ ID NO 18
<211> LENGTH: 813
<212> TYPE: PRT
<213> ORGANISM: Leuconostoc mesenteroides

<400> SEQUENCE: 18

```
Met Ala Asp Phe Asp Ser Lys Glu Tyr Leu Glu Leu Val Asp Lys Trp
 1               5                  10                  15

Trp Arg Ala Thr Asn Tyr Leu Ser Ala Gly Met Ile Phe Leu Lys Ser
                20                  25                  30

Asn Pro Leu Phe Ser Val Thr Asn Thr Pro Ile Lys Ala Glu Asp Val
            35                  40                  45

Lys Val Lys Pro Ile Gly His Trp Gly Thr Ile Ser Gly Gln Thr Phe
 50                  55                  60

Leu Tyr Ala His Ala Asn Arg Leu Ile Asn Lys Tyr Gly Leu Asn Met
 65                  70                  75                  80

Phe Tyr Val Gly Gly Pro Gly His Gly Gln Val Met Val Thr Asn
                 85                  90                  95

Ala Tyr Leu Asp Gly Ala Tyr Thr Glu Asp Tyr Pro Glu Ile Thr Gln
                100                 105                 110

Asp Ile Glu Gly Met Ser His Leu Phe Lys Arg Phe Ser Phe Pro Gly
            115                 120                 125

Gly Ile Gly Ser His Met Thr Ala Gln Thr Pro Gly Ser Leu His Glu
130                 135                 140

Gly Gly Glu Leu Gly Tyr Ser Leu Ser His Ala Phe Gly Ala Val Leu
145                 150                 155                 160

Asp Asn Pro Asp Gln Val Ala Phe Ala Val Val Gly Asp Gly Glu Ala
                165                 170                 175

Glu Thr Gly Pro Ser Met Ala Ser Trp His Ser Ile Lys Phe Leu Asn
            180                 185                 190

Ala Lys Asn Asp Gly Ala Val Leu Pro Val Leu Asp Leu Asn Gly Phe
        195                 200                 205

Lys Ile Ser Asn Pro Thr Ile Phe Ser Arg Met Ser Asp Glu Glu Ile
210                 215                 220

Thr Lys Phe Phe Glu Gly Leu Gly Tyr Ser Pro Arg Phe Ile Glu Asn
225                 230                 235                 240

Asp Asp Ile His Asp Tyr Ala Thr Tyr His Gln Leu Ala Ala Asn Ile
                245                 250                 255

Leu Asp Gln Ala Ile Glu Asp Ile Gln Ala Ile Gln Asn Asp Ala Arg
            260                 265                 270

Glu Asn Gly Lys Tyr Gln Asp Gly Glu Ile Pro Ala Trp Pro Val Ile
        275                 280                 285

Ile Ala Arg Leu Pro Lys Gly Trp Gly Gly Pro Thr His Asp Ala Ser
290                 295                 300

Asn Asn Pro Ile Glu Asn Ser Phe Arg Ala His Gln Val Pro Leu Pro
305                 310                 315                 320

Leu Glu Gln His Asp Leu Ala Thr Leu Pro Glu Phe Glu Asp Trp Met
                325                 330                 335

Asn Ser Tyr Lys Pro Glu Glu Leu Phe Asn Ala Asp Gly Ser Leu Lys
            340                 345                 350

Asp Glu Leu Lys Ala Ile Ala Pro Lys Gly Asp Lys Arg Met Ser Ala
        355                 360                 365
```

```
Asn Pro Ile Thr Asn Gly Gly Ala Asp Arg Ser Asp Leu Lys Leu Pro
370                 375                 380
Asn Trp Arg Glu Phe Ala Asn Asp Ile Asn Asp Asp Thr Arg Gly Lys
385                 390                 395                 400
Glu Phe Ala Asp Ser Lys Arg Asn Met Asp Met Ala Thr Leu Ser Asn
                405                 410                 415
Tyr Leu Gly Ala Val Ser Gln Leu Asn Pro Thr Arg Phe Arg Phe Phe
                420                 425                 430
Gly Pro Asp Glu Thr Met Ser Asn Arg Leu Trp Gly Leu Phe Asn Val
            435                 440                 445
Thr Pro Arg Gln Trp Met Glu Glu Ile Lys Glu Pro Gln Asp Gln Leu
450                 455                 460
Leu Ser Pro Thr Gly Arg Ile Ile Asp Ser Gln Leu Ser Glu His Gln
465                 470                 475                 480
Ala Glu Gly Trp Leu Glu Gly Tyr Thr Leu Thr Gly Arg Val Gly Ile
                485                 490                 495
Phe Ala Ser Tyr Glu Ser Phe Leu Arg Val Val Asp Thr Met Val Thr
                500                 505                 510
Gln His Phe Lys Trp Leu Arg His Ala Ser Glu Gln Ala Trp Arg Asn
            515                 520                 525
Asp Tyr Pro Ser Leu Asn Leu Ile Ala Thr Ser Thr Ala Phe Gln Gln
530                 535                 540
Asp His Asn Gly Tyr Thr His Gln Asp Pro Gly Met Leu Thr His Leu
545                 550                 555                 560
Ala Glu Lys Lys Ser Asn Phe Ile Arg Glu Tyr Leu Pro Ala Asp Gly
                565                 570                 575
Asn Ser Leu Leu Ala Val Gln Glu Arg Ala Phe Ser Glu Arg His Lys
            580                 585                 590
Val Asn Leu Leu Ile Ala Ser Lys Gln Pro Arg Gln Trp Phe Thr
            595                 600                 605
Val Glu Glu Ala Glu Val Leu Ala Asn Glu Gly Leu Lys Ile Ile Asp
        610                 615                 620
Trp Ala Ser Thr Ala Pro Ser Ser Asp Val Asp Ile Thr Phe Ala Ser
625                 630                 635                 640
Ala Gly Thr Glu Pro Thr Ile Glu Thr Leu Ala Ala Leu Trp Leu Ile
                645                 650                 655
Asn Gln Ala Phe Pro Asp Val Lys Phe Arg Tyr Val Asn Val Val Glu
            660                 665                 670
Leu Leu Arg Leu Gln Lys Lys Ser Glu Pro Asn Met Asn Asp Glu Arg
        675                 680                 685
Glu Leu Ser Ala Glu Glu Phe Asn Lys Tyr Phe Gln Ala Asp Thr Pro
    690                 695                 700
Val Ile Phe Gly Phe His Ala Tyr Glu Asn Leu Ile Glu Ser Phe Phe
705                 710                 715                 720
Phe Glu Arg Lys Phe Thr Gly Asp Val Tyr Val His Gly Tyr Arg Glu
                725                 730                 735
Asp Gly Asp Ile Thr Thr Thr Tyr Asp Met Arg Val Tyr Ser His Leu
            740                 745                 750
Asp Arg Phe His Gln Ala Lys Glu Ala Ala Glu Ile Leu Ser Ala Asn
        755                 760                 765
Gly Lys Ile Asp Gln Ala Ala Ala Asp Thr Phe Ile Ala Lys Met Asp
770                 775                 780
Asp Thr Leu Ala Lys His Phe Gln Val Thr Arg Asn Glu Gly Arg Asp
```

```
                785                 790                 795                 800
Ile Glu Glu Phe Thr Asp Trp Thr Trp Ser Pro Leu Lys
                    805                 810

<210> SEQ ID NO 19
<211> LENGTH: 323
<212> TYPE: PRT
<213> ORGANISM: B. subtilis

<400> SEQUENCE: 19

Met Ala Asp Leu Phe Ser Thr Val Gln Glu Lys Val Ala Gly Lys Asp
1               5                   10                  15

Val Lys Ile Val Phe Pro Glu Gly Leu Asp Glu Arg Ile Leu Glu Ala
            20                  25                  30

Val Ser Lys Leu Ala Gly Asn Lys Val Leu Asn Pro Ile Val Ile Gly
        35                  40                  45

Asn Glu Asn Glu Ile Gln Ala Lys Ala Lys Glu Leu Asn Leu Thr Leu
    50                  55                  60

Gly Gly Val Lys Ile Tyr Asp Pro His Thr Tyr Glu Gly Met Glu Asp
65                  70                  75                  80

Leu Val Gln Ala Phe Val Glu Arg Arg Lys Gly Lys Ala Thr Glu Glu
                85                  90                  95

Gln Ala Arg Lys Ala Leu Leu Asp Glu Asn Tyr Phe Gly Thr Met Leu
            100                 105                 110

Val Tyr Lys Gly Leu Ala Asp Gly Leu Val Ser Gly Ala Ala His Ser
        115                 120                 125

Thr Ala Asp Thr Val Arg Pro Ala Leu Gln Ile Ile Lys Thr Lys Glu
130                 135                 140

Gly Val Lys Lys Thr Ser Gly Val Phe Ile Met Ala Arg Gly Glu Glu
145                 150                 155                 160

Gln Tyr Val Phe Ala Asp Cys Ala Ile Asn Ile Ala Pro Asp Ser Gln
                165                 170                 175

Asp Leu Ala Glu Ile Ala Ile Glu Ser Ala Asn Thr Ala Lys Met Phe
            180                 185                 190

Asp Ile Glu Pro Arg Val Ala Met Leu Ser Phe Ser Thr Lys Gly Ser
        195                 200                 205

Ala Lys Ser Asp Glu Thr Glu Lys Val Ala Asp Ala Val Lys Ile Ala
    210                 215                 220

Lys Glu Lys Ala Pro Glu Leu Thr Leu Asp Gly Glu Phe Gln Phe Asp
225                 230                 235                 240

Ala Ala Phe Val Pro Ser Val Ala Glu Lys Lys Ala Pro Asp Ser Glu
                245                 250                 255

Ile Lys Gly Asp Ala Asn Val Phe Val Phe Pro Ser Leu Glu Ala Gly
            260                 265                 270

Asn Ile Gly Tyr Lys Ile Ala Gln Arg Leu Gly Asn Phe Glu Ala Val
        275                 280                 285

Gly Pro Ile Leu Gln Gly Leu Asn Met Pro Val Asn Asp Leu Ser Arg
    290                 295                 300

Gly Cys Asn Ala Glu Asp Val Tyr Asn Leu Ala Leu Ile Thr Ala Ala
305                 310                 315                 320

Gln Ala Leu

<210> SEQ ID NO 20
<211> LENGTH: 563
<212> TYPE: PRT
```

<213> ORGANISM: B. adolescentis

<400> SEQUENCE: 20

```
Met Lys Tyr Ile Gly Asp Thr Val Ser Phe Thr Ser Val Thr Ile Ile
1               5                   10                  15

Ser Pro Glu Ala Ala Asn Gly Arg Asn Val Val Ala Leu Gly Val Thr
            20                  25                  30

Lys Ala Leu Ala Ala Ala Gly Lys Thr Gly Val Phe Arg Pro Ala Val
        35                  40                  45

Cys Arg Lys Asp Thr Phe Thr Asp Val Leu Ile Glu Ala Ser Asn Ala
    50                  55                  60

Gly Leu Ser Arg Glu Gln Ser Val Gly Val Cys Pro Lys Arg Ala Arg
65                  70                  75                  80

Asn Asp Lys Glu Gly Ser Arg Ala Asp Ile Val Ala Ala Tyr Thr Gln
                85                  90                  95

Ala Val Glu Thr Ala Arg Pro Asp Ala Met Val Ile Val Gly Thr Asp
            100                 105                 110

Arg Ser Ala Val Asn Asp Pro Ala Met Phe Ser Phe Asn Ala Asp Phe
        115                 120                 125

Ala Ala Asp Leu Gln Ser Pro Val Leu Leu Ala Val Cys Thr Ile Glu
    130                 135                 140

Arg Thr Pro Glu Gln Val Lys Ser Thr Val Glu Ala Ser Thr Lys Val
145                 150                 155                 160

Ile Glu Asp Ala Gly Ser Lys Val Val Gly Val Phe Ile Thr Gly Cys
                165                 170                 175

Asp Asp Thr Gln Pro Asp Pro Leu Lys Ala Cys Phe Val Asp Tyr Pro
            180                 185                 190

Val Pro Val Trp Thr Leu Pro Ala Val Asp Phe Asn Asp Asp Asp Ala
        195                 200                 205

Ile Ser Lys Ala Asp Glu Ala Phe Ala Thr Asn Val Asp Ala Ala Glu
    210                 215                 220

Leu Thr Ala Ala Leu Glu Ser Pro Phe Asp Ala Pro Thr Thr Pro Tyr
225                 230                 235                 240

Ala Phe Gln Tyr Gly Leu Leu Gly Lys Ala Lys Ala Asp Lys Lys Thr
                245                 250                 255

Ile Val Leu Pro Glu Gly Asn Glu Asp Arg Ile Ile Lys Ala Ala Asp
            260                 265                 270

Tyr Leu Leu Glu Arg Asp Ile Val Asp Leu Ile Ile Val Gly Asp Glu
        275                 280                 285

Asn Ala Ile Leu Ala Arg Gly Gln Glu Leu Gly Leu Lys Ser Leu Gly
    290                 295                 300

Lys Ala Lys Phe Gln Ala Lys Asp Asp Glu Thr Val Leu Glu Pro Met
305                 310                 315                 320

Val Ala Lys Leu Cys Glu Leu Arg Ala Lys Gly Met Thr Glu Glu
                325                 330                 335

Gln Ala Arg Lys Gln Leu Ala Asp Asp Ser Tyr Phe Gly Thr Met Leu
            340                 345                 350

Val Val Met Gly Met Ala Asp Gly Leu Val Ser Gly Ser Val Asn Ser
        355                 360                 365

Thr Ala Asn Thr Val Arg Pro Ala Leu Gln Val Ile Lys Thr Lys Pro
    370                 375                 380

Gly Thr Ser Leu Val Ser Gly Ala Phe Leu Met Cys Phe Lys Asp His
385                 390                 395                 400
```

```
Val Ala Val Phe Ala Asp Cys Ala Ile Asn Leu Asn Pro Asn Ala Glu
                405                 410                 415

Gln Leu Ala Glu Ile Ala Ile Gln Ser Ala Glu Thr Ala Lys Ala Phe
            420                 425                 430

Gly Leu Glu Pro Lys Val Gly Met Leu Ser Tyr Ser Thr Leu Gly Ser
        435                 440                 445

Gly Lys Gly Pro Asp Val Asp Leu Val Glu Glu Ala Thr Thr Ile Val
450                 455                 460

Lys Asp Lys Ala Pro Asp Leu Ala Val Val Gly Ser Ile Gln Phe Asp
465                 470                 475                 480

Ala Ala Trp Ser Pro Thr Val Ala Thr Lys Ala Lys Gly Asp Pro
                485                 490                 495

Val Ala Gly His Val Asn Val Phe Val Phe Pro Asp Leu Cys Ala Gly
                500                 505                 510

Asn Ile Ala Tyr Lys Ala Val Gln Arg Ser Ser Gly Ala Ala Ala Val
                515                 520                 525

Gly Pro Val Leu Gln Gly Leu Asn Arg Pro Val Asn Asp Leu Ser Arg
                530                 535                 540

Gly Ala Thr Val Gln Asp Ile Ile Asn Thr Ile Ala Leu Thr Ala Ile
545                 550                 555                 560

Glu Ala Gln

<210> SEQ ID NO 21
<211> LENGTH: 325
<212> TYPE: PRT
<213> ORGANISM: L. plantarum

<400> SEQUENCE: 21

Met Asp Leu Phe Glu Ser Leu Ala Gln Lys Ile Thr Gly Lys Asp Gln
1               5                   10                  15

Thr Ile Val Phe Pro Glu Gly Thr Glu Pro Arg Ile Val Gly Ala Ala
                20                  25                  30

Ala Arg Leu Ala Ala Asp Gly Leu Val Lys Pro Ile Val Leu Gly Ala
            35                  40                  45

Thr Asp Lys Val Gln Ala Val Ala Asn Asp Leu Asn Ala Asp Leu Thr
50                  55                  60

Gly Val Gln Val Leu Asp Pro Ala Thr Tyr Pro Ala Glu Asp Lys Gln
65                  70                  75                  80

Ala Met Leu Asp Ala Leu Val Glu Arg Arg Lys Gly Lys Asn Thr Pro
                85                  90                  95

Glu Gln Ala Ala Lys Met Leu Glu Asp Glu Asn Tyr Phe Gly Thr Met
            100                 105                 110

Leu Val Tyr Met Gly Lys Ala Asp Gly Met Val Ser Gly Ala Ile His
        115                 120                 125

Pro Thr Gly Asp Thr Val Arg Pro Ala Leu Gln Ile Ile Lys Thr Lys
130                 135                 140

Pro Gly Ser His Arg Ile Ser Gly Ala Phe Ile Met Gln Lys Gly Glu
145                 150                 155                 160

Glu Arg Tyr Val Phe Ala Asp Cys Ala Ile Asn Ile Asp Pro Asp Ala
                165                 170                 175

Asp Thr Leu Ala Glu Ile Ala Thr Gln Ser Ala Ala Thr Ala Lys Val
            180                 185                 190

Phe Asp Ile Asp Pro Lys Val Ala Met Leu Ser Phe Ser Thr Lys Gly
        195                 200                 205
```

```
Ser Ala Lys Gly Glu Met Val Thr Lys Val Gln Glu Ala Thr Ala Lys
    210                 215                 220

Ala Gln Ala Ala Glu Pro Glu Leu Ala Ile Asp Gly Glu Leu Gln Phe
225                 230                 235                 240

Asp Ala Ala Phe Val Glu Lys Val Gly Leu Gln Lys Ala Pro Gly Ser
                245                 250                 255

Lys Val Ala Gly His Ala Asn Val Phe Val Phe Pro Glu Leu Gln Ser
                260                 265                 270

Gly Asn Ile Gly Tyr Lys Ile Ala Gln Arg Phe Gly His Phe Glu Ala
                275                 280                 285

Val Gly Pro Val Leu Gln Gly Leu Asn Lys Pro Val Ser Asp Leu Ser
290                 295                 300

Arg Gly Cys Ser Glu Glu Asp Val Tyr Lys Val Ala Ile Ile Thr Ala
305                 310                 315                 320

Ala Gln Gly Leu Ala
                325

<210> SEQ ID NO 22
<211> LENGTH: 870
<212> TYPE: PRT
<213> ORGANISM: E. histolytica

<400> SEQUENCE: 22

Met Ser Thr Gln Gln Thr Met Thr Val Asp Glu His Ile Asn Gln Leu
1               5                   10                  15

Val Arg Lys Ala Gln Val Ala Leu Lys Glu Tyr Leu Lys Pro Glu Tyr
                20                  25                  30

Thr Gln Glu Lys Ile Asp Tyr Ile Val Lys Lys Ala Ser Val Ala Ala
                35                  40                  45

Leu Asp Gln His Cys Ala Leu Ala Ala Ala Val Glu Glu Thr Gly
    50                  55                  60

Arg Gly Ile Phe Glu Asp Lys Ala Thr Lys Asn Ile Phe Ala Cys Glu
65                  70                  75                  80

His Val Thr His Glu Met Arg His Ala Lys Thr Val Gly Ile Ile Asn
                85                  90                  95

Val Asp Pro Leu Tyr Gly Ile Thr Glu Ile Ala Glu Pro Val Gly Val
                100                 105                 110

Val Cys Gly Val Thr Pro Val Thr Asn Pro Thr Ser Thr Ala Ile Phe
            115                 120                 125

Lys Ser Leu Ile Ser Ile Lys Thr Arg Asn Pro Ile Val Phe Ser Phe
130                 135                 140

His Pro Ser Ala Leu Lys Cys Ser Ile Met Ala Ala Lys Ile Val Arg
145                 150                 155                 160

Asp Ala Ala Ile Ala Ala Gly Ala Pro Glu Asn Cys Ile Gln Trp Ile
                165                 170                 175

Glu Phe Gly Gly Ile Glu Ala Ser Asn Lys Leu Met Asn His Pro Gly
                180                 185                 190

Val Ala Thr Ile Leu Ala Thr Gly Gly Asn Ala Met Val Lys Ala Ala
            195                 200                 205

Tyr Ser Ser Gly Lys Pro Ala Leu Gly Val Gly Ala Gly Asn Val Pro
    210                 215                 220

Thr Tyr Ile Glu Lys Thr Cys Asn Ile Lys Gln Ala Ala Asn Asp Val
225                 230                 235                 240

Val Met Ser Lys Ser Phe Asp Asn Gly Met Ile Cys Ala Ser Glu Gln
                245                 250                 255
```

```
Ala Ala Ile Ile Asp Lys Glu Ile Tyr Asp Gln Val Glu Glu Met
            260                 265                 270

Lys Thr Leu Gly Ala Tyr Phe Ile Asn Glu Glu Lys Ala Lys Leu
            275                 280                 285

Glu Lys Phe Met Phe Gly Val Asn Ala Tyr Ser Ala Asp Val Asn Asn
            290                 295                 300

Ala Arg Leu Asn Pro Lys Cys Pro Gly Met Ser Pro Gln Trp Phe Ala
305                 310                 315                 320

Glu Gln Val Gly Ile Lys Val Pro Glu Asp Cys Asn Ile Ile Cys Ala
                    325                 330                 335

Val Cys Lys Glu Val Gly Pro Asn Glu Pro Leu Thr Arg Glu Lys Leu
                340                 345                 350

Ser Pro Val Leu Ala Ile Leu Lys Ala Glu Asn Thr Gln Asp Gly Ile
            355                 360                 365

Asp Lys Ala Glu Ala Met Val Glu Phe Asn Gly Arg Gly His Ser Ala
            370                 375                 380

Ala Ile His Ser Asn Asp Lys Ala Val Val Glu Lys Tyr Ala Leu Thr
385                 390                 395                 400

Met Lys Ala Cys Arg Ile Leu His Asn Thr Pro Ser Ser Gln Gly Gly
                405                 410                 415

Ile Gly Ser Ile Tyr Asn Tyr Ile Trp Pro Ser Phe Thr Leu Gly Cys
                420                 425                 430

Gly Ser Tyr Gly Gly Asn Ser Val Ser Ala Asn Val Thr Tyr His Asn
            435                 440                 445

Leu Leu Asn Ile Lys Arg Leu Ala Asp Arg Arg Asn Asn Leu Gln Trp
450                 455                 460

Phe Arg Val Pro Pro Lys Ile Phe Phe Glu Pro His Ser Ile Arg Tyr
465                 470                 475                 480

Leu Ala Glu Leu Lys Glu Leu Ser Lys Ile Phe Ile Val Ser Asp Arg
                485                 490                 495

Met Met Tyr Lys Leu Gly Tyr Val Asp Arg Val Met Asp Val Leu Lys
                500                 505                 510

Arg Arg Ser Asn Glu Val Glu Ile Glu Ile Phe Ile Asp Val Glu Pro
                515                 520                 525

Asp Pro Ser Ile Gln Thr Val Gln Lys Gly Leu Ala Val Met Asn Thr
530                 535                 540

Phe Gly Pro Asp Asn Ile Ile Ala Ile Gly Gly Gly Ser Ala Met Asp
545                 550                 555                 560

Ala Ala Lys Ile Met Trp Leu Leu Tyr Glu His Pro Glu Ala Asp Phe
                565                 570                 575

Phe Ala Met Lys Gln Lys Phe Ile Asp Leu Arg Lys Arg Ala Phe Lys
            580                 585                 590

Phe Pro Thr Met Gly Lys Lys Ala Arg Leu Ile Cys Ile Pro Thr Thr
            595                 600                 605

Ser Gly Thr Gly Ser Glu Val Thr Pro Phe Ala Val Ile Ser Asp His
            610                 615                 620

Glu Thr Gly Lys Lys Tyr Pro Leu Ala Asp Tyr Ser Leu Thr Pro Ser
625                 630                 635                 640

Val Ala Ile Val Asp Pro Met Phe Thr Met Ser Leu Pro Lys Arg Ala
                645                 650                 655

Ile Ala Asp Thr Gly Leu Asp Val Leu Val His Ala Thr Glu Ala Tyr
                660                 665                 670
```

```
Val Ser Val Met Ala Asn Glu Tyr Thr Asp Gly Leu Ala Arg Glu Ala
            675                 680                 685

Val Lys Leu Val Phe Glu Asn Leu Leu Lys Ser Tyr Asn Gly Asp Leu
    690                 695                 700

Glu Ala Arg Glu Lys Met His Asn Ala Ala Thr Ile Ala Gly Met Ala
705                 710                 715                 720

Phe Ala Ser Ala Phe Leu Gly Met Asp His Ser Met Ala His Lys Val
                725                 730                 735

Gly Ala Ala Phe His Leu Pro His Gly Arg Cys Val Ala Val Leu Leu
                740                 745                 750

Pro His Val Ile Arg Tyr Asn Gly Gln Lys Pro Arg Lys Leu Ala Met
        755                 760                 765

Trp Pro Lys Tyr Asn Phe Tyr Lys Ala Asp Gln Arg Tyr Met Glu Leu
    770                 775                 780

Ala Gln Met Val Gly Leu Lys Cys Asn Thr Pro Ala Glu Gly Val Glu
785                 790                 795                 800

Ala Phe Ala Lys Ala Cys Glu Glu Leu Met Lys Ala Thr Glu Thr Ile
                805                 810                 815

Thr Gly Phe Lys Lys Ala Asn Ile Asp Glu Ala Ala Trp Met Ser Lys
                820                 825                 830

Val Pro Glu Met Ala Leu Leu Ala Phe Glu Asp Gln Cys Ser Pro Ala
        835                 840                 845

Asn Pro Arg Val Pro Met Val Lys Asp Met Glu Lys Ile Leu Lys Ala
    850                 855                 860

Ala Tyr Tyr Pro Ile Ala
865                 870

<210> SEQ ID NO 23
<211> LENGTH: 909
<212> TYPE: PRT
<213> ORGANISM: B. adolescentis

<400> SEQUENCE: 23

Met Ala Asp Ala Lys Lys Glu Glu Pro Thr Lys Pro Thr Pro Glu Glu
1               5                   10                  15

Lys Leu Ala Ala Ala Glu Ala Glu Val Asp Ala Leu Val Lys Lys Gly
                20                  25                  30

Leu Lys Ala Leu Asp Asp Phe Glu Lys Leu Asp Gln Lys Gln Val Asp
            35                  40                  45

Arg Ile Val Ala Lys Ala Ser Val Ala Ala Leu Asn Lys His Leu Val
    50                  55                  60

Leu Ala Lys Met Ala Val Glu Glu Thr His Arg Gly Leu Val Glu Asp
65                  70                  75                  80

Lys Ala Thr Lys Asn Ile Phe Ala Cys Glu His Val Thr Asn Tyr Leu
                85                  90                  95

Ala Gly Gln Lys Thr Val Gly Ile Ile Arg Glu Asp Asp Val Met Gly
                100                 105                 110

Ile Asp Glu Ile Ala Glu Pro Val Gly Val Val Ala Gly Val Thr Pro
            115                 120                 125

Val Thr Asn Pro Thr Ser Thr Ala Ile Phe Lys Ser Leu Ile Ala Leu
    130                 135                 140

Lys Thr Arg Cys Pro Ile Ile Phe Gly Phe His Pro Gly Ala Gln Lys
145                 150                 155                 160

Cys Ser Val Glu Ala Ala Lys Ile Val Arg Asp Ala Ala Ile Glu Ala
                165                 170                 175
```

```
Gly Ala Pro Glu Asn Cys Ile Gln Trp Ile Glu His Pro Ser Ile Glu
            180                 185                 190

Ala Thr Gly Ala Leu Met Lys His Asp Gly Ile Ala Thr Ile Leu Ala
        195                 200                 205

Thr Gly Gly Pro Gly Met Val Lys Ala Ala Tyr Ser Ser Gly Lys Pro
    210                 215                 220

Ala Leu Gly Val Gly Ala Gly Asn Ala Pro Ala Tyr Val Asp Lys Asn
225                 230                 235                 240

Val Asp Ile Val Arg Ala Ala Asn Asp Leu Val Leu Ser Lys His Phe
                245                 250                 255

Asp Tyr Gly Met Ile Cys Ala Thr Glu Gln Ala Ile Ile Ala Asp Lys
            260                 265                 270

Glu Val Tyr Ala Pro Leu Ile Lys Glu Leu Lys Arg Arg Lys Ala Tyr
        275                 280                 285

Phe Val Asn Asp Glu Glu Lys Ala Lys Leu Glu Gln Tyr Met Phe Gly
    290                 295                 300

Cys Thr Ala Tyr Ser Gly Gln Thr Pro Lys Leu Asn Ser Val Val Pro
305                 310                 315                 320

Gly Lys Ser Pro Gln Tyr Ile Ala Lys Ala Ala Gly Phe Glu Ile Pro
                325                 330                 335

Glu Asp Ala Thr Ile Leu Ala Ala Glu Cys Lys Glu Val Gly Glu Asn
            340                 345                 350

Glu Pro Leu Thr Met Glu Lys Leu Ala Pro Val Gln Ala Val Leu Lys
        355                 360                 365

Ser Asp Asn Lys Glu Gln Ala Phe Glu Met Cys Glu Ala Met Leu Lys
    370                 375                 380

His Gly Ala Gly His Thr Ala Ile His Thr Asn Asp Gln Ala Leu
385                 390                 395                 400

Val Arg Glu Tyr Gly Gln Arg Met His Ala Cys Arg Ile Ile Trp Asn
                405                 410                 415

Ser Pro Ser Ser Leu Gly Gly Val Gly Asp Ile Tyr Asn Ala Ile Ala
            420                 425                 430

Pro Ser Leu Thr Leu Gly Cys Gly Ser Tyr Gly Gly Asn Ser Val Ser
        435                 440                 445

Gly Asn Val Gln Ala Val Asn Leu Leu Asn Ile Lys Arg Ile Ala Arg
    450                 455                 460

Arg Asn Asn Asn Met Gln Trp Phe Lys Ile Pro Ala Lys Thr Tyr Phe
465                 470                 475                 480

Glu Pro Asn Ala Ile Lys Tyr Leu Arg Asp Met Tyr Gly Ile Glu Lys
                485                 490                 495

Ala Val Ile Val Cys Asp Lys Val Met Glu Gln Leu Gly Ile Val Asp
            500                 505                 510

Lys Ile Ile Asp Gln Leu Arg Ala Arg Ser Asn Arg Val Thr Phe Arg
        515                 520                 525

Ile Ile Asp Tyr Val Glu Pro Glu Pro Ser Val Glu Thr Val Glu Arg
    530                 535                 540

Gly Ala Ala Met Met Arg Glu Glu Phe Glu Pro Asp Thr Ile Ile Ala
545                 550                 555                 560

Val Gly Gly Gly Ser Pro Met Asp Ala Ser Lys Ile Met Trp Leu Leu
                565                 570                 575

Tyr Glu His Pro Glu Ile Ser Phe Ser Asp Val Arg Glu Lys Phe Phe
            580                 585                 590
```

-continued

```
Asp Ile Arg Lys Arg Ala Phe Lys Ile Pro Pro Leu Gly Lys Lys Ala
        595                 600             605
Lys Leu Val Cys Ile Pro Thr Ser Ser Gly Thr Gly Ser Glu Val Thr
    610             615                 620
Pro Phe Ala Val Ile Thr Asp His Lys Thr Gly Tyr Lys Tyr Pro Ile
625                 630                 635                 640
Thr Asp Tyr Ala Leu Thr Pro Ser Val Ala Ile Val Asp Pro Val Leu
                645                 650                 655
Ala Arg Thr Gln Pro Arg Lys Leu Ala Ser Asp Ala Gly Phe Asp Ala
            660                 665                 670
Leu Thr His Ala Phe Glu Ala Tyr Val Ser Val Tyr Ala Asn Asp Phe
        675                 680                 685
Thr Asp Gly Met Ala Leu His Ala Ala Lys Leu Val Trp Asp Asn Leu
    690                 695                 700
Ala Glu Ser Val Asn Gly Glu Pro Gly Glu Glu Lys Thr Arg Ala Gln
705                 710                 715                 720
Glu Lys Met His Asn Ala Ala Thr Met Ala Gly Met Ala Phe Gly Ser
                725                 730                 735
Ala Phe Leu Gly Met Cys His Gly Met Ala His Thr Ile Gly Ala Leu
            740                 745                 750
Cys His Val Ala His Gly Arg Thr Asn Ser Ile Leu Leu Pro Tyr Val
        755                 760                 765
Ile Arg Tyr Asn Gly Ser Val Pro Glu Glu Pro Thr Ser Trp Pro Lys
    770                 775                 780
Tyr Asn Lys Tyr Ile Ala Pro Glu Arg Tyr Gln Glu Ile Ala Lys Ser
785                 790                 795                 800
Leu Gly Val Asn Pro Gly Lys Thr Pro Glu Glu Gly Val Glu Asn Leu
                805                 810                 815
Ala Lys Ala Val Glu Asp Tyr Arg Asp Asn Lys Leu Gly Met Asn Lys
            820                 825                 830
Ser Phe Lys Glu Cys Gly Val Asp Glu Asp Tyr Tyr Trp Ser Ile Ile
        835                 840                 845
Asp Gln Ile Gly Met Arg Ala Tyr Glu Asp Gln Cys Ala Pro Ala Asn
850                 855                 860
Pro Arg Ile Pro Gln Ile Glu Asp Met Lys Asp Ile Ala Ile Ala Ala
865                 870                 875                 880
Tyr Tyr Gly Val Ser Gln Glu Glu Gly His Lys Leu Arg Ile Glu Arg
                885                 890                 895
Gln Gly Glu Ala Ala Thr Glu Glu Ala Ser Glu Arg Ala
            900                 905
```